(12) United States Patent
Moffat et al.

(10) Patent No.: US 8,217,050 B2
(45) Date of Patent: Jul. 10, 2012

(54) ADENINE DERIVATIVE AS INHIBITORS OF HSP90 FOR THE TREATMENT OF CANCER

(75) Inventors: David Festus Charles Moffat, Abingdon (GB); Simon Christopher Hirst, Nottingham (GB); Stuart Thomas Onions, Nottingham (GB)

(73) Assignee: Chroma Therapeutics Limited, Oxfordshire (GB)

( * ) Notice: Subject to any disclaimer, the term of this patent is extended or adjusted under 35 U.S.C. 154(b) by 377 days.

(21) Appl. No.: 12/513,658

(22) PCT Filed: Nov. 5, 2007

(86) PCT No.: PCT/GB2007/004216
§ 371 (c)(1),
(2), (4) Date: Jun. 25, 2009

(87) PCT Pub. No.: WO2008/056120
PCT Pub. Date: May 15, 2008

(65) Prior Publication Data
US 2010/0035901 A1 Feb. 11, 2010

(30) Foreign Application Priority Data
Nov. 6, 2006 (GB) .................................. 0622084.2

(51) Int. Cl.
C07D 473/34 (2006.01)
A61K 31/52 (2006.01)
A61P 11/06 (2006.01)
A61P 37/06 (2006.01)
A61P 19/02 (2006.01)
A61P 3/10 (2006.01)
A61P 17/06 (2006.01)
C07F 7/18 (2006.01)
C07F 7/10 (2006.01)

(52) U.S. Cl. ......... 514/263.24; 514/263.37; 514/263.38; 544/265; 544/276; 544/277; 556/418; 556/420; 560/27; 560/115

(58) Field of Classification Search ............. 514/263.24, 514/263.37, 263.38; 544/265, 276, 277
See application file for complete search history.

(56) References Cited

U.S. PATENT DOCUMENTS
5,263,475 A 11/1993 Altermatt et al.
2005/0107343 A1 5/2005 Kasibhatla et al.

FOREIGN PATENT DOCUMENTS
| EP | 0 505 321 A2 | 9/1992 |
| WO | WO 02/36075 A2 | 5/2002 |
| WO | WO 03/037860 A2 | 5/2003 |
| WO | WO 2006/117567 A2 | 11/2006 |
| WO | WO 2007/134298 A2 | 11/2007 |
| WO | WO 2009136144 A1 * | 11/2009 |

OTHER PUBLICATIONS

International Search Report for related International Application No. PCT/GB2007/004216 mailed Feb. 28, 2008.
Written Opinion of the International Searching Authority for related International Application No. PCT/GB/2007/004216 mailed Feb. 28, 2008.
Wegele et al., "Hsp70 and Hsp90—A Relay Team for Protein Folding," *Rev. Physiol. Biochem. Pharmacol.*, vol. 151, pp. 1-44 (2004).
Csermely et al., "The 90-kDa Molecular Chaperone Family: Structure, Function, and Clinical Applications. A Comprehensive Review," *Pharmacol. Ther.*, vol. 79, No. 2, pp. 129-168 (1998).
Freeman et al., "Disassembly of Transcriptional Regulatory Complexes by Molecular Chaperones," Science, vol. 296, pp. 2232-2235 (2002).
Smith et al., "Progesterone Receptor Structure and Function Altered by Geldanamycin, an hsp90- Binding Agent," *Molecular and Cellular Biology*, pp. 6804-6812 (1995).
Pratt, The hsp90-based Chaperone System: Involvement in Signal Transduction from a Variety of Hormone and Growth Factor Receptors (44252), *Proc. Soc. Exp. Biol. Med.*, vol. 217, pp. 420-434 (1998).
Morimoto, "Dynamic Remodeling of Transcription Complexex by Molecular Chaperones," *Cell*, vol. 110, pp. 281-284 (2002).
Sangster et al., "Hsp90 and Chromatin," *Cell Cycle*, vol. 2, No. 3, pp. 166-168 (2003).
Jameel et al., "Clinical and Biological Significance of HSP89 Alpha in Human Breast Cancer," *Int. J. Cancer*, vol. 50, pp. 409-415 (1992).
Mosser et al., "Molecular Chaperones and the Stress of Oncogenesis," *Oncogene*, vol. 23, pp. 2907-2918 (2004).
Basso et al., "Akt Forms and Intracellular Complex with Heat Shock Protein 90 (Hsp90) and Cdc37 and Is Destabilized by Inhibitors of Hsp90," *The Journ. Of Biol. Chem.*, vol. 277, No. 42, pp. 39858-39866 (2002).
Vanden Berghe et al., "Disruption of HSP90 Function Reverts Tumor Necrosis Factor-induced Necrosis to Apoptosis," *The Journ. Of Biol. Chem.*, vol. 278, No. 8, pp. 5622-5629 (2003).
Chen et al., "TNF-Induced Recruitment and Activation of the IKK Complex Require Cdc37 and Hsp90," *Molecular Cell*, vol. 9, pp. 401-410 (2002).
Neckers, "Hsp90 Inhibitors as Novel Cancer Chemotherapeutic Agents," *Trends in Molecular Medicine*, vol. 8, No. 4 (Suppl.), pp. S55-S61 (2002).

(Continued)

*Primary Examiner* — Mark Berch
(74) *Attorney, Agent, or Firm* — Foley & Lardner LLP

(57) ABSTRACT

The invention provides a compound which is (a) an amino acid derivative of formula (I) or a tautomer thereof, or (b) a pharmaceutically acceptable salt, N-oxide, hydrate or solvate thereof: wherein $R^1$, $R^2$, $L^1$, Het, A, x, y and W are as defined herein. The compounds are useful in the treatment of diseases mediated by HSP90.

(I)

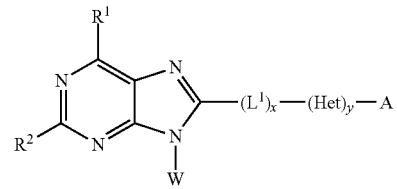

14 Claims, No Drawings

OTHER PUBLICATIONS

Dutta et al., "GHKL, an Emergent ATPase/Kinase Superfamily," *Trends Biochem. Sci.*, No. 25, pp. 24-28 (2000).

Meyer et al., "Structural and Functional Analysis of the Middle Segment of Hsp90: Implications for ATP Hydrolysis and Client Protein and Cochaperone Interactions," *Molecular Cell*, vol. 11, pp. 647-658 (2003).

Xu et al., "Chaperone-dependent E3 Ubiquitin Ligase Chip Mediates a Degradative Pathway for c-ErbB2/Neu," *PNAS*, vol. 99, No. 20, pp. 12847-12852 (2002).

Mellwrath et al., "Cell-cycle Arrests and p53 Accumulation Induced by Geldanamycin in Human Ovarian Tumour Cells," *Cancer Chemotheray Pharmacol.*, vol. 37, pp. 423-428 (1996).

Basso et al., "Ansamycin Antibiotics Inhibit Akt Activation and Cyclin D Expression in Breast Cancer Cells that Overexpress HER2," *Oncogene*, vol. 21, pp. 1159-1166 (2002).

Biamonte et al., "Orally Active Purine-Based Inhibitors of the Heat Shock Protein 90," *Journ. Of Medicinal Chemistry*, vol. 49, No. 2, pp. 817-829 (2006).

Immormino et al., "Structural and Quantum Chemical Studies of 8-Aryl-sulfanyl Adenine Class Hsp90 Inhibitors," *Journ. Of Medicinal Chemistry*, vol. 49, No. 16, pp. 4953-4960 (2006).

Skehan et al., "New Colorimetric Cytotoxicity Assay for Anticancer-Drug Screening," *J. Natl. Canc. Inst.*, vol. 82, No. 13, pp. 1107-1112 (1990).

Olsen et al., "Synthesis of N.alpha.,N.delta.-protected N.delta.-hydroxy-L-ornithine from L-glutamic acid," *The Journ. Of Organic Chem.*, vol. 49, pp. 3527-3534 (1984).

Sollars et al., "Evidence for an Epigenetic Mechanism by which Hsp90 Acts as a Capacitor for Morphological Evolution," *Nature genetics*, vol. 33, pp. 70-74 (2003).

\* cited by examiner

ADENINE DERIVATIVE AS INHIBITORS OF HSP90 FOR THE TREATMENT OF CANCER

CROSS-REFERENCE TO RELATED APPLICATIONS

This application is the U.S. National Phase of International Patent Application No. PCT/GB2007/004216, filed on Nov. 5, 2007, which claims the benefit of priority from Great Britain Application No. 0622084.2, filed on Nov. 6, 2006. The contents of these applications are incorporated herein by reference in their entirety.

This invention relates to a series of amino acid derivatives, to compositions containing them, to processes for their preparation and to their use in medicine as HSP90 inhibitors. The compounds may also be of use in the treatment of cell proliferative diseases such as cancer which are mediated by inappropriate HSP90 activity as well as inflammatory and immune disorders such as rheumatoid arthritis, psoriasis, Crohn's disease, ulcerative colitis, systemic lupus erythematosis, and disorders related to angiogenesis age related macular degeneration, diabetic retinopathy and endometriosis. The compounds may also be of use in the protection of normal cells against the action of cytotoxic agents. The present invention encompasses compounds that are derivatives of adenine.

BACKGROUND TO THE INVENTION

Cells respond to stress by increasing synthesis of a number of heat shock proteins or HSPs, also known as molecular chaperones. The heat shock proteins assist general protein folding and prevent non-functional side reactions such as non-specific aggregation of misfolded or unfolded proteins. Heat shock protein 90 (HSP90) in particular has been identified as an important mediator of cancer cell survival.

Most HSPs are ubiquitously expressed under normal conditions, their basal levels facilitating normal protein folding and guarding the proteosome from the dangers of misfolding or aggregation, [Wegele et al, Rev. Physiol. Biochem. Pharmacol., 2004, 151, 1-44]. Under non-stressed conditions HSP90 comprises as much as 1-2% of total cellular protein content, whereas in tumour cells it is expressed at levels 2- to 10-fold higher in comparison to normal cells. These chaperone proteins are required for essential housekeeping functions, such as de novo protein folding during nascent polypeptide-chain synthesis, translocation of proteins across membranes and normal protein turnover. HSPs also participate in higher-order functions such as post-translational regulation of signalling molecules [Csermelt et al, Pharmacol. Ther, 1998, 79, 129-168], the assembly and disassembly of transcriptional complexes [Science 2002, 296, 2232-2235] and the processing of immunogenic peptides by the immune system.

HSPs function as components of multi-protein complexes which contain other chaperones, co-chaperones, modulators of ATPase activity and various accessory proteins. The components of the HSP90 chaperone complex include HSP70, HSP40, HIP, HOP, CDC37/p50, AHA1, p23 and immunophilin. Chaperones typically interact with client proteins in a cyclical, iterative fashion which is driven by ATP hydrolysis, [Smith et al, Mol. Cell Biol. 1995, 15, 6804-6812]. Targeting the nucleotide-binding pockets of HSP90 with small molecules may therefore provide a method of modulating the activity of the chaperone complex. HSP90 is unique amongst the chaperones as it is not required for biogenesis of most polypeptides. Many of its client proteins are conformationally labile signal transducers which are critical to cell growth and survival, [Pratt et al, Proc. Soc. Exp. Biol. Med., 1998, 217, 420-431]. Post-translational interactions with its clients allows HSP90 to couple stress response to changes in signal transduction pathways and transcriptional responses, [Morimoto et al, Cell, 2002, 110, 281-284]. Studies in *Drosophila melanogaster* have demonstrated that compromising the function of HSP90 can induce epigenetic alteration in gene expression as well as heritable alterations in chromatin state [Solars et al, Nature Genet. 2003, 33, 70-74 and Sangster et al, Cell Cycle, 2003, 2, 166-168].

A common feature of both solid and haematological malignancies is increased expression of one or more HSPs. Overexpression of HSP90 in breast cancer correlates with poor prognosis [Jameel et al, Int. J. Cancer 1992, 50, 409-415]. Increased chaperone expression contributes to oncogenesis at several levels. Increased abundance of HSPs in advanced cancers reflects an appropriate cytoprotective stress response to hypoxic and acidotic microenvironment of the tumour. At the molecular level increased chaperone activities appear to allow tumour cells to tolerate the deregulation in intracellular signalling associated with neoplastic transformation and thereby provide a mechanism for tumour cells to avoid apoptosis [Mosser et al, Oncogene 2004, 23, 2907]. The modulation of tumour cell apoptosis by HSP90 and its co-chaperones is mediated through effects on AKT, [Basso et al, J. Biol. Chem., 2003, 277, 39858-39866], tumour necrosis factor (TNF) receptors [Vanden Bergh et al, J. Biol. Chem. 2003, 278, 5622-5629] and NF-κB function [Chen et al, Mol. Cell, 2002, 9, 401-410].

Many kinases are client proteins of HSP90 including several which play a significant role in the progression of malignant phenotype such as HER2, AKT and RAF-1, [Neckers et al, Trends Mol. Med. 2002, 8, S55-S61]. Ligand-dependent transcription factors (e.g. steroid receptors), transcription factors (e.g. HIF-1α) containing PAS domains and mutated or chimeric signalling proteins (mutated p53, NPM-ALK kinase, p210$^{Bcr-Abl}$) are also HSP90 clients. In addition some client proteins are involved other fundamental processes of tumorigenesis, namely apoptosis evasion (e.g. Apaf-1, RIP), immortality (e.g. hTert), angiogenesis (e.g. VEGFR, Flt-3, FAK, HIF-1) and metastasis (c-Met).

HSP90 resides predominantly in the cytoplasm, where it exists at a homodimer. Each monomer is comprised of three main domains. The N-terminal domain contains an unusual adenine nucleotide-binding pocket defined by a Bergerat fold, [Dutta et al, Trends Biochem. Sci., 2000, 25, 24-28]. Structural alterations driven by the hydrolysis of ATP in this fold appear to have an essential role in the chaperoning activity of the HSP90 dimer. In eukaryotes a highly charged linker sequence connects the N-terminal domain to the 'middle region' of HSP90. The structure of this middle region indicates that is has an important role in modulating ATP hydrolysis by interacting with the γ-phosphate of ATP molecules bound to the protein, [Meyer et al, Mol. Cell 2003, 11, 647-658]. The N-terminal ATP-binding site is also the site of interaction of the structurally unrelated natural products geldanamycin and radicicol. These compounds prevent the chaperone from cycling between its ADP- and ATP-bound conformations. Drug binding at the N-terminus of HSP90 seems to recruit E3 ubiquitin ligases such as CHIP (carboxy terminus of HSP70-interacting protein) to the many client proteins that are normally expressed by HSP90 protein complexes [Xu et al, Proc. Natl. Acad. Sci., 2002, 99, 12847-12852]. This recruitment leads to proteosomal degradation of the clients and depletion of their cellular levels.

In normal and many cancer cell lines, HSP90 inhibitors induce a predominant G1 cell-cycle arrest in a p53-independent manner, [McIlwrath et al, Cancer Chemother. Pharmacol. 1996, 37, 423-428]. Disruption of anti-apoptotic signalling in tumour cells occurs following exposure to HSP90 inhibitors and can enhance the pro-apoptotic effects of cytotoxic agents [Basso et al, Oncogene 2002, 21, 1159-1162].

We have now discovered a group of compounds which are potent and selective inhibitors of HSP90 and the isoforms and splice variants thereof. The compounds are thus of use in medicine, for example in the treatment of a variety of proliferative disease states, where inappropriate action of HSP90 may be involved such as cancer, inflammatory and immune disorders such as rheumatoid arthritis, psoriasis, Crohn's disease, ulcerative colitis, systemic lupus erythematosis, and disorders related to angiogenesis age related macular degeneration, diabetic retinopathy and endometriosis. The compounds may also be of use in the protection of normal cells against the action of cytotoxic agents. The compounds of the invention are related to the HSP90 inhibitors encompassed by the disclosure in International Patent Application Nos. WO 2003037860 and WO2002036075 as well as the publication J. Med, Chem 2006, 49, 817-829 but differ therefrom in that the present compounds have the amino acid ester motif referred to above.

BRIEF DESCRIPTION OF THE INVENTION

The invention provides a compound which is (a) an amino acid derivative of formula (I) or a tautomer thereof, or (b) a pharmaceutically acceptable salt, N-oxide, hydrate or solvate thereof:

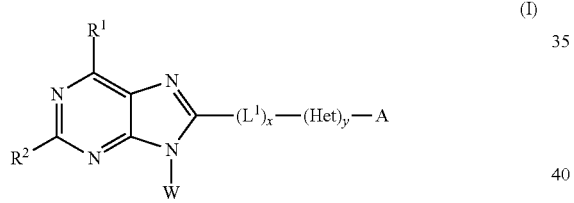

(I)

wherein:
R$^1$ represents a hydrogen or halogen atom, or a cyano, nitro, —N$_3$, C$_{1-6}$ alkyl, C$_{2-6}$ alkenyl, C$_{2-6}$ alkynyl, C$_{1-6}$ alkoxy, C$_{2-6}$ alkenyloxy, hydroxyl, mercapto, C$_{1-6}$ alkylthio, C$_{2-6}$ alkenylthio, guanidine, amidine, —NR'R'', —NR'''OR' or —NR'''R'R'' group wherein each R', R'' and R''' group is the same or different and represents hydrogen or C$_{1-4}$ alkyl, or represents a group of formula —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —OCONH$_2$, —OCONHR$^A$, —OCONR$^A$R$^B$, —NHCOR$^A$, NHCOOR$^A$, —NR$^B$COOR$^A$, —NHSO$_2$R$^A$, —NR$^B$SO$_2$R$^A$, —NHSO$_2$OR$^A$, —NR$^B$SO$_2$OH, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$ or —NR$^A$CONR$^A$R$^B$ wherein R$^A$ and R$^B$ are the same or different and represent C$_{1-6}$ alkyl, C$_{3-6}$-cycloalkyl, non-fused phenyl or a non-fused 5- to 6-membered heteroaryl, or R$^A$ and R$^B$ when attached to the same nitrogen atom form a non-fused 5- or 6-membered heterocyclyl group;

R$^2$ represents a hydrogen or halogen atom, or a cyano, nitro, —N$_3$, C$_{1-6}$ alkyl, C$_{1-6}$ alkenyl, C$_{2-6}$ alkynyl group, or a group of formula —NR'R'', —CO$_2$R', —SO$_2$R', —NR'R'' or —CONR'R'' where R' and R'' are the same or different and represent hydrogen or unsubstituted C$_{1-4}$ alkyl, or a C$_{6-10}$ aryl, 5- to 10-membered heteroaryl, C$_{3-7}$ carbocyclyl or 5- to 10-membered heterocyclyl group;

x and y are the same or different and represent zero or 1;

L$^1$ represents C$_{1-4}$ alkylene;

Het represents —S—, —S(O)—, —S(O)$_2$—, —NR'— or —O— where R' represents hydrogen or unsubstituted C$_{1-4}$ alkyl;

A represents a C$_{6-10}$ aryl, 5- to 10-membered heteroaryl, C$_{3-7}$ carbocyclyl or 5- to 10-membered heterocyclyl group which is optionally fused to a further C$_{6-10}$ aryl, 5- to 10-membered heteroaryl, C$_{3-7}$ carbocyclyl or 5- to 10-membered heterocyclyl group;

W is a group of formula —[CH$_2$]$_z$—Y$^1$-L$^2$-R, wherein:
z is 0 or 1;
Y$^1$ represents a bond or a group of formula —S—, —O—, —(C=O)—, —(S=O)—, —S(O$_2$)—, —NR$^3$—, —(C=O)NR$^3$—, —NR$^3$(C=O)—, —S(O$_2$)NR$^3$—, —NR$^3$S(O$_2$)—, —NR$^3$(C=O)NR$^4$— or —NR$^3$(C=S)NR$^4$—, wherein R$^3$ and R$^4$ are the same or different and represent hydrogen or C$_{1-6}$ alkyl;
L$^2$ is a divalent radical of formula -(Alk$^1$)$_m$(Q)$_n$(Alk$^2$)$_p$— wherein:
m, n and p are independently 0 or 1;
Q either (i) represents a phenyl, 5- to 10-membered heteroaryl, C$_{3-7}$ carbocyclyl or 5- to 10-membered heterocyclyl group optionally fused to a further phenyl, 5- to 10-membered heteroaryl, C$_{3-7}$ carbocyclyl or 5- to 10-membered heterocyclyl group; or (ii) in the case where p is 0, represents a group of formula -Q$^1$-X$^1$— wherein X$^1$ represents —O—, —S— or —NR$^5$— wherein R$^5$ is hydrogen or C$_{1-4}$ alkyl, and Q$^1$ represents a phenyl, 5- to 10-membered heteroaryl, C$_{3-7}$ carbocyclyl or 5- to 10-membered heterocyclyl group optionally fused to a further phenyl, 5- to 10-membered heteroaryl, C$_{3-7}$ carbocyclyl or 5- to 10-membered heterocyclyl group;
Alk$^1$ and Alk$^2$ are the same or different and represent C$_{3-7}$ carbocyclyl groups, or represent C$_{1-6}$ alkylene, C$_{2-6}$ alkenylene, or C$_{2-6}$ alkynylene groups which may optionally contain or terminate in an ether (—O—), thioether (—S—) or amino (—NR$^6$—) link wherein R$^6$ represents hydrogen or C$_{1-4}$ alkyl;
R is a radical of formula (X) or (Y):

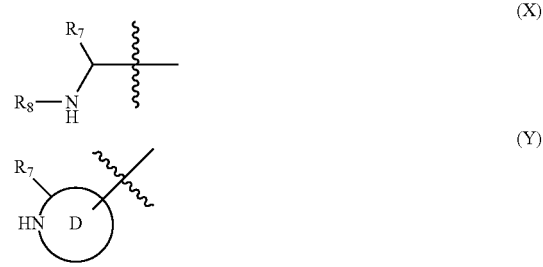

wherein:
R$^7$ is a group —COOH or an ester group which is hydrolysable by one or more intracellular carboxylesterase enzymes to a —COOH group;
R$^8$ represents hydrogen or a C$_{1-6}$ alkyl, —(C=O)R$^9$, —(C=O)OR$^{10}$ or —(C=O)NR$^{10}$ group wherein R⁹ represents hydrogen, a $C_{1-6}$ alkyl group, a phenyl, 5- to 10-membered heteroaryl, $C_{3-7}$ carbocyclyl or 5- to 10-membered heterocyclyl group optionally fused to a further phenyl, 5- to 10-membered heteroaryl, $C_{3-7}$ carbocyclyl or 5- to 10-membered heterocyclyl group, or R⁹ represents a group of formula -Alk⁴-Cyc wherein Alk⁴ represents a $C_{1-6}$ alkylene group and Cyc represents a phenyl, 5- to 10-membered heteroaryl or 5- to 10-membered heterocyclyl group optionally fused to a further phenyl, 5- to 10-membered heteroaryl, $C_{3-7}$ carbocyclyl or 5- to 10-membered heterocyclyl group, and R¹⁰ represents hydrogen or $C_{1-6}$ alkyl, or wherein R⁸ represents a phenyl, 5- to 10-membered heteroaryl, $C_{3-7}$ carbocyclyl or 5- to 10-membered heterocyclyl group optionally fused to a further phenyl, 5- to 10-membered heteroaryl, $C_{3-7}$-carbocyclyl or 5- to 10-membered heterocyclyl group; and D represents a 5- or 6-membered heteroaryl or 5- or 6-membered heterocyclyl group wherein R⁷ is linked to a ring carbon adjacent the ring nitrogen shown, and wherein ring D is optionally fused to a further phenyl, 5- to 10-membered heteroaryl, $C_{3-7}$ carbocyclyl or 5- to 10-membered heterocyclyl group in which case the bond shown intersected by a wavy line may be from a ring atom in said second ring;

wherein the alkyl, alkylene, alkenyl and alkynyl moieties in R¹, R², R³, R⁴, R⁵, R⁶, R⁸, R⁹, R¹⁰, Alk¹, Alk² and Alk³ are unsubstituted or substituted by 1, 2 or 3 substituents which are the same or different and are selected from halogen atoms and $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, mercapto, cyano, nitro, $C_{1-4}$ hydroxyalkyl, $C_{2-4}$ hydroxyalkenyl, $C_{1-4}$ alkylthio, $C_{2-4}$ alkenylthio, phenyl, —NR'R" groups wherein each R' and R" is the same or different and represents hydrogen or $C_{1-4}$ alkyl, and groups of formula —COOH, —COOR$^A$, —COR$^A$, —SO₂R$^A$, —CONH₂, —SO₂NH₂, —CONHR$^A$, —SO₂NHR$^A$, —CONR$^A$R$^B$, —SO₂NR$^A$R$^B$, —OCONH₂, —OCONHR$^A$, —OCONR$^A$R$^B$, —NHCOR$^A$, NHCOOR$^A$, —NR$^B$COOR$^A$, —NHSO₂OR$^A$, —NR$^B$SO₂OH, —NR$^B$SO₂OR$^A$, —NHCONH₂, —NR$^A$CONH₂, —NHCONHR$^B$, —NR$^A$CONHR$^B$, —NHCONR$^A$R$^B$ or —NR$^A$CONR$^A$R$^B$ wherein R$^A$ and R$^B$ are the same or different and represent $C_{1-6}$ alkyl, $C_{3-6}$ cycloalkyl, phenyl or a non-fused 5- to 6-membered heteroaryl, or R$^A$ and R$^B$ when attached to the same nitrogen atom form a non-fused 5- or 6-membered heterocyclyl group; and the phenyl, heteroaryl, heterocyclyl and carbocyclyl moieties in R¹, R², R⁸, R⁹, A, Q, Q¹ and D are unsubstituted or substituted by 1, 2, 3 or 4 substituents which are the same or different and are selected from halogen atoms and $C_4$ alkyl, $C_{1-4}$ alkylene, $C_{2-4}$-alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, mercapto, cyano, nitro, $C_{1-4}$ hydroxyalkyl, $C_{2-4}$ hydroxyalkenyl, $C_{1-4}$ alkylthio, $C_{2-4}$ alkenylthio, —NR'R" groups wherein each R' and R" is the same or different and represents hydrogen or $C_{1-4}$ alkyl, and groups of formula —COOH, —COOR$^A$, —COR$^A$, —SO₂R$^A$, —CONH₂, —SO₂NH₂, —CONHR$^A$, —SO₂NHR$^A$, —CONR$^A$R$^B$, —SO₂NR$^A$R$^B$, —OCONH₂, —OCONHR$^A$, —OCONR$^A$R$^B$, —NHCOR$^A$, NHCOOR$^A$, —NR$^B$COOR$^A$, —NHSO₂OR$^A$, —NR$^B$SO₂OH, —NR$^B$SO₂OR$^A$, —NHCONH₂, —NR$^A$CONH₂, —NHCONHR$^B$, —NR$^A$CONHR$^B$, —NHCONR$^A$R$^B$ or —NR$^A$CONR$^A$R$^B$ wherein R$^A$ and R$^B$ are the same or different and represent $C_{1-6}$ alkyl, $C_{3-6}$ cycloalkyl, phenyl or a non-fused 5- to 6-membered heteroaryl, or R$^A$ and R$^B$ when attached to the same nitrogen atom form a non-fused 5- or 6-membered heterocyclyl group.

The compounds of the invention are characterised by the presence in the molecule of an amino acid motif or an amino acid ester motif which is hydrolysable by an intracellular carboxylesterase. Compounds of the invention can cross the cell membrane, and, if in the ester form, can be hydrolysed to the acid by the intracellular carboxylesterases. The polar hydrolysis product accumulates in the cell since it does not readily cross the cell membrane. Hence the HSP90 activity of the compound is prolonged and enhanced within the cell.

Preferably the compounds of the invention are compounds of formula (I) or a tautomer thereof, or a pharmaceutically acceptable salt thereof.

In another broad aspect the invention provides the use of a compound as defined above in the manufacture of a medicament for inhibiting the activity of HSP90. More preferably, the invention provides the use of a compound as defined above in the manufacture of a medicament for use in treating a disorder mediated by HSP90.

The compounds with which the invention is concerned may be used for the inhibition of HSP90 activity ex vivo or in vivo.

In one aspect of the invention, the compounds of the invention may be used in the preparation of a composition for treatment of cancer, inflammatory and immune disorders such as rheumatoid arthritis, psoriasis, Crohn's disease, ulcerative colitis, systemic lupus erythematosis, and disorders related to angiogenesis age related macular degeneration, diabetic retinopathy and endometriosis. The compounds may also be of use in the protection of normal cells against the action of cytotoxic agents.

In another aspect, the invention provides a method for the treatment of the foregoing disease types, which comprises administering to a subject suffering such disease an effective amount of a compound as defined above.

DETAILED DESCRIPTION OF THE INVENTION

Although the above definitions potentially include molecules of high molecular weight, it is preferable, in line with general principles of medicinal chemistry practice, that the compounds with which this invention is concerned should have molecular weights of no more than 600.

The alkyl, alkylene, alkenyl, alkenylene, alkynyl and alkynylene moieties in R¹, R², R³, R⁴, R⁵, R⁶, R⁸, R⁹, R¹⁰, Alk¹, Alk² and Alk³ are unsubstituted or substituted by 1, 2 or 3 substituents which are the same or different and are selected from halogen atoms and $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, mercapto, cyano, nitro, $C_{1-4}$ hydroxyalkyl, $C_{2-4}$ hydroxyalkenyl, $C_{1-4}$ alkylthio, $C_{2-4}$ alkenylthio, —NR'R" groups wherein each R' and R" is the same or different and represents hydrogen or $C_{1-4}$ alkyl, and from groups of formula —COOH, —COOR$^A$, —COR$^A$, —SO₂R$^A$, —CONH₂, —SO₂NH₂, —CONHR$^A$, —SO₂NHR$^A$, —CONR$^A$R$^B$, —SO₂NR$^A$R$^B$, —OCONH₂, —OCONHR$^A$, —OCONR$^A$R$^B$, —NHCOR$^A$, NHCOOR$^A$, —NR$^B$COOR$^A$, —NHSO₂OR$^A$, —NR$^B$SO₂OH, —NR$^B$SO₂OR$^A$, —NHCONH₂, —NR$^A$CONH₂, —NHCONHR$^B$, —NR$^A$CONHR$^B$, —NHCONR$^A$R$^B$ and —NR$^A$CONR$^A$R$^B$ wherein R$^A$ and R$^B$ are the same or different and represent C$_{1-6}$ alkyl, non-fused C$_{3-6}$ cycloalkyl, non-fused phenyl or non-fused 5- to 6-membered heteroaryl, or R$^A$ and R$^B$ when attached to the same nitrogen atom form a non-fused 5- or 6-membered heterocyclyl group. Unless otherwise specified, the substituents described above are preferably themselves unsubstituted.

Preferred substituents include halogen atoms and C$_{1-4}$ alkyl, C$_{2-4}$ alkenyl, C$_{1-4}$ alkoxy, C$_{2-4}$ alkenyloxy, C$_{1-4}$ haloalkyl, C$_{2-4}$ haloalkenyl, C$_{1-4}$ haloalkoxy, C$_{2-4}$ haloalkenyloxy, hydroxyl, mercapto, cyano, nitro, CIA hydroxyalkyl, C$_{2-4}$ hydroxyalkenyl, C$_{1-4}$ alkylthio, C$_{2-4}$ alkenylthio, and —NR'R" groups wherein each R' and R" is the same or different and represents hydrogen or C$_{1-4}$ alkyl.

More preferred substituents include halogen, C$_{1-4}$ alkyl, C$_{2-4}$ alkenyl, C$_{1-4}$ alkoxy, hydroxyl, C$_{1-4}$ haloalkyl, C$_{2-4}$ haloalkenyl, C$_{1-4}$ haloalkyloxy, C$_{2-4}$ haloalkenyloxy and —NR'R" wherein R' and R" are the same or different and represent hydrogen or C$_{1-2}$ alkyl. More preferred substituents are halogen, C$_{1-2}$ alkoxy, C$_{1-2}$ haloalkyl, hydroxyl and —NR'R" wherein R' and R" are the same or different and represent hydrogen or C$_{1-2}$ alkyl. In particular, it is preferred that R' and R" are unsubstituted.

When the alkyl, alkylene, alkenylene and alkynylene moieties are substituted by two or three substituents, it is preferred that not more than two substituents are selected from cyano and nitro. More preferably, not more than one substituent is selected from cyano and nitro. Furthermore, when the alkyl, alkylene, alkenylene and alkynylene moieties are substituted by two or three substituents, it is preferred that not more than one substituent is selected from —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —OCONH$_2$, —OCONHR$^A$, —OCONR$^A$R$^B$, —NHCOR$^A$, NHCOOR$^A$, —NR$^B$COOR$^A$, —NHSO$_2$OR$^A$, —NR$^B$SO$_2$OH, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$ and —NR$^A$CONR$^A$R$^B$.

As used herein, a C$_{1-6}$ alkyl group or moiety is a linear or branched alkyl group or moiety containing from 1 to 6 carbon atoms, for example a C$_{1-4}$ alkyl group or moiety containing from 1 to 4 carbon atoms. Examples of C$_{1-4}$ alkyl groups include methyl, ethyl, n-propyl, i-propyl, n-butyl, i-butyl and t-butyl. For the avoidance of doubt, where two alkyl moieties are present in a group, the alkyl moieties may be the same or different.

As used herein, a C$_{2-6}$ alkenyl group or moiety is a linear or branched alkenyl group or moiety one having at least one double bond of either E or Z stereochemistry where applicable and containing from 2 to 6 carbon atoms, for example a C$_{2-4}$ alkenyl group or moiety containing from 2 to 4 carbon atoms, such as —CH=CH$_2$ or —CH$_2$—CH=CH$_2$, —CH$_2$—CH$_2$—CH=CH$_2$, —CH$_2$—CH=CH—CH$_3$, —CH=C(CH$_3$)—CH$_3$ and —CH$_2$—C(CH$_3$)=CH$_2$. For the avoidance of doubt, where two alkenyl moieties are present in a group, they may be the same or different.

As used herein, a C$_{2-6}$-alkynyl group or moiety is a linear or branched-alkynyl group or moiety containing from 2 to 6 carbon atoms, for example a C$_{2-4}$ alkynyl group or moiety containing from 2 to 4 carbon atoms. Exemplary alkynyl groups include —C≡CH or —CH$_2$—C≡CH, as well as 1- and 2-butynyl, 2-methyl-2-propynyl, 2-pentynyl, 3-pentynyl, 4-pentynyl, 2-hexynyl, 3-hexynyl, 4-hexynyl and 5-hexynyl. For the avoidance of doubt, where two alkynyl moieties are present in a group, they may be the same or different.

As used herein, a C$_{1-6}$ alkylene group or moiety is a linear or branched alkylene group or moiety, for example a C$_{1-4}$ alkylene group or moiety. Examples include methylene, n-ethylene, n-propylene and —C(CH$_3$)$_2$— groups and moieties.

As used herein, a C$_{2-6}$ alkenylene group or moiety is a linear or branched alkenylene group or moiety, for example a C$_{2-4}$ alkenylene group or moiety. Examples include —CH=CH—, —CH=CH—CH$_2$—, —CH$_2$—CH=CH— and —CH=CH—CH=CH—.

As used herein, a C$_{2-6}$ alkynylene group or moiety is a linear or branched alkynylene group or moiety, for example a C$_{2-4}$ alkynylene group or moiety. Examples include —C≡C—, —C≡C—CH$_2$— and —CH$_2$—C≡C—.

As used herein, a halogen atom is typically chlorine, fluorine, bromine or iodine.

As used herein, a C$_{1-6}$ alkoxy group or C$_{2-6}$ alkenyloxy group is typically a said C$_{1-6}$ alkyl (e.g. a C$_{1-4}$ alkyl) group or a said C$_{2-6}$ alkenyl (e.g. a C$_{2-4}$ alkenyl) group respectively which is attached to an oxygen atom.

A haloalkyl, haloalkenyl, haloalkoxy or haloalkenyloxy group is typically a said alkyl, alkenyl, alkoxy or alkenyloxy group respectively which is substituted by one or more said halogen atoms. Typically, it is substituted by 1, 2 or 3 said halogen atoms. Preferred haloalkyl and haloalkoxy groups include perhaloalkyl and perhaloalkoxy groups such as —CX$_3$ and —OCX$_3$ wherein X is a said halogen atom, for example chlorine and fluorine.

As used herein, a C$_{1-4}$ alkylthio or C$_{2-4}$ alkenylthio group is typically a said C$_{1-4}$ alkyl group or a C$_{2-4}$ alkenyl group respectively which is attached to a sulphur atom, for example —S—CH$_3$.

As used herein, a C$_{1-4}$ hydroxyalkyl group is a C$_{1-4}$ alkyl group substituted by one or more hydroxy groups. Typically, it is substituted by one, two or three hydroxy groups. Preferably, it is substituted by a single hydroxy group.

When a phenyl ring is fused to a further phenyl, 5- to 10-membered heterocyclyl, C$_{3-7}$ carbocyclyl or 5- to 10-membered heterocyclyl group, it is preferably fused to a further phenyl, 5- to 6-membered heterocyclyl, C$_{3-7}$ carbocyclyl or 5- to 6-membered heterocyclyl group, more preferably to a 5- to 6-membered heteroaryl or 5- to 6-membered heterocyclyl group. Most preferably it is fused to a 5- to 6-membered heterocyclyl group. In this case, preferred 5- to 6-membered heterocyclyl groups include tetrahydrofuranyl, tetrahydrothienyl, pyrrolidinyl, dithiolanyl, dioxolanyl, oxazolidinyl, imidazolyl, isoxazolidinyl, imidazolidinyl, pyrazolidinyl, thioxolanyl, thiazolidinyl and isothiazolidinyl, more preferably oxazolidinyl, imidazolidinyl, thiazolidinyl, thioxolanyl, dioxolanyl and dithiolanyl, most preferably dioxolanyl.

As used herein, a 5- to 10-membered heteroaryl group or moiety is a monocyclic 5- to 10-membered aromatic ring, such as a 5- or 6-membered ring, containing at least one heteroatom, for example 1, 2, 3 or 4 heteroatoms, selected from O, S and N. When the ring contains 4 heteroatoms these are preferably all nitrogen atoms. Examples include thienyl, furyl, pyrrolyl, imidazolyl, thiazolyl, isothiazolyl, pyrazolyl, oxazolyl, isoxazolyl, triazolyl, thiadiazolyl, oxadiazolyl, pyridinyl, pyridazinyl, pyrimidinyl, pyrazinyl, triazinyl and tetrazolyl groups. Thienyl, pyrrolyl, imidazolyl, thiazolyl, isothiazolyl, pyrazolyl, oxazolyl, isoxazolyl, triazolyl, pyridinyl, pyridazinyl, pyrimidinyl and pyrazinyl groups are preferred, e.g. pyrrolyl, imidazolyl, thiazolyl, isothiazolyl, pyrazolyl, oxazolyl, isoxazolyl, triazolyl, pyridinyl, pyridazinyl, pyrimidinyl and pyrazinyl groups. More preferred groups are thienyl, pyridinyl, pyridazinyl, pyrimidinyl, pyrazinyl, pyrrolyl and triazinyl, e.g. pyridinyl, pyridazinyl, pyrimidinyl, pyrazinyl, pyrrolyl and triazinyl.

When a heteroaryl group or moiety is fused to another group, it may be fused to a further phenyl, 5- to 10-membered heteroaryl, 5- to 10-membered heterocyclyl or $C_{3-7}$ carbocyclyl group. Preferably it is preferably fused to a phenyl, 5- to 6-membered heteroaryl or 5- to 6-membered heterocyclyl ring, more preferably it is fused to a phenyl group. Examples include benzothienyl, benzofuryl, benzimidazolyl, benzothiazolyl, benzisothiazolyl, benzoxazolyl, benzisoxazolyl, benztriazolyl, indolyl, isoindolyl and indazolyl groups. Preferred groups include indolyl, isoindolyl, benzimidazolyl, indazolyl, benzofuryl, benzothienyl, benzoxazolyl, benzisoxazolyl, benzothiazolyl and benzisothiazolyl groups, more preferably benzimidazolyl, benzoxazolyl and benzothiazolyl, most preferably benzothiazolyl.

As used herein, a 5- to 10-membered heterocyclyl group or moiety is a non-aromatic, saturated or unsaturated $C_{5-10}$ carbocyclic ring in which one or more, for example 1, 2, 3 or 4, of the carbon atoms are replaced with a moiety selected from N, O, S, S(O) and S(O)$_2$, and wherein one or more of the remaining carbon atoms is optionally replaced by a group —C(O)— or —C(S)—. When one or more of the remaining carbon atoms is replaced by a group —C(O)— or —C(S)—, preferably only one or two (more preferably two) such carbon atoms are replaced. Typically, the 5- to 10-membered heterocyclyl ring is a 5- to 6-membered ring.

Suitable heterocyclyl groups and moieties include azetidinyl, oxetanyl, thietanyl, pyrrolidinyl, imidazolidinyl, oxazolidinyl, isoxazolidinyl, thiazolidinyl, isothiazolidinyl, tetrahydrofuranyl, tetrahydrothienyl, tetrahydropyranyl, tetrahydrothiopyranyl, dithiolanyl, dioxolanyl, pyrazolidinyl, piperidinyl, piperazinyl, hexahydropyrimidinyl, methylenedioxyphenyl, ethylenedioxyphenyl, thiomorpholinyl, S-oxo-thiomorpholinyl, S,S-dioxo-thiomorpholinyl, morpholinyl, 1,3-dioxolanyl, 1,4-dioxolanyl, trioxolanyl, trithianyl, imidazolinyl, pyranyl, pyrazolinyl, thioxolanyl, thioxothiazolidinyl, 1H-pyrazol-5-(4H)-onyl, 1,3,4-thiadiazol-2(3H)-thionyl, oxopyrrolidinyl, oxothiazolidinyl, oxopyrazolidinyl, succinimido and maleimido groups and moieties. Preferred heterocyclyl groups are pyrrolidinyl, imidazolidinyl, oxazolidinyl, isoxazolidinyl, thiazolidinyl, isothiazolidinyl, tetrahydrofuranyl, tetrahydrothienyl, tetrahydropyranyl, tetrahydrothiopyranyl, dithiolanyl, dioxolanyl, pyrazolidinyl, piperidinyl, piperazinyl, hexahydropyrimidinyl, thiomorpholinyl and morpholinyl groups and moieties. More preferred heterocyclyl groups are tetrahydropyranyl, tetrahydrothiopyranyl, thiomorpholinyl, tetrahydrofuranyl, tetrahydrothienyl, piperidinyl, morpholinyl and pyrrolidinyl groups, and variants where one or two ring carbon atoms are replaced with —C(O)— groups. Particularly preferred groups include tetrahydrofuranyl and pyrrolyl-2,5-dione.

When a heterocyclyl group or moiety is fused to another group, it may be fused to a further phenyl, 5- to 10-membered heteroaryl, 5- to 10-membered heterocyclyl or $C_{3-7}$ carbocyclyl group, more preferably to a further phenyl, 5- to 6-membered heteroaryl or 5- to 6-membered heterocyclyl group. Preferably it is monocyclic (i.e. it is unfused).

For the avoidance of doubt, although the above definitions of heteroaryl and heterocyclyl groups refer to an "N" moiety which can be present in the ring, as will be evident to a skilled chemist the N atom will be protonated (or will carry a substituent as defined below) if it is attached to each of the adjacent ring atoms via a single bond.

As used herein, a $C_{3-7}$ carbocyclic group or moiety is a non-aromatic saturated or unsaturated hydrocarbon ring having from 3 to 7 carbon atoms. Preferably it is a saturated or mono-unsaturated hydrocarbon ring (i.e. a cycloalkyl moiety or a cycloalkenyl moiety) having from 3 to 7 carbon atoms, more preferably having from 3 to 6 carbon atoms. Examples include cyclopropyl, cyclobutyl, cyclopentyl and cyclohexyl and their mono-unsaturated variants, more particularly cyclopentyl and cyclohexyl. A $C_{3-7}$ carbocyclyl group or moiety also includes $C_{3-7}$ carbocyclyl groups or moieties described above but wherein one or more ring carbon atoms are replaced by a group —C(O)—. More preferably one or two ring carbon atoms (most preferably two) are replaced by —C(O)—. A preferred such group is benzoquinone.

When a carbocyclyl group or moiety is fused to another group, it may be fused to a further phenyl, 5- to 10-membered heteroaryl, 5- to 10-membered heterocyclyl or $C_{3-7}$ carbocyclyl group, more preferably to a further phenyl, 5- to 6-membered heteroaryl or 5- to 6-membered heterocyclyl ring. For example it may be fused to a further phenyl ring. An exemplary fused carbocyclyl group is indanyl. More preferably carbocyclyl groups are monocyclic (i.e. non-fused).

Unless otherwise stated, the phenyl, heteroaryl, heterocyclyl and carbocyclyl moieties in $R^1$, $R^2$, $R^8$, $R^9$, A, Q, $Q^1$ and D are unsubstituted or substituted by 1, 2, 3 or 4 substituents which are the same or different and are selected from halogen atoms and $C_{1-4}$ alkyl, $C_{1-4}$ alkylene, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, mercapto, cyano, nitro, $C_{1-4}$ hydroxyalkyl, $C_{2-4}$ hydroxyalkenyl, $C_{1-4}$ alkylthio, $C_{2-4}$ alkenylthio, —NR'R" groups wherein each R' and R" is the same or different and represents hydrogen or $C_{1-4}$ alkyl, and groups of formula —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, SO$_2$NR$^A$R$^B$, —OCONH$_2$, —OCONHR$^A$, —OCONR$^A$R$^B$, —NHCOR$^A$, NHCOOR$^A$, —NR$^B$COOR$^A$, —NHSO$_2$OR$^A$, —NR$^B$SO$_2$OH, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$ and —NR$^A$CONR$^A$R$^B$ wherein R$^A$ and R$^B$ are the same or different and represent $C_{1-6}$ alkyl, non-fused $C_{3-6}$ cycloalkyl, non-fused phenyl or non-fused 5- to 6-membered heteroaryl, or R$^A$ and R$^B$ when attached to the same nitrogen atom form a non-fused 5- or 6-membered heterocyclyl group. Unless otherwise stated, the substituents are preferably themselves unsubstituted, in particular it is preferred that R$^A$ and R$^B$ are unsubstituted.

When the phenyl, heteroaryl, heterocyclyl and carbocyclyl moieties are substituted by two, three or four substituents, it is preferred that not more than two substituents are selected from $C_{1-4}$ alkylene, cyano and nitro. More preferably, not more than one substituent is selected from $C_{1-4}$ alkylene, cyano and nitro. Furthermore, when the phenyl, heteroaryl, heterocyclyl and carbocyclyl moieties are substituted by two or three substituents, it is preferred that not more than one substituent is selected from —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —OCONH$_2$, —OCONHR$^A$, —OCONR$^A$R$^B$, —NHCOR$^A$, NHCOOR$^A$, —NR$^B$COOR$^A$, —NHSO$_2$OR$^A$, —NR$^B$SO$_2$OH, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$ or —NR$^A$CONR$^A$R$^B$.

Typically the phenyl, heteroaryl, heterocyclyl and carbocyclyl moieties in $R^1$, $R^2$, $R^8$, $R^9$, A, Q, $Q^1$ and D are unsubstituted or substituted by 1, 2, 3 or 4 substituents, for example by 1, 2 or 3 substituents. Preferred substituents include halogen atoms and $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, mercapto, cyano, nitro, $C_{1-4}$ hydroxyalkyl, $C_{2-4}$ hydroxyalkenyl, $C_{1-4}$ alkylthio, $C_{2-4}$ alkenylthio and —NR'R" groups wherein each R' and R" is the same or different and represents hydrogen or $C_{1-4}$ alkyl, and groups of formula $COR^A$, —$SO_2R^A$, —$CONH_2$, —$SO_2NH_2$, —$CONHR^A$, —$SO_2NHR^A$, —$CONR^AR^B$ and —$SO_2NR^AR^B$ wherein $R^A$ and $R^B$ are the same or different and represent $C_{1-4}$ alkyl. Preferably the substituents are themselves unsubstituted.

More preferred substituents on the phenyl, heteroaryl, heterocyclyl and carbocyclyl moieties in $R^1$, $R^2$, $R^8$, $R^9$, A, Q, $Q^1$ and D include halogen atoms and $C_{1-4}$ alkyl, $C_{1-4}$ alkoxy, $C_{1-4}$ alkylthio, $C_{1-4}$ haloalkyl, hydroxyl, cyano, nitro and —NR'R'' groups wherein each R' and R'' is the same or different and represents hydrogen or $C_{1-4}$ alkyl, and groups of formula $COR^A$, —$SO_2R^A$, —$CONH_2$, —$SO_2NH_2$, —$CONHR^A$, —$SO_2NHR^A$, —$CONR^AR^B$ and —$SO_2NR^AR^B$ wherein $R^A$ and $R^B$ are the same or different and represent $C_{1-2}$ alkyl. More preferred substituents include halogen atoms and $C_{1-4}$ alkyl, $C_{1-4}$ alkoxy, $C_{1-4}$ alkylthio and hydroxyl groups. More preferred substituents include halogen atoms, $C_{1-4}$ alkyl, $C_{1-2}$ alkoxy, $C_{1-2}$ alkylthio and hydroxy.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like.

Compounds of the invention which contain one or more actual or potential chiral centres, because of the presence of asymmetric carbon atoms, can exist as a number of diastereoisomers with R or S stereochemistry at each chiral centre. The invention includes all such diastereoisomers and mixtures thereof.

The term "ester" or "esterified carboxyl group" in connection with substituent $R^7$ above means a group —(C═O)$OR^{11}$ in which $R^{11}$ is the group characterising the ester, notionally derived from the alcohol $R^{11}$—OH.

Group $R^1$

Preferably $R^1$ represents a hydrogen or halogen atom, or an unsubstituted $C_{1-4}$ alkyl, hydroxyl, $C_{1-4}$ alkoxy, mercapto, $C_{1-4}$ alkylthio, —NR'R'' or —$CONR^AR^B$ group where R', R'', $R^A$ and $R^B$ are the same or different and represent hydrogen or unsubstituted $C_{1-4}$ alkyl group. More preferably $R^1$ represents a halogen atom (preferably chlorine) or an unsubstituted $C_{1-4}$ alkyl or —NR'R'' group wherein R' and R'' are the same or different and represent hydrogen or unsubstituted $C_{1-2}$ alkyl. More preferably still, $R^1$ represents an —NR'R'' group wherein R' and R'' are the same or different and represent hydrogen or $C_{1-2}$ alkyl. Most preferably $R^1$ represents —$NH_2$.

It is preferred that the alkyl groups and moieties in $R^1$ are unsubstituted or substituted by 1, 2 or 3 substituents which are themselves unsubstituted and are selected from halogen, $C_{1-4}$ alkyl, $C_{2-4}$ alkenyl, $C_{1-4}$ alkoxy, hydroxyl, $C_{1-4}$ haloalkyl, $C_{2-4}$ haloalkenyl, $C_{1-4}$ haloalkyloxy, $C_{2-4}$ haloalkenyloxy and —NR'R'' wherein R' and R'' are the same or different and represent hydrogen or $C_{1-2}$ alkyl. More preferably, the alkyl groups and moieties in $R^1$ are unsubstituted or substituted by 1 or 2 unsubstituted substituents selected from halogen, $C_{1-2}$ alkoxy, $C_{1-2}$ haloalkyl, hydroxyl and —NR'R'' wherein R' and R'' are the same or different and represent hydrogen or $C_{1-2}$ alkyl. In particular, it is preferred that R' and R'' are unsubstituted. More preferably, the alkyl groups and moieties in $R^1$ are unsubstituted.

Group $R^2$

Preferably $R^2$ represents a hydrogen or halogen atom, an unsubstituted $C_{1-4}$ alkyl group or a group of formula —NR'R'' where R' and R'' are the same or different and represent hydrogen or unsubstituted $C_{1-2}$ alkyl. More preferably $R^2$ represents a hydrogen or halogen atom (preferably fluorine or chlorine) or an —$NH_2$ group. Most preferably $R^2$ represents a hydrogen atom.

Group -$(L^1)_x$-$(Het)_y$- x and y are the same or different and represent zero or 1. When x is zero, $L^1$ is absent, and when y is 0, Het is absent. Preferably at least one of x and y is 1. More preferably only one of x and y is 1. In a most preferred embodiment, x is zero and y is 1.

When present, $L^1$ preferably represents unsubstituted $C_{1-4}$ alkylene, more preferably unsubstituted $C_{1-2}$ alkylene, most preferably —$CH_2$—.

When present, Het preferably represents —S—, —S(O)— or —$S(O)_2$—. More preferably, Het represents —S— or —S(O)—. Most preferably Het represents —S—.

Group A

Preferably A represents an unsubstituted or substituted phenyl, 5- to 6-membered heteroaryl, $C_{3-7}$ carbocyclyl or 5- to 6-membered heterocyclyl group which is optionally fused to a further phenyl, 5- to 6-membered heteroaryl, $C_{3-7}$ carbocyclyl or 5- to 6-membered heterocyclyl group. More preferably A represents an unsubstituted or substituted phenyl, 5- to 6-membered heteroaryl, $C_{3-7}$ carbocyclyl or 5- to 6-membered heterocyclyl group which is optionally fused to a further phenyl, 5- to 6-membered heteroaryl or 5- to 6-membered heterocyclyl group. More preferably A represents an unsubstituted or substituted non-fused phenyl, non-fused 5- to 6-membered heteroaryl, non-fused $C_{3-7}$ carbocyclyl, non-fused 5- to 6-membered heterocyclyl group, a phenyl group which is fused to a further 5- to 6-membered heterocyclyl group, or a 5- to 6-membered heteroaryl group which is fused to a further phenyl group.

When A represents a phenyl group which is fused to a further 5- to 6-membered heterocyclyl group, preferred 5- to 6-membered heterocyclyl groups include tetrahydrofuranyl, tetrahydrothienyl, pyrrolidinyl, dithiolanyl, dioxolanyl, oxazolidinyl, imidazolidinyl, isoxazolidinyl, imidazolidinyl, pyrazolidinyl, thioxolanyl, thiazolidinyl and isothiazolidinyl, more preferably oxazolidinyl, imidazolidinyl, thiazolidinyl, thioxolanyl, dioxolanyl and dithiolanyl, most preferably dioxolanyl.

When A represents a non-fused 5- to 6-membered heteroaryl group, preferred groups include pyrrolyl, furanyl, thienyl, pyridinyl, pyridazinyl, pyrimidinyl, pyrazinyl and triazinyl.

When A is a 5- to 6-membered heteroaryl group fused to a phenyl group, preferred groups include indolyl, isoindolyl, benzimidazolyl, indazolyl, benzofuryl, benzothienyl, benzoxazolyl, benzisoxazolyl, benzothiazolyl, benzisothiazolyl, more preferably benzimidazolyl, benzoxazolyl or benzothiazolyl, most preferably benzothiazolyl.

When A represents a non-fused 5- to 6-membered heterocyclyl group, suitable groups include 5- to 6-membered heterocyclyl groups where 1, 2, 3 or 4, of the carbon atoms are replaced with a moiety selected from N, O, S, S(O) and $S(O)_2$, and wherein one or more of the remaining carbon atoms is optionally replaced by a group —C(O)— or —C(S)—. When one or more of the remaining carbon atoms is replaced by a group —C(O)— or —C(S)—, preferably only one or two (more preferably two) such carbon atoms are replaced. More preferably two of the carbon atoms of the heterocyclyl group are replaced by —C(O)— groups. Thus, suitable 5- to 6-membered heterocyclyl groups include tetrahydrofuranyl, pyrrolidinyl, tetrahydrothienyl, piperidinyl, tetrahydropyranyl, tetrahydrothiopyranyl, morpholinyl and thiomorpholinyl, and variants where one or two of the ring carbon atoms are replaced with —C(O)— groups. Particularly preferred 5- to 6-membered heterocyclyl groups include tetrahydrofuranyl and pyrrolyl-2,5-dione.

When A is a non-fused $C_{3-7}$ carbocyclyl group, preferred groups include $C_{3-7}$ carbocyclyl groups wherein one or two ring carbon atoms are replaced by —C(O)— or —S(O)—, more preferably wherein two ring-carbon atoms are replaced by —C(O)—. More preferably, when A is a non-fused $C_{3-7}$ carbocyclyl group it is a benzoquinone group.

In a most preferred embodiment, A represents an unsubstituted or substituted phenyl ring, wherein the phenyl ring is optionally fused to a further phenyl, 5- to 6-membered heteroaryl or 5- to 6-membered heterocyclyl group. When A is fused, it is preferably fused to a further 5- to 6-membered heterocyclyl group, more preferably to an imidazolidinyl, thiazolidinyl, thioxolanyl, dioxolanyl or dithiolanyl group, most preferably to a dioxolanyl group.

Preferably group A is unsubstituted or substituted by 1, 2, 3 or 4 substituents which are themselves unsubstituted, which are the same or different, and which are selected from halogen atoms and $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, mercapto, cyano, nitro, $C_{1-4}$ hydroxyalkyl, $C_{2-4}$ hydroxyalkenyl, $C_{1-4}$ alkylthio, $C_{2-4}$ alkenylthio and —NR'R" groups wherein each R' and R" is the same or different and represents hydrogen or $C_{1-4}$ alkyl, and groups of formula $COR^A$, —$SO_2R^A$, —$CONH_2$, —$SO_2NH_2$, —$CONHR^A$, —$SO_2NHR^A$, —$CONR^AR^B$ and —$SO_2NR^AR^B$ wherein $R^A$ and $R^B$ are the same or different and represent $C_{1-4}$ alkyl. More preferred substituents on group A include 1, 2, 3 or 4 unsubstituted substituents which are the same or different and represent halogen atoms and $C_{1-4}$ alkyl, $C_{1-4}$ alkoxy, $C_{1-4}$ alkylthio, $C_{1-4}$ haloalkyl, hydroxyl, cyano, nitro and —NR'R" groups wherein each R' and R" is the same or different and represents hydrogen or $C_{1-4}$ alkyl. Even more preferred substituents include halogen atoms, $C_{1-4}$ alkyl, $C_{1-2}$ alkoxy, $C_{1-2}$ alkylthio and hydroxy. Preferred halogen substituents include fluorine, chlorine, bromine and iodine atoms, most preferably iodine atoms. Preferred $C_{1-2}$ alkoxy substituents include methoxy groups. Preferred $C_{1-4}$ alkyl substituents include methyl, ethyl and propyl, more preferably ethyl and propyl. Preferred $C_{1-2}$ alkylthio substituents include —S—$CH_3$. In a most preferred embodiment, group A is substituted by a single iodine atom.

Group W

W is a group of formula —[$CH_2$], —$Y^1$-$L^2$-R. The group W contains the alpha amino acid or alpha amino acid ester moiety of formula (X) or (Y) linked through a linker radical to the purinyl ring system. Where W terminates in an ester group, the compounds of the invention are converted by intracellular esterases to the corresponding carboxylic acid. Both the esters and carboxylic acids may have HSP90 inhibitory activity in their own right. The compounds of the invention therefore include not only the ester, but also the corresponding carboxylic acid hydrolysis products.

Group R

The group R has one of formulae (X) or (Y):

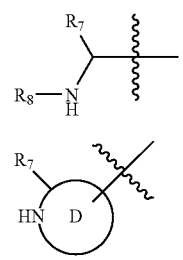

Group $R^7$ $R^7$ is either a carboxylic acid group —COOH or an ester group —$COOR^{11}$. Where $R^7$ is an ester group, it must be one which in the compound of the invention is hydrolysable by one or more intracellular carboxylesterase enzymes to a carboxylic acid group. Intracellular carboxylesterase enzymes capable of hydrolysing the ester group of a compound of the invention to the corresponding acid include the three known human enzyme isotypes hCE-1, hCE-2 and hCE-3. Although these are considered to be the main enzymes other enzymes such as biphenylhydrolase (BPH) may also have a role in hydrolysing the conjugates. In general, if the carboxylesterase hydrolyses the free amino acid ester to the parent acid it will also hydrolyse the ester motif when covalently conjugated to the modulator. Hence, the broken cell assay described later provides a straightforward, quick and simple first screen for esters which have the required hydrolysis profile. Ester motifs selected in that way may then be re-assayed in the same carboxylesterase assay when conjugated to the HSP90 inhibitor via the chosen conjugation chemistry, to confirm that it is still a carboxylesterase substrate in that background.

Subject to the requirement that they be hydrolysable by intracellular carboxylesterase enzymes, examples of particular ester groups $R^7$ include those of formula —(C=O)$OR^{11}$ wherein $R^{11}$ is —$CR^{12}R^{13}R^{14}$ wherein:

(i) $R^{13}$ represents hydrogen or a group of formula —[$C_{1-4}$ alkylene]$_b$-($Z^1$)$_a$-[$C_{1-4}$ alkyl] or —[$C_{1-4}$ alkylene]$_b$-($Z^1$)$_a$-[$C_{2-4}$ alkenyl] wherein a and b are the same or different and represent 0 or 1, and $Z^1$ represents —O—, —S—, or —$NR^{17}$— wherein $R^{17}$ is hydrogen or $C_{1-4}$ alkyl, $R^{14}$ represents hydrogen or $C_{1-4}$ alkyl, and $R^{12}$ represents hydrogen or $C_{1-4}$ alkyl;

(ii) $R^{13}$ represents a phenyl or a 5- to 10-membered heteroaryl group optionally fused to a further phenyl, 5- to 10-membered heteroaryl, $C_{3-7}$ carbocyclyl or 5- to 10-membered heterocyclyl group, $R^{14}$ represents hydrogen or $C_{1-4}$ alkyl, and $R^{12}$ represents hydrogen;

(iii) $R^{13}$ represents a group of formula -(Alk$^3$)—$NR^{15}R^{16}$ wherein Alk$^3$ represents a $C_{1-4}$ alkylene group and either (a) $R^{15}$ and $R^{16}$ are the same or different and represent hydrogen or $C_{1-4}$ alkyl, or (b) $R^{15}$ and $R^{16}$, together with the nitrogen atom to which they are bonded, form a 5- to 10-membered heteroaryl or 5- to 10-membered heterocyclyl group optionally fused to a further phenyl, 5- to 10-membered heteroaryl, $C_{3-7}$ carbocyclyl or 5- to 10-membered heterocyclyl group; $R^{14}$ represents hydrogen or $C_{1-4}$ alkyl, and $R^{12}$ represents hydrogen; or (iv) $R^{13}$ and $R^{14}$, together with the carbon atom to which they are bonded, form a phenyl, 5- to 10-membered heteroaryl, $C_{3-7}$ carbocyclyl or 5- to 10-membered heterocyclyl group which is optionally fused to a further phenyl, 5- to 10-membered heteroaryl, $C_{3-7}$ carbocyclyl or 5- to 10-membered heterocyclyl group, and $R^{12}$ represents hydrogen.

Preferred substituents on the alkyl, alkylene and alkenyl groups in $R^{12}$, $R^{13}$, $R^{14}$, $R^{15}$, $R^{16}$, $R^{17}$ and Alk$^3$ groups include one or two substituents which are the same or different and are selected from halogen, $C_{1-4}$ alkyl, $C_{2-4}$ alkenyl, $C_{1-4}$ alkoxy, hydroxyl and —NR'R" wherein R' and R" are the same or different and represent hydrogen or $C_{1-2}$ alkyl. More preferred substituents are halogen, $C_{1-2}$ alkoxy, hydroxyl and —NR'R" wherein R' and R" are the same or different and represent hydrogen or $C_{1-2}$ alkyl. Most preferably the alkyl, alkylene and alkenyl groups in $R^{13}$, $R^{14}$ and Alk$^3$ are unsubstituted.

Preferred substituents on the phenyl, heteroaryl, carbocyclyl and heterocyclyl groups in or formed by $R^{13}$, $R^{14}$, $R^{15}$ and $R^{16}$ groups include one or two substituents which are the same or different and are selected from halogen atoms and $C_{1-4}$ alkyl, $C_{1-4}$ alkylene, $C_{1-4}$ alkoxy, $C_{1-4}$ haloalkyl, hydroxyl, cyano, nitro and —NR'R" groups wherein each R' and R" is the same or different and represents hydrogen or $C_{1-4}$ alkyl, more preferably halogen atoms and $C_{1-2}$ alkyl, $C_{1-2}$ alkylene, $C_{1-2}$ alkoxy and hydroxyl groups. More preferably the phenyl, heteroaryl, carbocyclyl and heterocyclyl groups in or formed by $R^{13}$, $R^{14}$, $R^{15}$ and $R^{16}$ are unsubstituted or substituted by a $C_{1-2}$ alkylene group, in particular a methylene group. Most preferably the phenyl, heteroaryl, carbocyclyl and heterocyclyl groups in or formed by $R^{13}$, $R^{14}$, $R^{15}$, $R^{16}$ are unsubstituted.

When $R^{13}$ represents a group of formula —[$C_{1-4}$ alkylene]$_b$-($Z^1$)$_a$-[$C_{1-4}$ alkyl], preferably either a or b is zero, for example both a and b are zero. When [$C_{1-4}$ alkylene] is present, it is preferably a $C_{1-3}$ alkylene, more preferably a $C_{1-2}$ alkylene such as a group —CH$_2$—CH$_2$—.

When $R^{13}$ represents a group of formula —[$C_{1-4}$ alkylene]$_b$-($Z^1$)$_a$-[$C_{1-4}$ alkyl], preferably $C_{1-4}$ alkyl is a $C_{1-3}$ alkyl group such as methyl, ethyl or n-propyl, most preferably methyl.

When $R^{13}$ represents a group of formula —[$C_{1-4}$ alkylene]$_b$-($Z^1$)$_a$-[$C_{1-4}$ alkyl] and a is 1, $Z^1$ is preferably —O— or —NR$^{17}$— wherein R$^{17}$ is hydrogen or $C_{1-2}$ alkyl, more preferably Z, is —O—.

When $R^{13}$ represents a group of formula —[$C_{1-4}$ alkylene]$_b$-($Z^1$)$_a$-[$C_{2-4}$ alkenyl], preferably either a or b is zero, more preferably both a and b are zero. When [$C_{1-4}$ alkylene] is present, it is preferably a $C_{1-3}$ alkylene, more preferably a $C_{1-2}$ alkylene.

When $R^{13}$ represents a group of formula —[$C_{1-4}$ alkylene]$_b$-($Z^1$)$_a$-[$C_{2-4}$ alkenyl], preferably $C_{2-4}$ alkenyl is a $C_{2-3}$ alkenyl group, in particular —CH=CH$_2$.

When $R^{13}$ represents a group of formula —[$C_{1-4}$ alkylene]$_b$-($Z^1$)$_a$-[$C_{1-4}$ alkenyl] and a is 1, $Z^1$ is preferably —O— or —NR$^{17}$— wherein R$^{17}$ is hydrogen or $C_{1-2}$ alkyl, more preferably $Z^1$ is —O—. Most preferably $Z^1$ is absent (i.e. a is zero).

When $R^{13}$ represents hydrogen or a group of formula —[$C_{1-4}$ alkylene]$_b$-($Z^1$)$_a$-[$C_{1-4}$ alkyl] or —[$C_{1-4}$ alkylene]$_b$-($Z^1$)$_a$-[$C_{2-4}$ alkenyl], preferably $R^{13}$ represents hydrogen or a $C_{1-4}$ alkyl or $C_{2-4}$ alkenyl group, or a group —($C_{1-4}$ alkyl)-O—($C_{1-4}$ alkyl). More preferably $R^{13}$ represents hydrogen, methyl, ethyl, n-propyl, —CH=CH$_2$ or —CH$_2$—CH$_2$—O—CH$_3$, most preferably methyl.

When $R^{13}$ represents hydrogen or a group of formula —[$C_{1-4}$ alkylene]$_b$-($Z^1$)$_a$-[$C_{1-4}$ alkyl] or —[$C_{1-4}$ alkylene]$_b$-($Z^1$)$_a$-[$C_{2-4}$ alkenyl], preferably $R^{14}$ represents hydrogen or $C_{1-2}$ alkyl, more preferably hydrogen or methyl.

When $R^{13}$ represents hydrogen or a group of formula —[$C_{1-4}$ alkylene]$_b$-($Z^1$)$_a$-[$C_{1-4}$ alkyl] or —[$C_{1-4}$ alkylene]$_b$-($Z^1$)$_a$-[$C_{2-4}$ alkenyl], preferably $R^{12}$ represents hydrogen or $C_{1-2}$ alkyl, more preferably $R^{12}$ represents hydrogen or methyl.

When $R^{13}$ represents hydrogen or a group of formula —[$C_{1-4}$ alkylene]$_b$-($Z^1$)$_a$-[$C_{1-4}$ alkyl] or —[$C_{1-4}$ alkylene]$_b$-($Z^1$)$_a$-[$C_{2-4}$ alkenyl], preferably the alkyl, alkylene and alkenyl groups in both $R^{13}$ and $R^{14}$ are unsubstituted.

When $R^{13}$ represents a phenyl or a 5- to 10-membered heteroaryl group optionally fused to a further phenyl, 5- to 10-membered heteroaryl, $C_{3-7}$ carbocyclyl or 5- to 10-membered heterocyclyl group, preferably it represents a non-fused phenyl or a non-fused 5- to 6-membered heteroaryl group. Preferred heteroaryl groups include pyridyl, pyrrolyl, isothiazolyl, pyrazolyl and isoxazolyl, most preferably pyridyl.

When $R^{13}$ represents a phenyl or a 5- to 10-membered heteroaryl group optionally fused to a further phenyl, 5- to 10-membered heteroaryl, $C_{3-7}$ carbocyclyl or 5- to 10-membered heterocyclyl group, preferably the phenyl, heteroaryl, carbocyclyl and heterocyclyl groups in $R^{13}$ are unsubstituted.

When $R^{13}$ represents a phenyl or a 5- to 10-membered heteroaryl group optionally fused to a further phenyl, 5- to 10-membered heteroaryl, $C_{3-7}$ carbocyclyl or 5- to 10-membered heterocyclyl group, $R^{14}$ preferably represents hydrogen or $C_{1-4}$ alkyl, more preferably hydrogen or $C_{1-2}$ alkyl, most preferably hydrogen. Preferably the $C_{1-4}$ alkyl groups of $R^{14}$ are unsubstituted.

When $R^{13}$ represents a group of formula -(Alk$^3$)—NR$^{15}$R$^{16}$, Alk$^3$ preferably represents a $C_{1-2}$ alkylene group, preferably either —CH$_2$— or —CH$_2$CH$_2$—.

When $R^{13}$ represents a group of formula -(Alk$^3$)—NR$^{15}$R$^{16}$ and R$^{15}$ and R$^{16}$ are the same or different and represent hydrogen or $C_{1-4}$ alkyl, preferably $R^{15}$ represents hydrogen or $C_{1-2}$ alkyl, more preferably $R^{15}$ represents a methyl group. When $R^{13}$ represents a group of formula -(Alk$^3$)—NR$^{15}$R$^{16}$ and R$^{15}$ and R$^{16}$ are the same or different and represent hydrogen or $C_{1-4}$ alkyl, preferably $R^{16}$ represents hydrogen or $C_{1-2}$ alkyl, more preferably $R^{16}$ represents a methyl group.

When $R^{13}$ represents a group of formula -(Alk$^3$)—NR$^{15}$R$^{16}$ and R$^{15}$ and R$^{16}$, together with the nitrogen atom to which they are bonded, form a 5- to 10-membered heteroaryl or 5- to 10-membered heterocyclyl group optionally fused to a further phenyl, 5- to 10-membered heteroaryl, $C_{3-7}$ carbocyclyl or 5- to 10-membered heterocyclyl group, preferably they form a non-fused 5- to 6-membered heteroaryl or non-fused 5- to 6-membered heterocyclyl group. More preferably they form a 5- to 6-membered heterocyclyl group. Preferred heterocyclyl groups include piperidinyl, piperazinyl, morpholinyl and pyrrolidinyl, most preferably morpholinyl.

When $R^{13}$ represents a group of formula -(Alk$^3$)—NR$^{15}$R$^{16}$, Alk$^3$ preferably represents a $C_{1-2}$ alkylene group, more preferably a group —CH$_2$CH$_2$—.

When $R^{13}$ represents a group of formula -(Alk$^3$)—NR$^{15}$R$^{16}$, $R^{14}$ preferably represents hydrogen or $C_{1-2}$ alkyl, most preferably hydrogen.

When $R^{13}$ represents a group of formula -(Alk$^3$)—NR$^{15}$R$^{16}$, preferably the alkyl and alkylene groups in Alk$^3$, R$^{15}$ and R$^{16}$ are unsubstituted. When $R^{13}$ represents a group of formula -(Alk$^3$)—NR$^{15}$R$^{16}$, preferably the phenyl, heteroaryl, carbocyclyl and heterocyclyl groups in R$^{15}$ and R$^{16}$ are unsubstituted.

When $R^{13}$ represents a group of formula -(Alk$^3$)—NR$^{15}$R$^{16}$, preferred groups include —CH$_2$—CH$_2$—NMe$_2$ and —CH$_2$—CH$_2$-morpholinyl.

When $R^{13}$ and $R^{14}$, together with the carbon atom to which they are bonded, form a phenyl, 5- to 10-membered heteroaryl, $C_{3-7}$ carbocyclyl or 5- to 10-membered heterocyclyl group which is optionally fused to a further phenyl, 5- to 10-membered heteroaryl, $C_{3-7}$ carbocyclyl or 5- to 10-membered-heterocyclyl group, preferred groups include non-fused phenyl, non-fused 5- to 6-membered heteroaryl, non-fused 5- to 6-membered heterocyclyl, non-fused $C_{3-7}$ carbocyclyl and $C_{3-7}$ carbocyclyl fused to a phenyl ring, more preferably non-fused phenyl, non-fused 5- to 6-membered heterocyclyl, non-fused $C_{3-7}$ carbocyclyl and $C_{3-7}$ carbocyclyl fused to a phenyl ring.

When $R^{13}$ and $R^{14}$ form a cyclic group together with the carbon atom to which they are bonded, preferred non-fused 5- to 6-membered heterocyclyl groups include piperidinyl, tetrahydrofuranyl, piperazinyl, morpholinyl and pyrrolidinyl groups, more preferably piperidinyl and tetrahydrofuranyl groups. When $R^{13}$ and $R^{14}$ form a cyclic group together with the carbon atom to which they are bonded, preferred non-fused $C_{3-7}$ carbocyclyl groups include cyclopentyl and cyclohexyl, more preferably cyclopentyl. When $R^{13}$ and $R^{14}$ form a cyclic group together with the carbon atom to which they are bonded, preferred $C_{3-7}$ carbocyclyl groups fused to a phenyl ring include indanyl.

When $R^{13}$ and $R^{14}$ form a cyclic group together with the carbon atom to which they are bonded, preferably the phenyl, heteroaryl, carbocyclyl and heterocyclyl groups formed are unsubstituted or substituted by one or two substituents which are the same or different and are selected from halogen atoms and $C_{1-4}$ alkyl, $C_{1-4}$ alkylene, $C_{1-4}$ alkoxy, $C_{1-4}$ haloalkyl, hydroxyl, cyano, nitro and —NR'R" groups wherein each R' and R" is the same or different and represents hydrogen or $C_{1-4}$ alkyl, more preferably selected from halogen atoms or $C_{1-2}$ alkyl, $C_{1-2}$ alkylene, $C_{1-2}$ alkoxy and hydroxyl groups. Most preferably the phenyl, heteroaryl, carbocyclyl and heterocyclyl groups formed are unsubstituted or substituted by a $C_{1-2}$ alkyl group (such as a methyl group) or by a $C_{1-2}$ alkylene group (such as by a methylene group). Even more preferably the phenyl, heteroaryl, carbocyclyl and heterocyclyl groups so formed are unsubstituted.

Particularly preferred $R^{11}$ groups include $C_{1-4}$ alkyl groups (such as methyl, ethyl, n- or iso-propyl and n-, sec- and tert-butyl), $C_{3-7}$ carbocyclyl groups (such as cyclopentyl and cyclohexyl), $C_{2-4}$ alkenyl groups (such as allyl), and also phenyl, benzyl, 2-pyridylmethyl, 3-pyridylmethyl, 4-pyridylmethyl, N-methylpiperidin-4-yl, tetrahydrofuran-3-yl, methoxyethyl, indanyl, norbonyl, dimethylaminoethyl and morpholinoethyl groups, more preferably $R^{11}$ represents $C_{1-4}$ alkyl or $C_{3-7}$ carbocyclyl. Most preferred groups include where $R^{11}$ is cyclopentyl or t-butyl, more preferably where $R^{11}$ is cyclopentyl.

Compound where $R^7$ represents —COOH or —COOR$^{11}$ wherein $R^{11}$ is $C_{1-4}$ alkyl or $C_{3-7}$ carbocyclyl can be described by a group where $R^7$ is —COOR$^{18}$ and $R^{18}$ is hydrogen, $C_{1-4}$ alkyl or $C_{3-7}$ carbocyclyl. Preferably $R^7$ is —COOR$^{18}$ where $R^{18}$ is hydrogen or $C_{3-7}$ carbocyclyl, more preferably where $R^{18}$ is hydrogen or cyclopentyl.

Group $R^8$

The group $R^8$ is present in the compounds of the invention when R in substituent W is a radical of formula (X).

$R^8$ preferably represents hydrogen or a $C_{1-6}$ alkyl, —(C=O)R$^9$ or —(C=O)OR$^{10}$ wherein $R^9$ and $R^{10}$ are as defined above, or $R^8$ represents a non-fused phenyl, non-fused 5- to 6-membered heteroaryl, non-fused $C_{3-7}$ carbocyclyl or non-fused 5- to 6-membered heterocyclyl group. More preferably $R^8$ preferably represents hydrogen or a $C_{1-6}$ alkyl, —(C=O)R$^9$ or —(C=O)OR$^{10}$ wherein $R^9$ and $R^{10}$ are as defined above, or $R^8$ represents a non-fused phenyl, non-fused 5- to 6-membered heteroaryl or a non-fused $C_{3-7}$ carbocyclyl group.

When $R^8$ represents a $C_{1-6}$ alkyl group, it is preferably a $C_{1-4}$ alkyl group such as methyl, ethyl or n- or iso-propyl.

When $R^8$ represents a $C_{3-7}$ carbocyclyl group, it is preferably a $C_{3-6}$ carbocyclyl group, more preferably a $C_{3-6}$ cycloalkyl group such as cyclopropyl, cyclopentyl or cyclohexyl.

When $R^8$ represents a 5- to 6-membered heteroaryl group preferred groups include pyridyl.

When $R^8$ represents —(C=O)R$^9$, preferably $R^9$ is $C_{1-6}$ alkyl, non-fused phenyl, non-fused 5- to 6-membered heteroaryl, non-fused $C_{3-7}$ carbocyclyl or a group -Alk$^4$-Cyc. When $R^9$ is $C_{1-6}$ alkyl, it is preferably a $C_{1-4}$ alkyl group such as methyl, ethyl, n- or iso-propyl, or n-, iso- or sec-butyl. When $R^9$ is $C_{3-7}$ carbocyclyl it is preferably $C_{3-6}$ carbocyclyl, more preferably $C_{3-6}$ cycloalkyl such as cyclopropyl, cyclopentyl or cyclohexyl. When $R^9$ is 5- to 6-membered heteroaryl, preferred groups include pyridyl and thienyl. When $R^9$ is -Alk$^4$-Cyc, Alk$^4$ is preferably a $C_{1-4}$ alkylene group, more preferably $C_{1-2}$ alkylene, most preferably methylene. When $R^9$ is -Alk$^4$-Cyc, Cyc is preferably a non-fused phenyl, a non-fused 5- to 6-membered heteroaryl or a non-fused 5- to 6-membered heterocyclyl group. When Cyc is a 5- to 6-membered heteroaryl it is preferably thienyl or pyridyl. Preferred -Alk$^4$-Cyc groups include benzyl, 4-methoxyphenylmethylcarbonyl, thienylmethyl and pyridylmethyl.

When $R^8$ represents —(C=O)OR$^{10}$ or —(C=O)NHR$^{10}$, preferably $R^{10}$ is hydrogen or $C_{1-4}$ alkyl, more preferably hydrogen, methyl, ethyl, or n- or iso-propyl.

The alkyl and alkylene groups in $R^8$, $R^9$, $R^{10}$ and Alk$^4$ are preferably unsubstituted or substituted by 1 or 2 substituents which are the same or different and are selected from halogen, $C_{1-4}$ alkyl, $C_{2-4}$ alkenyl, $C_{1-4}$ alkoxy, hydroxyl and —NR'R" wherein R' and R" are the same or different and represent hydrogen or $C_{1-2}$ alkyl, more preferably selected from halogen, $C_{1-2}$ alkoxy, hydroxyl and —NR'R" wherein R' and R" are the same or different and represent hydrogen or $C_{1-2}$ alkyl. Most preferably the alkyl and alkylene groups in $R^8$, $R^9$, $R^{10}$ and Alk$^4$ are unsubstituted.

The phenyl, heteroaryl, heterocyclyl, carbocyclyl and heterocyclyl in $R^8$ and $R^9$ are preferably unsubstituted or substituted by one or two substituents which are the same or different and are selected from halogen atoms and $C_{1-4}$ alkyl, $C_{1-4}$ alkoxy, $C_{1-4}$ haloalkyl, hydroxyl, cyano, nitro and —NR'R" groups wherein each R' and R" is the same or different and represents hydrogen or $C_{1-4}$ alkyl, more preferably the substituents are selected from halogen atoms and $C_{1-2}$ alkyl, $C_{1-2}$ alkoxy and hydroxyl groups. Most preferably the phenyl, heteroaryl, carbocyclyl and heterocyclyl groups in $R^8$ are unsubstituted. Most preferably the phenyl, heteroaryl, carbocyclyl and heterocyclyl groups in $R^9$ are unsubstituted or substituted by a single $C_{1-2}$ alkoxy group, more preferably by a single methoxy group.

In a most preferred embodiment, $R^8$ is hydrogen.

For compounds of the invention which are to be administered systemically, esters with a slow rate of esterase cleavage are preferred, since they are less susceptible to pre-systemic metabolism. Their ability to reach their target tissue intact is therefore increased, and the ester can be converted inside the cells of the target tissue into the acid product. However, for local administration, where the ester is either directly applied to the target tissue or directed there by, for example, inhalation, it will often be desirable that the ester has a rapid rate of esterase cleavage, to minimise systemic exposure and consequent unwanted side effects. If a carbon atom to which the group R is attached is unsubstituted, i.e. R is attached to a methylene (—$CH_2$—) radical, then the esters tend to be cleaved more rapidly than if that carbon is substituted, or is part of a ring system such as a phenyl or cyclohexyl ring. Thus, if (i) p is 1 and $Alk^2$ terminates in a methylene radical, (ii) n and p are both zero, m is 1 and $Alk^1$ terminates in a methylene radical, or (iii) m, n and p are zero, $Y^1$ is a bond and z is 1, then the ester (i.e. when $R^7$ is not —COOH) is likely to be cleaved more rapidly.

Group —$[CH_2]_z$—$Y^1$-$L^2$-

The group (or bond, when m, n, p and z are zero and $Y^1$ represents a bond) —$[CH_2]_z$—$Y^1$-$L^2$- arises from the particular chemistry strategy chosen to link the amino acid motif R in substituent W to the rest of the molecule. Clearly the chemistry strategy for that coupling may vary widely, and thus many combinations of the variables $Y^1$, $L^2$, and z are possible. However, when a compound of the invention is bound to an enzyme at its active site, the amino acid motif generally extends in a direction away from the enzyme, and thus minimises or avoids interference with the binding mode of the inhibitor. Hence the precise combination of variables making up the linking chemistry between the amino acid motif and the rest of the molecule will often be irrelevant to the primary binding mode of the compound as a whole.

The subscript z may be 0 or 1, so that a methylene group linked to the purinyl ring system is optional. Preferably z is zero and the methylene group is absent.

Group $Y^1$ $Y^1$ preferably represents a bond or a group of formula —O—, —S—, —O—(C=O)—, —(C=O)—O—, —(C=O)—, —(S=O)—, —$S(O_2)$—, —$NR^3$—, —(C=O)$NR^3$—, —$NR^3$(C=O)—, —$S(O_2)NR^3$— and —$NR^3S(O_2)$—, wherein $R^3$ represents hydrogen or $C_{1-6}$ alkyl. When $R^3$ is $C_{1-6}$ alkyl, it is preferably $C_{1-2}$ alkyl, more preferably ethyl. When $R^3$ is an alkyl group, it is preferably unsubstituted or substituted by one or two substituents which are the same or different and are selected from $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, mercapto, cyano, nitro, $C_{1-4}$ hydroxyalkyl, $C_{2-4}$ hydroxyalkenyl, $C_{1-4}$ alkylthio, $C_{2-4}$ alkenylthio, and —NR'R" groups wherein each R' and R" is the same or different and represents hydrogen or $C_{1-4}$ alkyl, more preferably selected from halogen, $C_{1-2}$ alkyl, $C_{1-2}$ alkoxy, hydroxyl and —NR'R" wherein R' and R" are the same or different and represent hydrogen or $C_{1-2}$ alkyl. Most preferred substituents are halogen, $C_{1-2}$ alkoxy and hydroxyl, in particular hydroxyl.

More preferably $Y^1$ is a bond or represents a group of formula —O—, —S—, —$NR^3$—, —C(=O)—O—, —O—(C=O)—, —(C=O)$NR^3$— or —$NR^3$(C=O)— wherein $R^3$ is as defined above. More preferably $Y^1$ is a bond or represents a group of formula —O—, —S—, —NH—, —O—(C=O)—, —NH(C=O)— or —(C=O)NH—. When $Y^1$ represents —O—, —S— or —$NR^3$—, preferably, in $L^2$, either m is zero (i.e. $Alk^1$ is absent) and n is 1 (i.e. Q is present), or m is 1 (i.e. $Alk^1$ is present) and n and p are zero (i.e. Q and $Alk^2$ are absent). Most preferably $Y^1$ is a bond.

Group $L^2$ $L^2$ represents a group of formula -$(Alk^1)_m$-$(Q)_n$-$(Alk^2)_p$—. The subscripts m, n and p are independently zero or 1. Specifically, in some embodiments of the invention, m and p may be 0 with n being 1. In other embodiments, n and p may be 0 with m being 1. In further embodiments, m, n and p may be all 0. In still further embodiments m may be 0, n may be 1 with Q being a monocyclic aryl, heteroaryl, carbocyclyl or heterocyclyl radical, and p may be 0 or 1, more preferably p is 1. Most preferably either n and p are zero and m is 1; or m is zero, n is 1 with Q being a monocyclic aryl, heteroaryl, carbocyclyl or heterocyclyl radical, and p is 1; for example n and p are zero and m is 1.

Preferred $Alk^1$ groups include $C_{3-6}$ cycloalkyl groups and $C_{1-4}$ alkylene, $C_{2-4}$ alkenylene and $C_{2-4}$ alkynylene groups which may optionally contain or terminate in an ether, thioether or amino —$NR^6$— link wherein $R^6$ represents hydrogen or $C_{1-2}$ alkyl. When $R^6$ is $C_{1-2}$ alkyl, it is preferably unsubstituted or substituted by one or two substituents which are the same or different and are selected from halogen, $C_{1-2}$ alkyl, $C_{1-2}$ alkoxy, hydroxyl and —NR'R" wherein R' and R" are the same or different and represent hydrogen or $C_{1-2}$ alkyl. Most preferred substituents on the $R^6$ group are halogen, $C_{1-2}$ alkoxy and hydroxyl, in particular hydroxyl.

When $Alk^1$ is a $C_{3-6}$ cycloalkyl group, preferred groups include divalent cyclopropyl, cyclopentyl and cyclohexyl groups which optionally contain an ether, thioether or amino —$NR^6$— link wherein $R^6$ represents hydrogen or $C_{1-2}$ alkyl. Preferably the group $R^6$, when present, is unsubstituted. More preferably, when $Alk^1$ is a $C_{3-6}$ cycloalkyl group it is a 5- or 6-membered ring optionally containing an ether or amino —$NR^6$— link. Suitable examples include cyclopentyl, cyclohexyl and heterocyclic groups selected from pyrrolidinyl, tetrahydrofuranyl, tetrahydrothienyl, piperidinyl, tetrahydropyranyl and tetrahydrothiopyranyl. More preferred examples include cyclopentyl, cyclohexyl and pyrrolidinyl.

When $Alk^1$ is a $C_{1-4}$ alkylene group, preferred groups include —$CH_2$—, —$CH_2CH_2$—, —$CH_2CH_2CH_2$— and —$CH_2CH_2CH_2CH_2$—, as well as branched variants such as —$CH(CH_3)$—, —$C(CH_3)_2$—, or in either orientation —$CH_2CH(CH_3)$—, —$CH_2C(CH_3)_2$—. When $Alk^1$ is a $C_{2-4}$ alkenylene group, preferred groups include —CH=CH—, —CH=CH$CH_2$—, —$CH_2$CH=CH— and —$CH_2$CH=CH$CH_2$— as well as branched variants. When $Alk^1$ is a $C_{2-4}$ alkynylene group, preferred groups include —C≡C—, —C≡C$CH_2$—, —$CH_2$C≡C— and —$CH_2$C≡C$CH_2$— as well as branched variants.

When $Alk^1$ is a $C_{1-4}$ alkylene, $C_{2-4}$ alkenylene or $C_{2-4}$ alkynylene group terminating in an ether (—O—), thioether (—S—) or amino (—$NR^6$)— wherein $R^6$ represents hydrogen or $C_{1-2}$ alkyl, preferred groups include (in either orientation)-$CH_2W$—, —$CH_2CH_2W$—, —$CH_2CH_2WCH_2$—, —$CH_2CH_2WCH(CH_3)$—, —$CH_2WCH_2CH_2$—, —$CH_2WCH_2CH_2WCH_2$—, and —$WCH_2CH_2$— where W is —O—, —S—, —NH—, —N($CH_3$)—, or —$CH_2CH_2N(CH_2CH_2OH)CH_2$—. Thus suitable groups include —O—$CH_2$—, —S—$CH_2$— and —O—$CH_2$—$CH_2$—. When $Alk^1$ terminates in an ether, thioether or amino group, preferably $Y^1$ is a bond or a group —(C=O)—, —O(C=O)—, —S(=O)—, —$SO_2$—, —$NR^3$(C=O)— or $NR^3S(O_2)$—, more preferably $Y^1$ is a bond or a group —C(=O)—. More preferably $Alk^1$ does not terminate in or contain an ether, thioether or amino group.

Most preferably $Alk^1$ is a $C_{1-4}$ alkylene group, more preferably it is selected from —$CH_2$—, —$CH_2CH_2$— and —$CH_2$—$CH_2$—$CH_2$—, most preferably $Alk^1$ is —$CH_2CH_2CH_2$—.

$Alk^1$ groups are preferably unsubstituted or substituted by 1 or 2 substituents which are the same or different and are selected from halogen atoms and $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, mercapto, cyano, nitro, $C_{1-4}$ hydroxyalkyl, $C_{2-4}$ hydroxyalkenyl, $C_{1-4}$ alkylthio, $C_{2-4}$ alkenylthio, and —NR'R" groups wherein each R' and R" is the same or different and represents hydrogen or $C_{1-4}$ alkyl. More preferably, $Alk^1$ groups are unsubstituted or substituted by 1 or 2 substituents which are the same or different and are selected from halogen, $C_{1-2}$ alkoxy, hydroxyl and —NR'R" wherein R' and R" are the same or different and represent hydrogen or $C_{1-2}$ alkyl. Most preferably Alk$^1$ groups are unsubstituted.

Preferred Q groups include phenyl, 5- to 10-membered heteroaryl, $C_{3-7}$ carbocyclyl and 5- to 10-membered heterocyclyl groups optionally fused to a further phenyl, 5- to 10-membered heteroaryl, $C_{3-7}$ carbocyclyl or 5- to 10-membered heterocyclyl group. More preferably Q represents a phenyl optionally fused to a further phenyl, a 5- to 10-membered heteroaryl optionally fused to a further phenyl, a non-fused $C_{3-7}$ carbocyclyl or a non-fused 5- to 10-membered heterocyclyl group.

When Q represents a phenyl optionally fused to a further phenyl, it represents phenyl or naphthyl, with phenyl groups being preferred. When Q represents a phenyl it is preferably linked to the rest of the molecule in a 1,4-relationship.

When Q represents a $C_{3-7}$ carbocyclyl group it is preferably a cyclopropyl, cyclopentyl or cyclohexyl group, more preferably a cyclohexyl group.

When Q represents a 5- to 10-membered heteroaryl group optionally fused to a further phenyl it is preferably a 5- to 6-membered heteroaryl group optionally fused to a further phenyl. When Q represents a non-fused 5- to 6-membered heteroaryl group it is preferably a pyridyl, thienyl, furyl or pyrrolyl group, more preferably a pyridyl, thienyl or pyrrolyl group. When Q represents a 5- to 6-membered heteroaryl group fused to a phenyl, it is preferably an indolyl, benzimidazolyl, benzofuryl or benzothienyl group, more preferably an indolyl group.

When Q represents a 5- to 10-membered heterocyclyl group it is preferably a non-fused 5- to 6-membered heterocyclyl group, for example a piperidinyl or piperazinyl group.

Most preferred Q groups, when present, include phenyl, pyridinyl, thienyl and cyclohexyl, e.g. phenyl and cyclohexyl, more preferably phenyl. However, in one preferred embodiment subscript n is zero and the group Q is absent.

Q groups are preferably unsubstituted or substituted by 1 or 2 substituents which are the same or different and are selected from halogen atoms and $C_{1-4}$ alkyl, $C_{1-4}$ alkoxy, $C_{1-4}$ haloalkyl, hydroxyl, cyano, nitro and —NR'R" groups wherein each R' and R" is the same or different and represents hydrogen or $C_{1-4}$ alkyl, and groups of formula COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$ wherein R$^A$ and R$^B$ are the same or different and represent $C_{1-2}$ alkyl. More preferably Q groups are unsubstituted or substituted by 1 or 2 substituents which are the same or different and are selected from halogen atoms and $C_{1-4}$ alkyl, $C_{1-4}$ alkoxy and hydroxyl groups. Most preferably Q groups are unsubstituted.

Preferred Alk$^2$ groups include $C_{3-6}$ cycloalkyl groups, and $C_{1-4}$ alkylene, $C_{2-4}$ alkenylene and $C_{2-4}$ alkynylene groups which may optionally contain or terminate in an ether, thioether or amino —NR$^6$— link wherein R$^6$ represents hydrogen or $C_{1-2}$ alkyl. When R$^6$ is $C_{1-2}$ alkyl, it is preferably unsubstituted or substituted by one or two substituents which are the same or different and are selected from halogen, $C_{1-2}$ alkyl, $C_{1-2}$ alkoxy, hydroxyl and —NR'R" wherein R' and R" are the same or different and represent hydrogen or $C_{1-2}$ alkyl. Most preferred substituents on the R$^6$ group are halogen, $C_{1-2}$ alkoxy and hydroxyl, in particular hydroxyl.

When Alk$^2$ is a $C_{3-6}$ cycloalkyl group, preferred groups include divalent cyclopropyl, cyclopentyl and cyclohexyl groups.

When Alk$^2$ is a $C_{1-4}$ alkylene group, preferred groups include —CH$_2$—, —CH$_2$CH$_2$—, —CH$_2$CH$_2$CH$_2$— and —CH$_2$CH$_2$CH$_2$CH$_2$—, as well as branched variants such as —CH(CH$_3$)—, —C(CH$_3$)$_2$—, or in either orientation —CH$_2$CH(CH$_3$)—, —CH$_2$C(CH$_3$)$_2$—. Most preferred groups are —CH$_2$— and —CH$_2$—CH$_2$—. When Alk$^2$ is a $C_{2-4}$ alkenylene group, preferred groups include —CH=CH—, —CH=CHCH$_2$—, —CH$_2$CH=CH— and —CH$_2$CH=CHCH$_2$— as well as branched variants. When Alk$^2$ is a $C_{2-4}$ alkynylene group, preferred groups include —C≡C—, —C≡CCH$_2$—, —CH$_2$C≡C— and —CH$_2$C≡CCH$_2$— as well as branched variants.

When Alk$^2$ is a $C_{1-4}$ alkylene, $C_{2-4}$ alkenylene or $C_{2-4}$ alkynylene group terminating in an ether (—O—), thioether (—S—) or amino (—NR$^6$— wherein R$^6$ represents hydrogen or $C_{1-2}$ alkyl), preferred groups include (in either orientation)-CH$_2$W—, —CH$_2$CH$_2$W—, —CH$_2$CH$_2$WCH$_2$—, —CH$_2$CH$_2$WCH(CH$_3$)—, —CH$_2$WCH$_2$CH$_2$—, —CH$_2$WCH$_2$CH$_2$WCH$_2$—, and —WCH$_2$CH$_2$— where W is —O—, —S—, —NH—, —N(CH$_3$)—, or —CH$_2$CH$_2$N(CH$_2$CH$_2$OH)CH$_2$—. More preferably Alk$^2$ does not terminate in or contain an ether, thioether or amino group.

Most preferable Alk$^2$ groups are $C_{1-4}$ alkylene groups, in particular —CH$_2$— and —CH$_2$CH$_2$—. However, in one preferred embodiment subscript p is zero and the group Alk$^2$ is absent.

Alk$^2$ groups are preferably unsubstituted or substituted by 1 or 2 substituents which are the same or different and are selected from halogen atoms and $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, mercapto, cyano, nitro, $C_{1-4}$ hydroxyalkyl, $C_{2-4}$ hydroxyalkenyl, $C_{1-4}$ alkylthio, $C_{2-4}$ alkenylthio, and —NR'R" groups wherein each R' and R" is the same or different and represents hydrogen or $C_{1-4}$ alkyl. More preferably, Alk$^2$ groups are preferably unsubstituted or substituted by 1 or 2 substituents which are the same or different and are selected from halogen, $C_{1-2}$ alkoxy, hydroxyl and —NR'R" wherein R' and R" are the same or different and represent hydrogen or $C_{1-2}$ alkyl. Most preferably Alk$^2$ groups are unsubstituted.

In a preferred embodiment, m is 1, n and p are zero and L$^2$ preferably represents $C_{1-4}$ alkylene, more preferably —CH$_2$—, —CH$_2$CH$_2$— or —CH$_2$CH$_2$CH$_2$—, most preferably —CH$_2$CH$_2$— or —CH$_2$CH$_2$CH$_2$—. In another embodiment m is zero, n and p are 1 and L$^2$ represents -Cyc'-Alk$^2$- wherein Cyc' represents a non-fused phenyl or a non-fused $C_{3-6}$ cycloalkyl group, substituted as described for Q above and Alk$^2$ represents $C_{1-4}$ alkylene, more preferably —CH$_2$— or —CH$_2$CH$_2$—. In another preferred embodiment, m is zero, n and p are 1 and L$^2$ represents -Cyc'-Alk$^2$- wherein Cyc' represents a non-fused phenyl or a non-fused 5- to 10-membered heteroaryl and Alk$^2$ represents $C_{1-4}$ alkylene, more preferably —CH$_2$— or —CH$_2$CH$_2$—.

Preferred examples of the group —[CH$_2$], —Y$^1$-L$^2$- in its entirety include —CH$_2$CH$_2$—, —CH$_2$CH$_2$CH$_2$—, —(C=O)NH—(CH$_2$)$_2$—, —(C=O)NH—(CH$_2$)$_3$—, —NH—(CH$_2$)$_3$—, —NH—C(=O)—CH$_2$—, —NH—C(=O)—CH$_2$—CH$_2$—, —O—C(=O)—CH$_2$—, —O—C(=O)—CH$_2$CH$_2$—, —S—CH$_2$—, —S—CH$_2$—CH$_2$—, —NH—(CH$_2$)$_4$—, —O—CH$_2$— and —O—CH$_2$—CH$_2$—, and groups of formula:

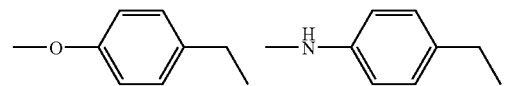

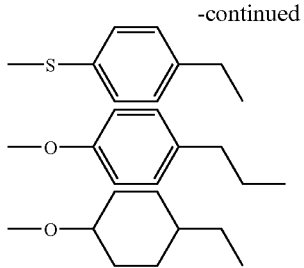

A further preferred example of the group —[CH$_2$]$_x$—Y$^1$-L$^2$- in its entirety is

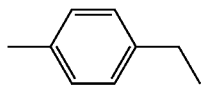

More preferred examples of the group —[CH$_2$]$_z$—Y$^1$-L$^2$- in its entirety include —CH$_2$CH$_2$CH$_2$— and

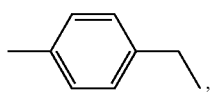

for example —CH$_2$CH$_2$CH$_2$—.

Ring D

Ring D is present when group R is of formula (Y). Preferred groups (Y) include those where Ring D is a non-fused 5- to 6-membered heteroaryl or heterocyclyl group where R$^7$ is linked to a ring carbon atom adjacent the nitrogen atom shown in Ring D. More preferably Ring D is a non-fused 5- to 6-membered heterocyclyl group, for example a pyrrolidinyl, oxazolidinyl, isoxazolidinyl, imidazolidinyl, pyrazolidinyl, thiazolidinyl, isothiazolidinyl, piperidinyl, hexahydropyrimidinyl, piperazinyl, morpholinyl or thiomorpholinyl group. More preferably Ring D is a pyrrolidinyl or piperidinyl group.

Preferably Ring D, in addition to bearing group R$^7$ and being bonded to the rest of the molecule, is unsubstituted or substituted by 1 or 2 groups selected from halogen atoms and C$_{1-4}$ alkyl, C$_{1-4}$ alkoxy and hydroxyl groups. More preferably Ring D, apart from bearing group R$^7$ and being bonded to the rest of the molecule, is unsubstituted. Thus, particularly preferred Ring D groups are:

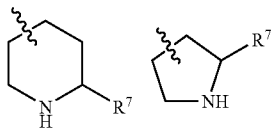

Preferred compounds of the invention are (a) amino acid derivatives of formula (I) above or a tautomer thereof, or (b) a pharmaceutically acceptable salt, N-oxide, hydrate or solvate thereof, wherein:

R$^1$ represents-hydrogen or halogen atom, or an unsubstituted C$_{1-4}$ alkyl, hydroxyl, C$_{1-4}$ alkoxy, mercapto, C$_{1-4}$ alkylthio, —NR'R" or —CONR$^A$R$^B$ group where R', R", R$^A$ and R$^B$ are the same or different and represent hydrogen or unsubstituted C$_{1-4}$ alkyl group, and wherein the alkyl groups or moieties in R$^1$ are unsubstituted or substituted by 1, 2 or 3 substituents which are themselves unsubstituted and are selected from halogen, C$_{1-4}$ alkyl, C$_{2-4}$ alkenyl, C$_{1-4}$ alkoxy, hydroxyl, C$_{1-4}$ haloalkyl, C$_{2-4}$ haloalkenyl, C$_{1-4}$ haloalkyloxy, C$_{2-4}$ haloalkenyloxy and —NR'R" wherein R' and R" are the same or different and represent hydrogen or C$_{1-2}$ alkyl;

R$^2$ represents a hydrogen or halogen atom, an unsubstituted C$_{1-4}$ alkyl group or a group of formula —NR'R" where R' and R" are the same or different and represent hydrogen or unsubstituted C$_{1-2}$ alkyl;

x is zero and y is one;

Het represents —S—, —S(O)— or —S(O)$_2$—;

A represents an unsubstituted or substituted group selected from non-fused phenyl, non-fused 5- to 6-membered heteroaryl, non-fused C$_{3-7}$ carbocyclyl, non-fused 5- to 6-membered heterocyclyl group, a phenyl group which is fused to a further 5- to 6-membered heterocyclyl group, or a 5- to 6-membered heteroaryl group which is fused to a further phenyl group, and wherein the phenyl, heteroaryl, carbocyclyl and heterocyclyl groups and moieties are unsubstituted or substituted by 1, 2, 3 or 4 substituents which are the same or different and are selected from halogen atoms and C$_{1-4}$ alkyl, C$_{2-4}$ alkenyl, C$_{1-4}$ alkoxy, C$_{2-4}$ alkenyloxy, C$_{1-4}$ haloalkyl, C$_{2-4}$ haloalkenyl, C$_{1-4}$ haloalkoxy, C$_{2-4}$ haloalkenyloxy, hydroxyl, mercapto, cyano, nitro, C$_{1-4}$ hydroxyalkyl, C$_{2-4}$ hydroxyalkenyl, C$_{1-4}$ alkylthio, C$_{2-4}$ alkenylthio and —NR'R" groups wherein each R' and R" is the same or different and represents hydrogen or C$_{1-4}$ alkyl, and groups of formula COR$^A$, —SO$_2$R$^A$, —CONH$_2$, —SO$_2$NH$_2$, —CONHR$^A$, —SO$_2$NHR$^A$, —CONR$^A$R$^B$ and —SO$_2$NR$^A$R$^B$ wherein R$^A$ and R$^B$ are the same or different and represent C$_{1-4}$ alkyl;

z is zero;

Y$^1$ is a bond or represents a group of formula —O—, —S—, —O—(C=O)—, —(C=O)—O—, —(C=O)—, —(S=O)—, —S(O$_2$)—, —NR$^3$—, —(C=O)NR$^3$—, —NR$^3$(C=O)—, —S(O$_2$)NR$^3$— and —NR$^3$S(O$_2$)—, wherein R$^3$ represents hydrogen or C$_{1-6}$ alkyl;

m, n and p are the same or different and represent zero or 1;

Alk$^1$ represents a C$_{1-4}$ alkylene group which is unsubstituted or substituted by 1 or 2 substituents which are the same or different and are selected from halogen, C$_{1-2}$ alkoxy, hydroxyl and —NR'R" wherein R' and R" are the same or different and represent hydrogen or C$_{1-2}$ alkyl;

Q represents phenyl optionally fused to a further phenyl, a 5- to 10-membered heteroaryl optionally fused to a further phenyl, a non-fused C$_{3-7}$ carbocyclyl or a non-fused 5- to 10-membered heterocyclyl group, and wherein the phenyl, heteroaryl, carbocyclyl and heterocyclyl groups of Q are unsubstituted or substituted by 1 or 2 substituents which are the same or different and are selected from halogen atoms and C$_{1-4}$ alkyl, C$_{1-4}$ alkoxy and hydroxyl groups;

Alk$^2$ represents a C$_{1-4}$ alkylene group which is unsubstituted or substituted by 1 or 2 substituents which are the same or different and are selected from halogen, C$_{1-2}$ alkoxy, hydroxyl and —NR'R" wherein R' and R" are the same or different and represent hydrogen or C$_{1-2}$ alkyl;

R represents a group of formula (X);

R$^7$ represents —COOH or is an ester group —COOR$^{11}$ wherein the ester group is hydrolysable by one or more intracellular carboxylesterase enzymes to a carboxylic acid group; and $R^8$ represents hydrogen or a $C_{1-6}$ alkyl, —(C=O)$R^9$ or —(C=O)O$R^{10}$ wherein $R^9$ and $R^{10}$ are as defined above.

Further preferred compounds of the invention are (a) amino acid derivatives of formula (IA) below or a tautomer thereof, or (b) a pharmaceutically acceptable salt thereof:

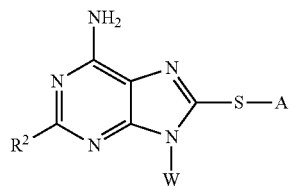

(IA)

wherein:
$R^2$ represents a hydrogen or halogen atom, an unsubstituted $C_{1-4}$ alkyl group or a group of formula —NR'R" where R' and R" are the same or different and represent hydrogen or unsubstituted $C_{1-2}$ alkyl;

A represents an unsubstituted or substituted group selected from non-fused phenyl, non-fused 5- to 6-membered heteroaryl, non-fused $C_{3-7}$ carbocyclyl, non-fused 5- to 6-membered heterocyclyl group, a phenyl group which is fused to a further 5- to 6-membered heterocyclyl group, or a 5- to 6-membered heteroaryl group which is fused to a further phenyl group, and wherein the phenyl, heteroaryl, carbocyclyl and heterocyclyl groups and moieties are unsubstituted or substituted by 1, 2, 3 or 4 substituents which are the same or different and are selected from halogen atoms and $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_2J_4$ haloalkenyloxy, hydroxyl, mercapto, cyano, nitro, $C_{1-4}$ hydroxyalkyl, $C_{2-4}$ hydroxyalkenyl, $C_{1-4}$ alkylthio, $C_2J_4$ alkenylthio and —NR'R" groups wherein each R' and R" is the same or different and represents hydrogen or $C_{1-4}$ alkyl, and groups of formula COR$^A$, —SO$_2$R$^A$, —CONH$_2$, —SO$_2$NH$_2$, —CONHR$^A$, —SO$_2$NHR$^A$, —CONR$^A$R$^B$ and —SO$_2$NR$^A$R$^B$ wherein R$^A$ and R$^B$ are the same or different and represent $C_{1-4}$ alkyl; and W is a group of formula —Y$^1$-L$^2$-R, and R is a group of formula (X);

$Y^1$ is a bond or represents a group of formula —O—, —S—, —O—(C=O)—, —(C=O)—O—, —(C=O)—, —(S=O)—, —S(O$_2$)—, —NR$^3$—, —(C=O)NR$^3$—, —NR$^3$(C=O)—, —S(O$_2$)NR$^3$— and —NR$^3$S(O$_2$)—, wherein R$^3$ represents hydrogen or $C_{1-6}$ alkyl;

either (i) m is 1, n and p are zero, and L$^2$ represents a group -Alk$^1$- wherein Alk$^1$ represents a $C_{1-4}$ alkylene group which is unsubstituted or substituted by 1 or 2 substituents which are the same or different and are selected from halogen, $C_{1-2}$ alkoxy, hydroxyl and —NR'R" wherein R' and R" are the same or different and represent hydrogen or $C_{1-2}$ alkyl; or (ii) m is zero, n and p are 1, L$^2$ represents non-fused phenyl or a non-fused 5- to 10-membered heteroaryl group and Alk$^2$ represents a $C_4$ alkylene group;

$R^7$ represents —COOH or is an ester group —COOR$^{11}$ wherein the ester group is hydrolysable by one or more intracellular carboxylesterase enzymes to a carboxylic acid group; and $R^8$ represents hydrogen or a $C_{1-6}$ alkyl, —(C=O)R$^9$ or —(C=O)OR$^{10}$ wherein R$^9$ is $C_{1-6}$ alkyl, non-fused phenyl, non-fused 5- to 6-membered heteroaryl, non-fused $C_{3-7}$ carbocyclyl or a group -Alk$^4$-Cyc, and R$^{10}$ is hydrogen or $C_{1-4}$ alkyl.

Preferably in formula (IA), R$^2$ represents a hydrogen or halogen atom or an —NH$_2$ group, more preferably a hydrogen atom.

Preferably in formula (IA), A represents a group selected from phenyl, pyrrolyl, furanyl, thienyl, pyridinyl, pyridazinyl, pyrimidinyl, pyrazinyl, triazinyl, benzimidazolyl, benzoxazolyl, benzothiazolyl, tetrahydrofuranyl, pyrrolidinyl, tetrahydrothienyl, piperidinyl, tetrahydropyranyl, tetrahydrothiopyranyl, morpholinyl, thiomorpholinyl, pyrrolyl-2,5-dione and benzoquinone, or A represent a phenyl ring fused to a 5- to 6-membered heterocyclyl group selected from oxazolidinyl, imidazolidinyl, thiazolidinyl, thioxolanyl, dioxolanyl and dithiolanyl, and wherein A is unsubstituted or substituted by 1, 2, 3 or 4 substituents which are the same or different and represent halogen atoms or $C_{1-4}$ alkyl, $C_{1-2}$ alkoxy, $C_{1-2}$ alkylthio or hydroxy groups, more preferably A represents a non-fused phenyl ring or a phenyl ring fused to a dioxolanyl ring, and wherein A is unsubstituted or substituted by 1, 2, 3 or 4 substituents which are the same or different and represent halogen atoms or $C_{1-4}$ alkyl, $C_{1-2}$ alkoxy, $C_{1-2}$ alkylthio or hydroxy groups.

Preferably in formula (IA), $Y^1$ is a bond or represents a group of formula —O—, —S—, —NR$^3$—, —C(=O)—O—, —O—(C=O)—, —(C=O)NR$^3$— or —NR$^3$(C=O)— wherein R$^3$ is hydrogen or $C_{1-6}$ alkyl, more preferably $Y^1$ is a bond.

Preferably in formula (IA), R$^7$ represents a group —COOH or —COOR$^{11}$, wherein R$^{11}$ represents —CR$^{12}$R$^{13}$R$^{14}$ and:

(i) R$^{13}$ represents hydrogen or a group of formula —[C$_{1-4}$ alkylene]$_b$-(Z$^1$)$_a$-[C$_{1-4}$ alkyl] or —[C$_{1-4}$ alkylene]$_b$-(Z$^1$)$_a$-[C$_{2-4}$ alkenyl] wherein a and b are the same or different and represent 0 or 1, and Z$^1$ represents —O—, —S—, or —NR$^{17}$— wherein R$^{17}$ is hydrogen or $C_{1-4}$ alkyl, R$^{14}$ represents hydrogen or $C_{1-4}$ alkyl, and R$^{12}$ represents hydrogen or $C_{1-4}$ alkyl;

(ii) R$^{13}$ represents a phenyl or a 5- to 10-membered heteroaryl group optionally fused to a further phenyl, 5- to 10-membered heteroaryl, $C_{3-7}$ carbocyclyl or 5- to 10-membered heterocyclyl group, R$^{14}$ represents hydrogen or $C_{1-4}$ alkyl, and R$^{12}$ represents hydrogen;

(iii) R$^{13}$ represents a group of formula -(Alk$^3$)—NR$^{15}$R$^{16}$ wherein Alk$^3$ represents a $C_{1-4}$ alkylene group and either (a) R$^{15}$ and R$^{16}$ are the same or different and represent hydrogen or $C_{1-4}$ alkyl, or (b) R$^{15}$ and R$^{16}$, together with the nitrogen atom to which they are bonded, form a 5- to 10-membered heteroaryl or 5- to 10-membered heterocyclyl group optionally fused to a further phenyl, 5- to 10-membered heteroaryl, $C_{3-7}$ carbocyclyl or 5- to 10-membered heterocyclyl group; R$^{14}$ represents hydrogen or $C_{1-4}$ alkyl, and R$^{12}$ represents hydrogen; or (iv) R$^{13}$ and R$^{14}$, together with the carbon atom to which they are bonded, form a phenyl, 5- to 10-membered heteroaryl, $C_{3-7}$ carbocyclyl or 5- to 10-membered heterocyclyl group which is optionally fused to a further phenyl, 5- to 10-membered heteroaryl, $C_{3-7}$ carbocyclyl or 5- to 10-membered heterocyclyl group, and R$^{12}$ represents hydrogen.

Preferably in formula (IA), $R^{11}$ represents —$CR^{12}R^{13}R^{14}$, and either:
- (i) $R^{12}$ represents hydrogen or $C_{1-2}$ alkyl; $R^{13}$ represents hydrogen, $C_{1-4}$ alkyl, $C_{2-4}$ alkenyl or a group —($C_{1-4}$ alkyl)-O—($C_{1-4}$ alkyl); and $R^{14}$ represents hydrogen or $C_{1-2}$ alkyl; or
- (ii) $R^{12}$ represents hydrogen or $C_{1-2}$ alkyl, and $R^{13}$ and $R^{14}$ form a cyclic group together with the carbon atom to which they are bonded, form a non-fused $C_{3-7}$ carbocyclyl groups which is unsubstituted or substituted by one or two substituents which are the same or different and are selected from halogen atoms and $C_{1-4}$ alkyl, $C_{1-4}$ alkylene, $C_{1-4}$ alkoxy, $C_{1-4}$ haloalkyl, hydroxyl, cyano, nitro and —NR'R" groups wherein each R' and R" is the same or different and represents hydrogen or —$C_{1-4}$-alkyl.

Further preferred compounds of the invention are (a) amino acid derivatives of formula (IB) above or a tautomer thereof, or (b) a pharmaceutically acceptable salt thereof:

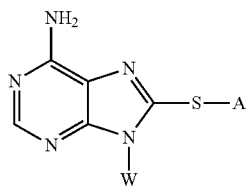

(IB)

wherein:
A represents a non-fused phenyl ring or a phenyl ring fused to a dioxolanyl ring, and wherein A is unsubstituted or substituted by 1, 2, 3 or 4 substituents which are the same or different and represent halogen atoms or $C_{1-4}$ alkyl, $C_{1-2}$ alkoxy, $C_{1-2}$ alkylthio or hydroxy groups; and
W represent a group of formula —$Y^1$-$L^2$-R wherein:
  $Y^1$ is a bond or represents a group —O—, —S—, —$NR^3$—, —C(=O)—O—, —O—(C=O)—, —(C=O)$NR^3$— or —$NR^3$(C=O)— wherein $R^3$ is hydrogen or $C_{1-6}$ alkyl;
  $L^2$ represents a group -$Alk^1$- or a group -Q-$Alk^2$-, and -$Alk^1$- represents an unsubstituted $C_{1-4}$ alkylene group, Q represents a non-fused phenyl ring or a non-fused pyridinyl or thienyl ring and $Alk^2$ represents an unsubstituted $C_{1-4}$ alkylene group; and
  R represents a group of formula (X);
  $R^7$ represents —COOH or —COOR$^{11}$ wherein $R^{11}$ represents —$CR^{12}R^{13}R^{14}$, and either:
  (i) $R^{12}$ represents hydrogen or $C_{1-2}$ alkyl; $R^{13}$ represents hydrogen, $C_{1-4}$ alkyl, $C_{2-4}$ alkenyl or a group —($C_{1-4}$ alkyl)-O—($C_{1-4}$ alkyl); and $R^{14}$ represents hydrogen or $C_{1-2}$ alkyl; or
  (ii) $R^{12}$ represents hydrogen or $C_{1-2}$ alkyl, and $R^{13}$ and $R^{14}$ form a cyclic group together with the carbon atom to which they are bonded, form a non-fused $C_{3-7}$ carbocyclyl groups which is unsubstituted or substituted by one or two substituents which are the same or different and are selected from halogen atoms and $C_{1-4}$ alkyl, $C_{1-4}$ alkylene, $C_{1-4}$ alkoxy, $C_{1-4}$ haloalkyl, hydroxyl, cyano, nitro and —NR'R" groups wherein each R' and R" is the same or different and represents hydrogen or $C_{1-4}$ alkyl; and
  $R^8$ represents hydrogen or a $C_{1-6}$ alkyl, —(C=O)$R^9$ or —(C=O)OR$^{10}$ wherein $R^9$ is $C_{1-6}$ alkyl, non-fused phenyl, non-fused 5- to 6-membered heteroaryl, non-fused $C_{3-7}$ carbocyclyl or a group -$Alk^4$-Cyc, and $R^{10}$ is hydrogen or $C_{1-4}$ alkyl.

Preferably in formula (IB) A represents a phenyl ring fused to a dioxolanyl ring, and wherein A is unsubstituted or substituted by 1 or 2 substituents which are the same or different and represent halogen atoms or $C_{1-4}$ alkyl, $C_{1-2}$ alkoxy, $C_{1-2}$ alkylthio or hydroxy groups. Preferably in formula (IB) $Y^1$ is a bond. Preferably in formula (IB) $R^7$ represents —COOH or —COOR$^{11}$ and $R^{11}$ represents a $C_{1-4}$ alkyl or a $C_{3-7}$ carbocyclyl group. Preferably in formula (IB) $R^8$ represents hydrogen. In one embodiment in formula (IB) $L^2$ represents a group -$Alk^1$- and $Alk^1$ represents an unsubstituted $C_{1-4}$ alkylene group.

Further preferred compounds of the invention are (a) amino acid derivatives of formula (IC) above or a tautomer thereof, or (b) a pharmaceutically acceptable salt thereof:

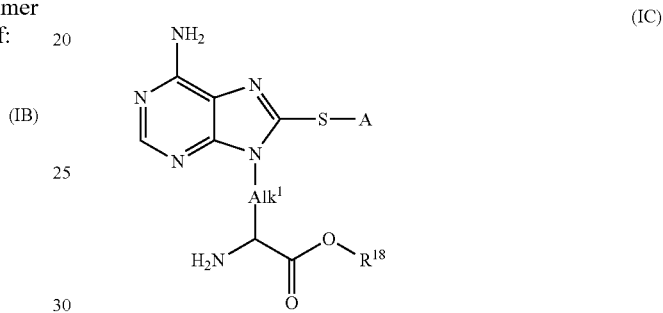

(IC)

wherein:
A represents a non-fused phenyl ring or a phenyl ring fused to a dioxolanyl ring, and wherein A is unsubstituted or substituted by 1 or 2 substituents which are the same or different and represent halogen atoms or $C_{1-4}$ alkyl, $C_{1-2}$ alkoxy, $C_{1-2}$ alkylthio or hydroxy groups;
$Alk^1$ represents a $C_{1-4}$ alkylene group; and
$R^{18}$ represents hydrogen, $C_{1-4}$ alkyl or a $C_{3-7}$ carbocyclyl.
More preferably in formula (IC) $R^{18}$ represents hydrogen, t-butyl or cyclopentyl, most preferably hydrogen or cyclopentyl. More preferably in formula (IC) $Alk^1$ represents —$CH_2$—, —$CH_2CH_2$— or —$CH_2CH_2CH_2$—, most preferably —$CH_2CH_2$— or —$CH_2CH_2CH_2$—.

Further preferred compounds of the invention are (a) amino acid derivatives of formula (ID) below or a tautomer thereof, or (b) a pharmaceutically acceptable salt thereof:

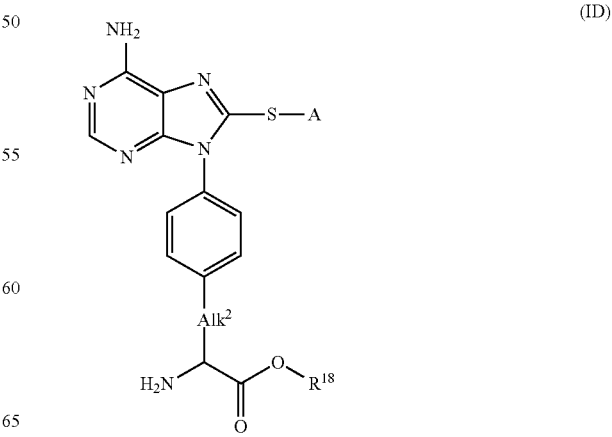

(ID)

wherein:
A represents a non-fused phenyl ring or a phenyl ring fused to a dioxolanyl ring, and wherein A is unsubstituted or substituted by 1 or 2 substituents which are the same or different and represent halogen atoms or $C_{1-4}$ alkyl, $C_{1-2}$ alkoxy, $C_{1-2}$ alkylthio or hydroxy groups;
$Alk^2$ represents a $C_{1-4}$ alkylene group; and
$R^{18}$ represents hydrogen, $C_{1-4}$ alkyl or a $C_{3-7}$ carbocyclyl.

More preferably in formula (ID), $R^{18}$ represents hydrogen, t-butyl or cyclopentyl, most preferably hydrogen or cyclopentyl. More preferably in formula (ID), $Alk^2$ represents —$CH_2$— or —$CH_2CH_2$—.

Particularly preferred compounds of formula (I) are:
(S)-Cyclopentyl 2-amino-5-(6-amino-8-(6-iodobenzo[d][1,3]dioxol-5-ylthio)-9H-purin-9-yl)pentanoate;
(S)-Cyclopentyl 2-amino-4-(6-amino-8-(6-iodobenzo[d][1,3]dioxol-5-ylthio)-9H-purin-9-yl)butanoate;
(S)-2-Amino-5-(6-amino-8-(6-iodobenzo[d][1,3]dioxol-5-ylthio)-9H-purin-9-yl)pentanoic acid;
(S)-2-Amino-4-(6-amino-8-(6-iodobenzo[d][1,3]dioxol-5-ylthio)-9H-purin-9-yl)butanoic acid;
(R)-Cyclopentyl 2-amino-5-(6-amino-8-(6-iodobenzo[d][1,3]dioxol-5-ylthio)-9H-purin-9-yl)pentanoate;
(R)-Cyclopentyl 2-amino-4-(6-amino-8-(6-iodobenzo[d][1,3]dioxol-5-ylthio)-9H-purin-9-yl)butanoate;
(S)-tert-Butyl 2-amino-5-(6-amino-8-(6-iodobenzo[d][1,3]dioxol-5-ylthio)-9H-purin-9-yl)pentanoate;
Cyclopentyl 3-{6-amino-8-[(6-iodo-1,3-benzodioxol-5-yl)thio]-9H-purin-9-yl}-L-alaninate;
Cyclopentyl 4-{6-amino-8-[(1,3-benzodioxol-5-yl)thio]-9H-purin-9-yl}-L-phenylalaninate;
Cyclopentyl 4-{6-amino-8-[(6-bromo-1,3-benzodioxol-5-yl)thio]-9H-purin-9-yl}-L-phenylalaninate;
(R)-2-Amino-4-(6-amino-8-(6-iodo benzo[d][1,3]dioxol-5-ylthio)-9H-purin-9-yl) butanoic acid;
(R)-2-Amino-5-(6-amino-8-[(6-iodo-1,3-benzodioxol-5-ylthio)]-9H-purin-9-yl)pentanoic acid;
4-{6-Amino-8-[(1,3-benzodioxol-5-yl)thio]-9H-purin-9-yl}-L-phenylalanine; and
4-{6-Amino-8-[(6-bromo-1,3-benzo dioxol-5-yl)thio]-9H-purin-9-yl}-L-phenyl alanine.

The compounds of the invention comprise a derivatised purine core, with a side chain (W) which terminates in an amino acid or amino acid ester end group. The purine cores of the compounds are similar to a number of known purine analogues which have HSP90 inhibition activity. The binding of such compounds to HSP90 has been characterised by x-ray crystallography (Immormino et al, J. Med. Chem. 2006, 49, 4953-4960, PDB code 2FWZ). Such studies indicate that the side chain W will not interfere with the ability of the compounds to inhibit HSP90, and instead acts as a group which can be enzymatically modified to alter the compounds ability to enter and exit a cell. Accordingly, despite addition of the side chain W, the compounds of the invention will still be useful as HSP90 inhibitors, and will therefore be useful in the treatment of conditions which are mediated by inappropriate HSP90 activity. A suitable assay for assessing the activity of the compounds of the invention is as follows:

Cell Inhibition Assay

Cancer cell lines (e.g. HCT 116 and HUT) can be grown in log phase then harvested and seeded at 1000 cells/well (200 μl final volume) into 96-well tissue culture plates. Following 24 h of cell growth, cells can be treated with the claimed compounds (final concentration of 20 μM). Plates can then be re-incubated for a further 72 h before a sulphorhodamine B (SRB) cell viability assay is conducted according to Skehan J. Natl. Canc. Inst 1990, 82, 1107-1112.

Data from the assay can be expressed as a percentage inhibition of the control, measured in the absence of inhibitor, as follows:

$$\% \text{ inhibition} = 100 - ((S^i/S^o) \times 100)$$

where $S^i$ is the signal in the presence of inhibitor and $S^o$ is the signal in the presence of DMSO. IC50 can then be determined by non-linear regression analysis, for example after fitting the results of eight data points to the equation for sigmoidal dose response with variable slope (% activity against log concentration of compound), using Graphpad Prism software.

As mentioned above, the compounds with which the invention is concerned are inhibitors of HSP90 activity and are therefore of use for treatment of cancer, autoimmune and inflammatory diseases, including chronic obstructive pulmonary disease, asthma, rheumatoid arthritis, psoriasis, inflammatory bowel disease, Crohn's disease, ulcerative colitis, multiple sclerosis, diabetes, atopic dermatitis, graft versus host disease, systemic lupus erythematosis and others. A preferred utility of the compounds of the invention is for use in the treatment of cancer.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, but an exemplary dosage would be 0.1-1000 mg per day The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers, for example lactose, sugar, maize-starch, calcium phosphate, sorbitol or glycine; tabletting lubricant, for example magnesium stearate, talc, polyethylene glycol or silica; disintegrants, for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application by inhalation, the drug may be formulated for aerosol delivery for example, by pressure-driven jet atomizers or ultrasonic atomizers, or preferably by propellant-driven metered aerosols or propellant-free administration of micronized powders, for example, inhalation capsules or other "dry powder" delivery systems. Excipients, such as, for example, propellants (e.g. Frigen in the case of metered aerosols), surface-active substances, emulsifiers, stabilizers, preservatives, flavourings, and fillers (e.g. lactose in the case of powder inhalers) may be present in such inhaled formulations. For the purposes of inhalation, a large number of apparata are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described in European Patent Application EP 0 505 321).

For topical application to the eye, the drug may be made up into a solution or suspension in a suitable sterile-aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The compounds of the invention may be used in conjunction with a number of known pharmaceutically active substances. For example, the compounds of the invention may be used with cytotoxics, HDAC inhibitors, kinase inhibitors, aminopeptidase inhibitors and monoclonal antibodies (for example those directed at growth factor receptors). Preferred cytotoxics include, for example, taxanes, platins, anti-metabolites such as 5-fluoracil, topoisomerase inhibitors and the like. The medicaments of the invention comprising amino acid derivatives of formula (I), tautomers thereof or pharmaceutically acceptable salts, N-oxides, hydrates or solvates thereof therefore typically further comprise a cytotoxic, an HDAC inhibitor, a kinase inhibitor, an aminopeptidase inhibitor and/or a monoclonal antibody.

Further, the present invention provides a pharmaceutical composition comprising:

(a) an amino acid derivative of formula (I), a tautomer thereof or a pharmaceutically acceptable salt, N-oxide, hydrate or solvate thereof;

(b) a cytotoxic agent, an HDAC inhibitor, a kinase inhibitor, an aminopeptidase inhibitor and/or a monoclonal antibody; and (c) a pharmaceutically acceptable carrier or diluent.

Also provided is a product comprising:

(a) an amino acid derivative of formula (I), a tautomer thereof or a pharmaceutically acceptable salt, N-oxide, hydrate or solvate thereof; and (b) a cytotoxic agent, an HDAC inhibitor, a kinase inhibitor, an aminopeptidase inhibitor and/or a monoclonal antibody, for the separate, simultaneous or sequential use in the treatment of the human or animal body.

Synthesis

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to those skilled in the art. Typical literature sources are "Advanced organic chemistry", $4^{th}$ Edition (Wiley), J March, "Comprehensive Organic Transformation", $2^{nd}$ Edition (Wiley), R. C. Larock, "Handbook of Heterocyclic Chemistry", $2^{nd}$ Edition (Pergamon), A. R. Katritzky, review articles such as found in "Synthesis", "Acc. Chem. Res.", "Chem. Rev", or primary literature sources identified by standard literature searches online or from secondary sources such as "Chemical Abstracts" or "Beilstein".

The compounds of the invention may be prepared by a number of processes generally described below and more specifically in the Examples hereinafter. In the reactions described below, it may be necessary to protect reactive functional groups, for example hydroxyl, amino and carboxy groups, where these are desired in the final product, to avoid their unwanted participation in the reactions [see for example Greene, T. W., "Protecting Groups in Organic Synthesis", John Wiley and Sons, 1999]. Conventional protecting groups may be used in conjunction with standard practice. In some instances deprotection may be the final step in the synthesis of a compound of general formula (1), and the processes according to the invention described herein after are understood to extend to such removal of protecting groups.

Thus, in one aspect of the invention amino acid esters of general formula (3) may be prepared by, but not restricted to, the methods outlined in Scheme 1.

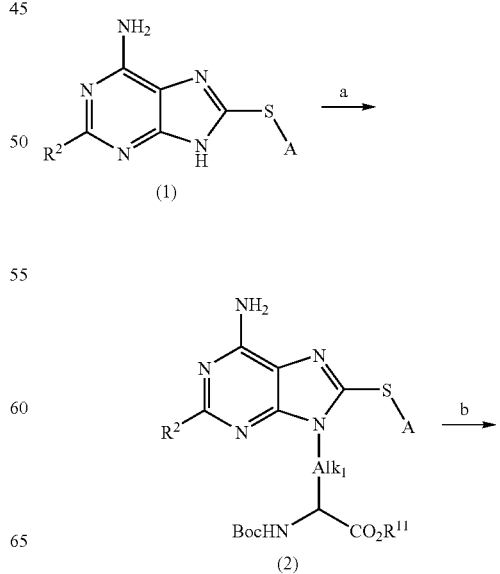

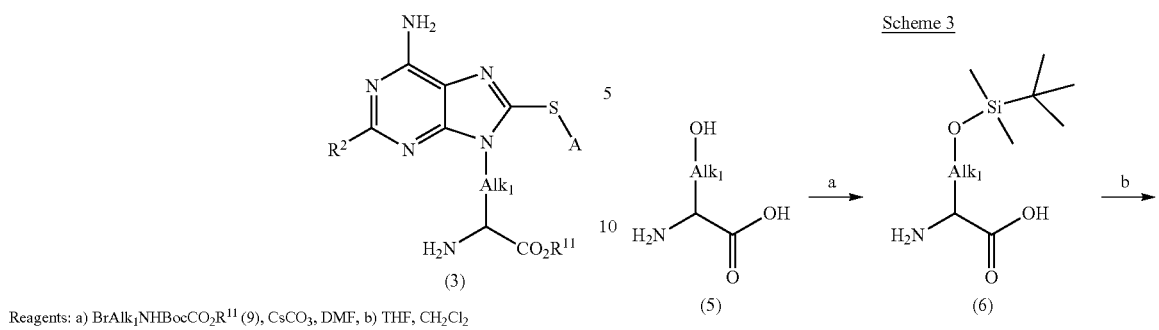

Thus, an 8-sulphanylaryladenine of formula (1) may be alkylated with a bromoalkylamino ester of general formula (9) in the presence of inorganic base such as potassium or caesium hydroxide in an aprotic solvent such as DMF to give intermediate carbamates of general formula (2). Treatment of the carbamate (2) under acid conditions such as trifluoroacetic acid leads to the amino esters of general formula (3).

In another aspect of the invention acids of general formula (4) may be prepared by the hydrolysis of esters of formula (3) by employing a mineral base such as lithium or sodium hydroxide in aqueous conditions with an organic co-solvent such as ethyl alcohol, as depicted in Scheme 2.

In another aspect to the invention, amino acid esters of general formula (9) used as alkylating agents in Scheme-1, may be prepared by methods-set-out in Scheme 3.

In another aspect of the invention, alkyl substituted purine derivatives of general formula (10) may be prepared by, but not restricted to, the methods outlined in Scheme 4 below. In Scheme 4, $R^2$, $Alk^1$, A and $R^{11}$ are as defined herein.

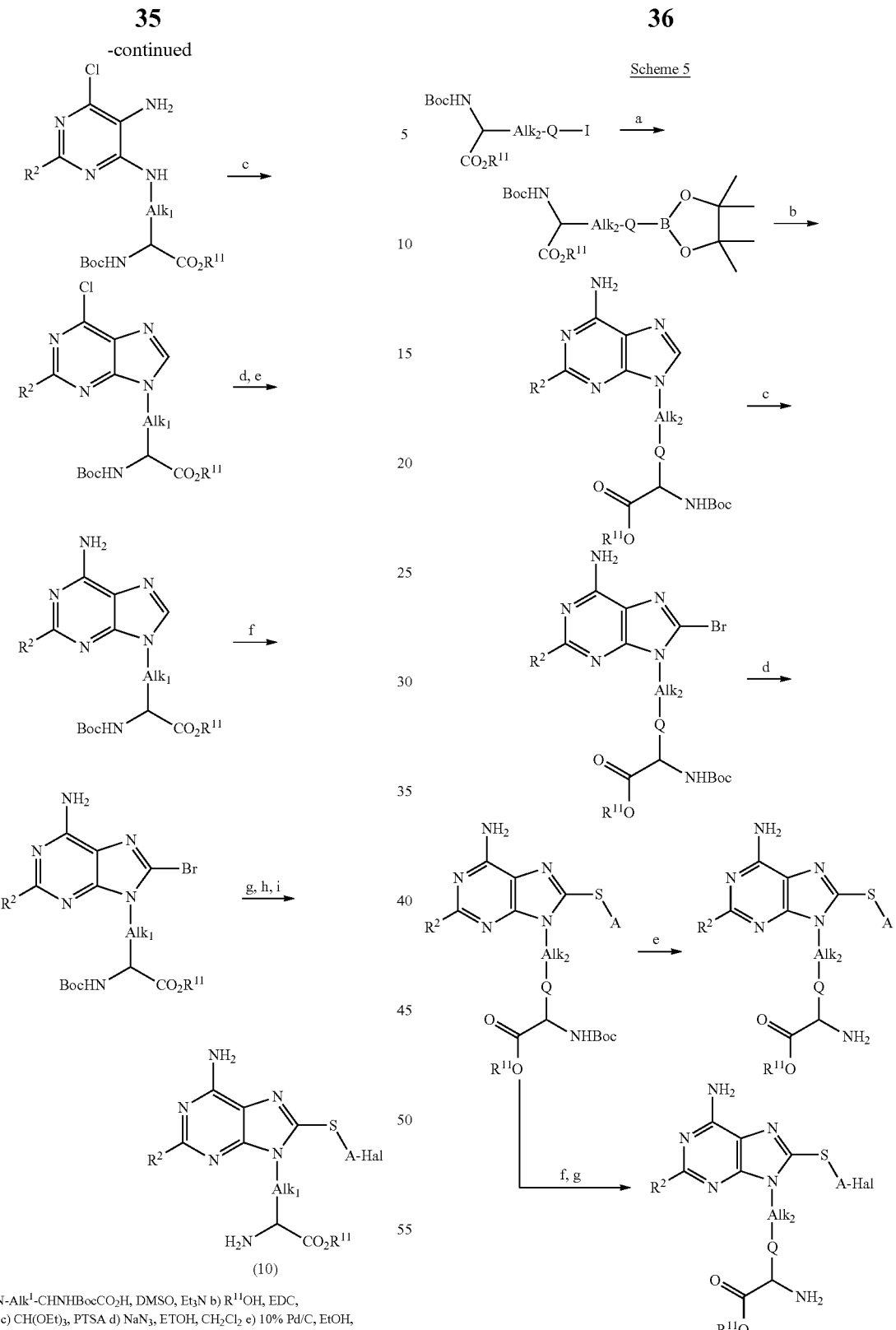

Reagents: a) H$_2$N-Alk$^1$-CHNHBocCO$_2$H, DMSO, Et$_3$N b) R$^{11}$OH, EDC, DMAP, CH$_2$Cl$_2$ c) CH(OEt)$_3$, PTSA d) NaN$_3$, ETOH, CH$_2$Cl$_2$ e) 10% Pd/C, AcOH, H$_2$ f) NBS, MeOH g) A—SH, Cs$_2$CO$_3$, DMF h) N-halosuccinimide i) TFA, CH$_2$Cl$_2$ Reagents: a) Bispinacolatodiboron, PdCl$_2$(dppf), KOAc, DMSO b) Adenine, Cu(OAc)2, TMEDA, MeOH c) NBS, MeCN d) A—SH, Cs$_2$CO$_3$, DMF e) TFA, CH$_2$Cl$_2$ f) N-halosuccinimide, MeCN, g) TFA, CH$_2$Cl$_2$ In another aspect of the invention, arylalkyl substituted purine derivates of general formula (11) may be prepared by, but not restricted to, the methods outlined in Scheme 5 below. In Scheme 5 R$^2$, Q, Alk$^2$, A and R$^{11}$ are as defined herein.

Broken Cell Assay

In order to determine whether a compound containing a particular group R$^7$ is hydrolysable by one or more intracellular carboxylesterase enzymes to a —COOH group, the compound may be tested in the following assay:

Preparation of Cell Extract

U937 or HCT 116 tumour cells (~109) were washed in 4 volumes of Dulbeccos PBS (~1 litre) and pelleted at 525 g for 10 min at 4° C. This was repeated twice and the final cell pellet was resuspended in 35 ml of cold homogenising buffer (Trizma 10 mM, NaCl 130 mM, $CaCl_2$ 0.5 mM pH 7.0 at 25° C.). Homogenates were prepared by nitrogen cavitation (700 psi for 50 min at 4° C.). The homogenate was kept on ice and supplemented with a cocktail of inhibitors at final concentrations of:

Leupeptin 1 μM
Aprotinin 0.1 μM
E64 8 μM
Pepstatin 1.5 μM
Bestatin 162 μM
Chymostatin 33 μM After clarification of the cell homogenate by centrifugation at 525 g for 10 min, the resulting supernatant was used as a source of esterase activity and was stored at −80° C. until required.

Measurement of Ester Cleavage

Hydrolysis of esters to the corresponding carboxylic acids can be measured using the cell extract, prepared as above. To this effect cell extract (~30 μg/total assay volume of 0.5 ml) was incubated at 37° C. in a Tris-HCl 25 mM, 125 mM NaCl buffer, pH 7.5 at 25° C. At zero time the ester (substrate) was then added at a final concentration of 2.5 mM and the samples were incubated at 37° C. for the appropriate time (usually 0 or 80 min). Reactions were stopped by the addition of 3× volumes of acetonitrile. For zero time samples the acetonitrile was added prior to the ester compound. After centrifugation at 12000 g for 5 min, samples were analysed for the ester and its corresponding carboxylic acid at room temperature by LCMS (Sciex API 3000, HP1100 binary pump, CTC PAL). Chromatography was based on an AceCN (75*2.1 mm) column and a mobile phase of 5-95% acetonitrile in water/0.1% formic acid.

The table below presents data showing that several amino acid ester motifs, conjugated to various intracellular enzyme inhibitors by several different linker chemistries are all hydrolysed by intracellular carboxyesterases to the corresponding acid.

| Structure of amino acid ester conjugate | R | Linker |
|---|---|---|
| 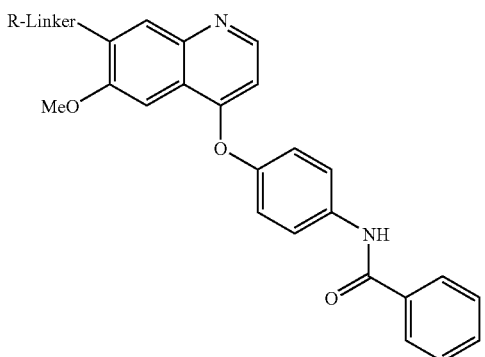 | 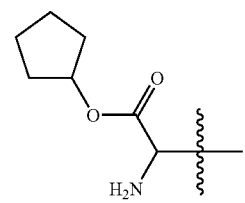 | —CH2CH2O— |
| 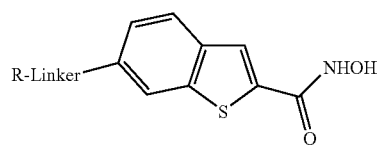 | 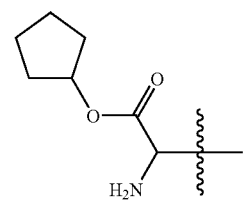 | —(CH₂)₃O—⌬—CH₂NHCH₂— |
| 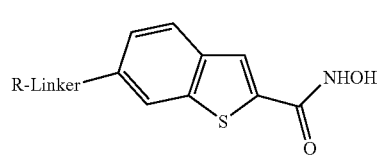 | 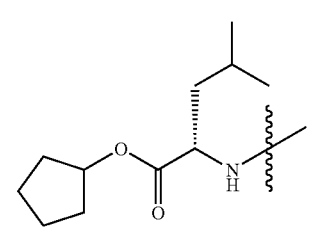 | —CH₂—⌬—CH₂NHCH₂— |
| 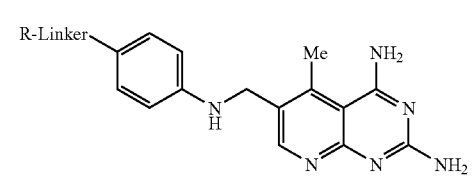 | 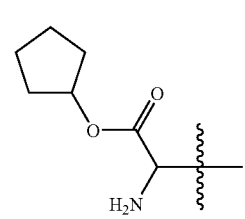 | —CH2CH2O— |

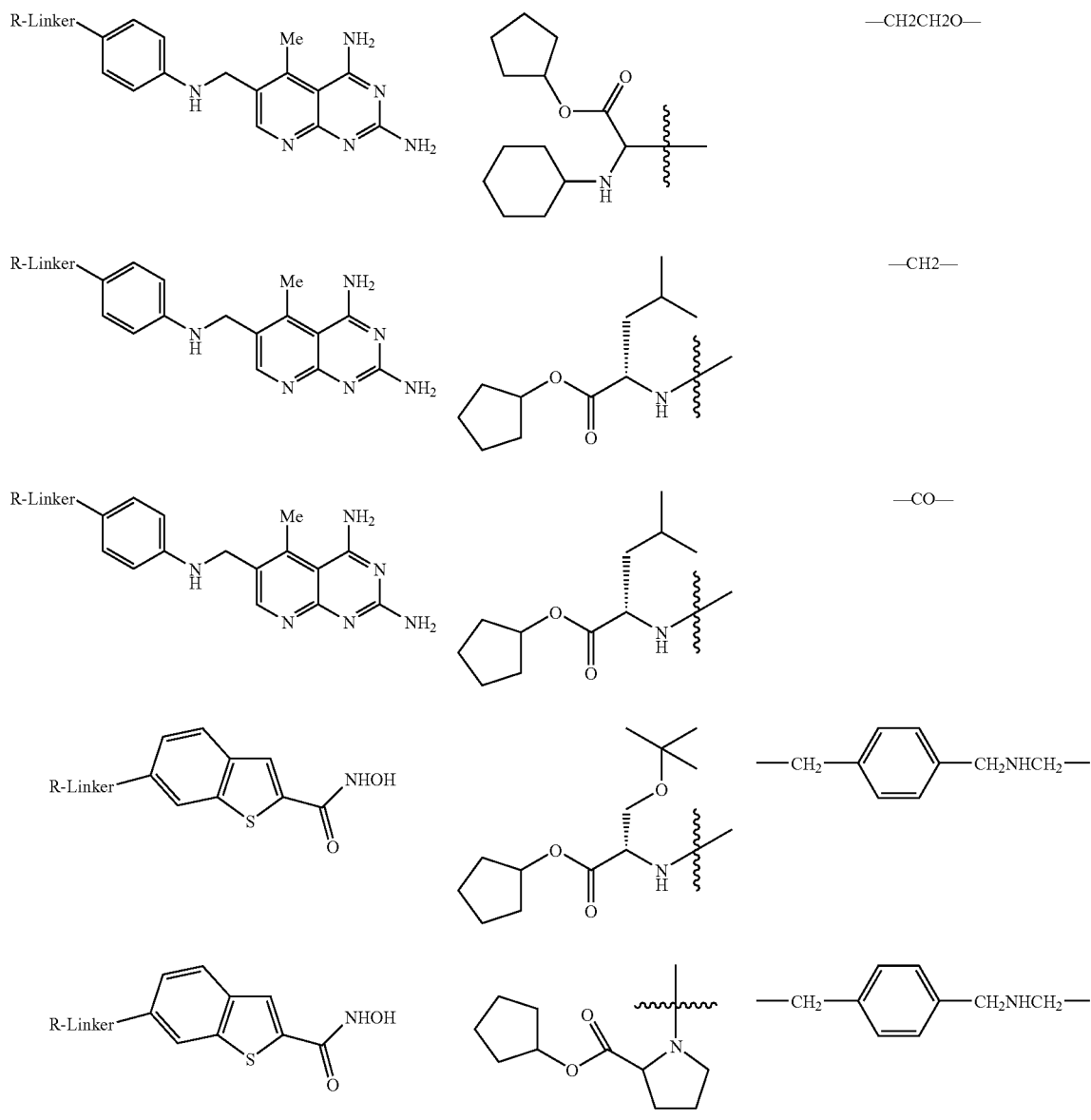

-continued

| | | |
|---|---|---|
| 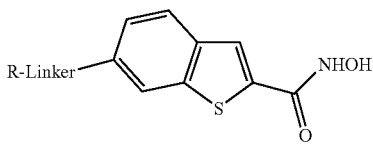 | 1000-50000 | WO2006117548 |
| 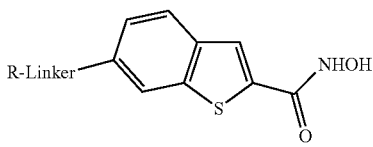 | >50000 | WO2006117549 |
| 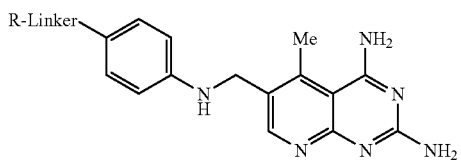 | >50000 | WO2006117567 |
| 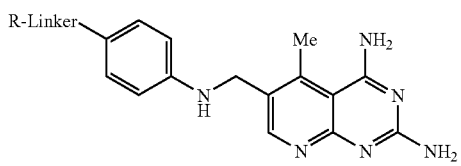 | 1000-50000 | WO2006117567 |
| 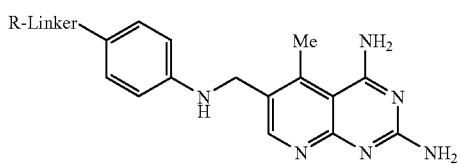 | 1000-50000 | WO2006117567 |
| 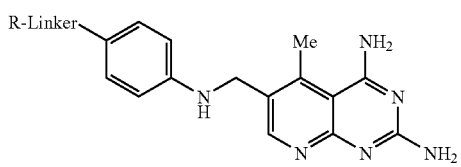 | >50000 | WO2006117567 |
| 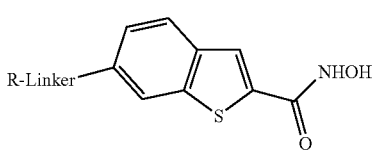 | >50000 | WO2006117549 |
| 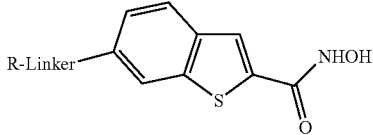 | >50000 | WO2006117549 |

EXAMPLES

Abbreviations

MeOH=methanol; EtOH=ethanol; EtOAc=ethyl acetate; Boc=tert-butoxycarbonyl; DCM=dichloromethane; DMF=dimethylformamide; DMSO=dimethyl sulfoxide; DMAP=dimethylamino pyridine; DEAD=diethylazodicarboxylate; EDC=1-ethyl-3-(3-dimethylaminopropyl)carbodiimide; TFA=trifluoroacetic acid; THF=tetrahydrofuran; $Na_2CO_3$=sodium carbonate; HCl=hydrochloric acid; DIPEA=diisopropylethylamine; NaH=sodium hydride; NaOH=sodium hydroxide; $NaHCO_3$=sodium hydrogen carbonate; Pd/C=palladium on carbon; EDC=1-ethyl-3-(3-dimethylaminopropyl)carbodiimide; ml=millilitre; g=gram(s); mg=milligram(s); mol=moles; mmol=millimole(s); Sat=saturated; LC/MS=high performance liquid chromatography/mass spectrometry; NMR=nuclear magnetic resonance.

Reagents and Apparatus

Commercially available reagents and solvents (HPLC grade) were used without further purification. Solvents were removed using a Buchi rotary evaporator. Purification of compounds by flash chromatography column was performed using silica gel, particle size 40-63 μm (230-400 mesh) obtained from Silicycle. Purification of compounds by preparative HPLC was performed on Gilson systems using reverse phase ThermoHypersil-Keystone Hyperprep HS C18 columns (12 μm, 100×21.2 mm), gradient 20-100% B (A=water/0.1% TFA, B=acetonitrile/0.1% TFA) over 9.5 min, flow=30 ml/min, injection solvent 2:1 DMSO:acetonitrile (1.6 ml), UV detection at 215 nm.

$^1$H NMR spectra were recorded on a Bruker 400 MHz AV spectrometer in deuterated solvents. Chemical shifts δ are in parts per million. Thin-layer chromatography (TLC) analysis was performed with Kieselgel 60 $F_{254}$ (Merck) plates and visualized using UV light.

Analytical HPLC/MS was performed on an Agilent HP1100 LC system using reverse phase Hypersil BDS C18 columns (5 μm, 2.1×50 mm), gradient 0-95% B (A=water/0.1% TFA, B=acetonitrile/0.1% TFA) over 2.10 min, flow=1.0 ml/min. UV spectra were recorded at 215 nm using a G1214A single wavelength UV detector. Mass spectra were obtained over the range m/z 150 to 850 at a sampling rate of 2 scans per second or 1 scan per 1.2 seconds using LC/MSD Quad SW ESI interface. Data were integrated and reported using OpenLynx and OpenLynx Browser software.

Intermediate 1: Cyclopentyl (S)-5-bromo-2-tert-butoxycarbonylaminopentanoate

The synthesis of cyclopentyl (S)-5-bromo-2-tert-butoxycarbonylaminopentanoic acid is outlined below in Scheme 6. Additional literature references relating to this route can be found within *J. Org. Chem.* 1984, 49, 3527-3534.

Scheme 6

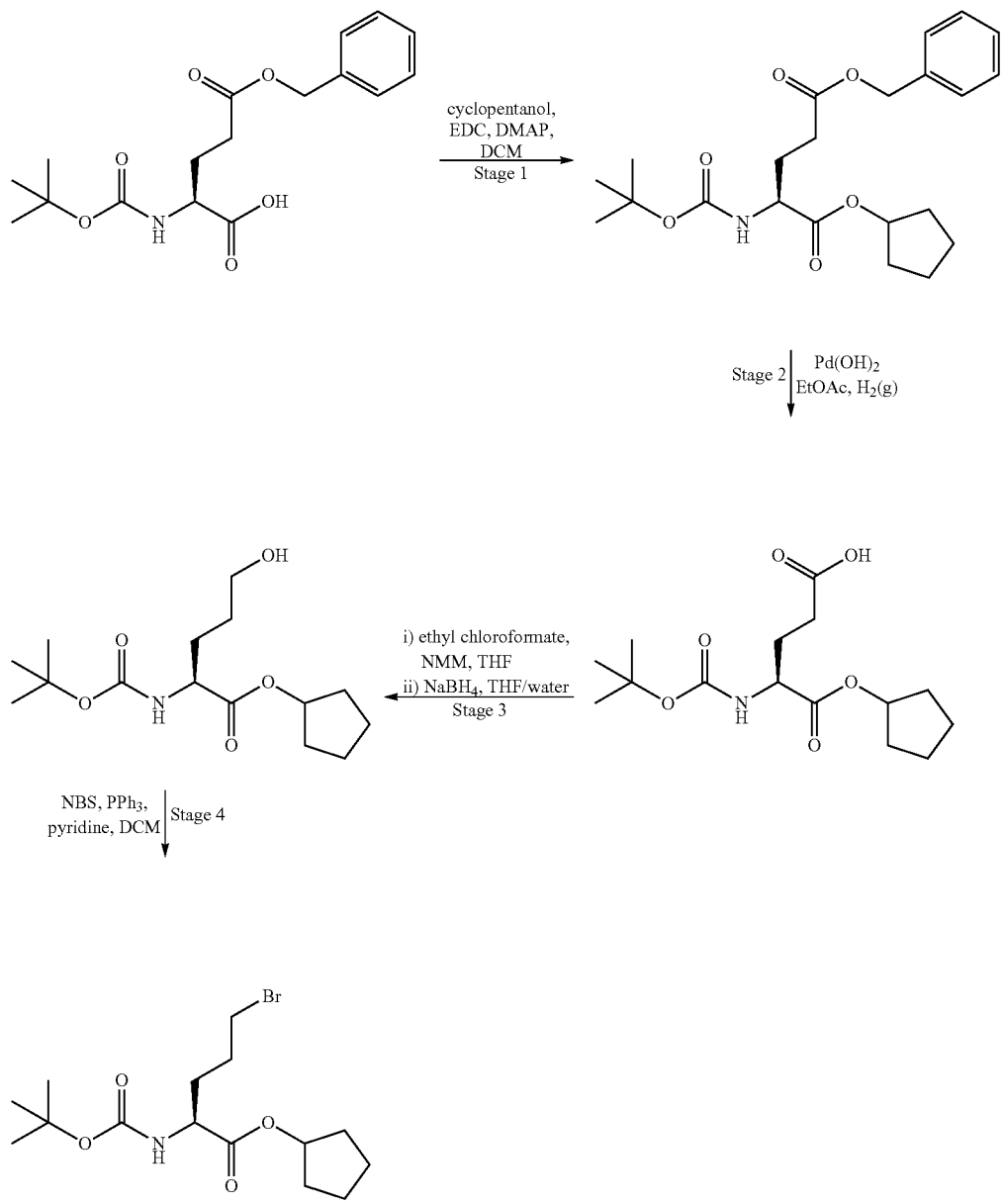

Stage 1: Cyclopentyl (S)-2-tert-Butoxycarbonylaminopentanedioic acid 5-benzyl ester 1-cyclopentyl ester

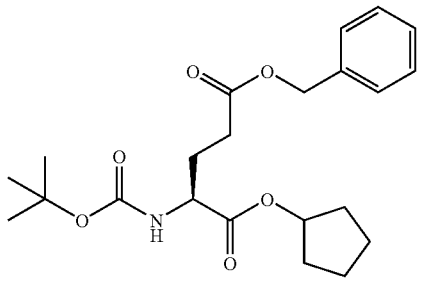

To a solution of Boc-L-Glu(OBzl)-OH (15 g, 44.5 mmol) in dichloromethane (220 ml) in an ice-bath, was added cyclopentanol (4.8 ml, 53.3 mmol, 1.2 eq), EDC (9.4 g, 48.9 mmol, 1.1 eq) and DMAP (543 mg, 4.4 mmol, 0.1 eq). The reaction mixture was allowed to warm to room temperature and stirred for 12 hours for complete reaction. The reaction mixture was diluted with DCM (200 ml) and washed with 1M HCl, 1M $Na_2CO_3$ and brine. The organic layer was then dried over magnesium sulphate and evaporated under reduced pressure. The product was purified by column chromatography using ethyl acetate/heptane (1:4) to afford the title compound as a white solid (12.4 g, 69%).

$^1$H NMR (300 MHz, $CDCl_3$) δ: 7.38 (5H, m), 5.70 (1H, m), 5.10 (2H, s), 5.05 (1H, m), 4.25 (1H, m), 2.47 (2H, m), 2.15 (1H, m), 1.95-1.55 (9H, m), 1.47 (9H, s).

Stage 2: (S)-2-tert-Butoxycarbonylamino-pentanedioic acid 1-cyclopentyl ester

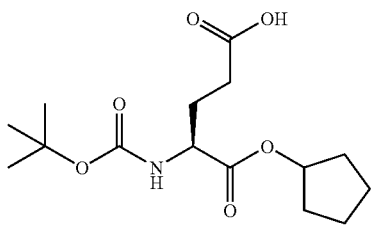

(S)-2-tert-Butoxycarbonylamino-pentanedioic acid 5-benzyl ester 1-cyclopentyl ester (12.4 g, 30.5 mmol) was dissolved in EtOAc (200 ml) and purged with nitrogen before addition of 20% $Pd(OH)_2$ on carbon catalyst (1.3 g). The reaction flask was then purged with hydrogen gas for a period of 5 minutes before leaving under a balloon of hydrogen for 5 hours for complete reaction. The catalyst was removed by filtration, washing with 50 ml EtOAc and the combined filtrates were evaporated under reduced pressure. The title compound was isolated as a clear oil (7.73 g, 85% yield) and required no further purification.

$^1$H NMR (300 MHz, $CDCl_3$) δ: 10.0 (1H, br s), 5.70 (2H, m), 4.28 (1H, m), 2.47 (2H, m), 2.15 (1H, m), 1.95-1.55 (9H, m), 1.47 (9H, s).

Stage 3: (S)-2-tert-Butoxycarbonylamino-5-hydroxy-pentanoic acid cyclopentyl ester

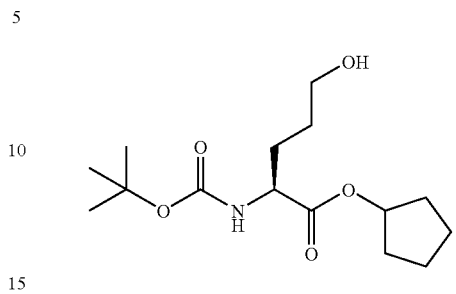

Ethyl chloroformate (2.45 ml, 25.6 mmol, 1.2 eq) was added at −20° C. to a stirred solution of (S)-2-tert-butoxycarbonylamino-pentanedioic acid 1-cyclopentyl ester (6.73 g, 21.4 mmol) and N-methyl morpholine (3.05 ml, 27.8 mmol, 1.3 eq) in THF (50 ml). The reaction mixture became very thick with precipitation of a white solid. The reaction was therefore diluted further with THF (100 ml) to aid mixing and left stirring at −20° C. for 2 hours. The precipitated mass was filtered off and the filtrate was added over a period of 20 minutes to a solution of sodium borohydride (2.43 g, 64.1 mmol, 3 eq) in THF (20 ml) and water (5 ml) at 0° C. The reaction mixture was allowed to stir to room temperature and left for 4 hours for complete reaction. The mixture was acidified to pH 5 with 1M HCl and the THF removed under reduced pressure. The aqueous solution was extracted with EtOAc (3×100 ml) and dried over magnesium sulphate. The product was purified by column chromatography (DCM-5% MeOH/DCM) and isolated as a clear oil (5.0 g, 78% yield).

$^1$H NMR (300 MHz, $CDCl_3$) δ: 5.20 (2H, m), 4.25 (1H, m), 3.65 (2H, m), 2.00-1.57 (12H, m), 1.47 (9H, s).

Stage 4: (S)-5-Bromo-2-tert-butoxycarbonylamino-pentanoic acid cyclopentyl ester

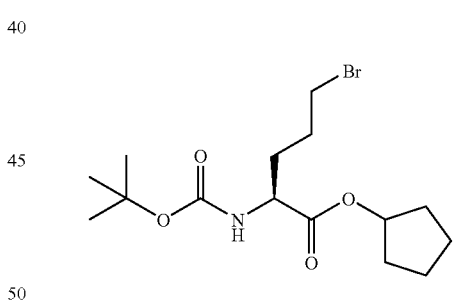

To a slurry of N-bromo succinimide (3.54 g, 19.9 mmol, 3 eq) in DCM (30 ml) was added a solution of triphenyl phosphine (4.87 g, 18.8 mmol, 2.8 eq) in DCM (15 ml). The solution was stirred for a further 5 minutes before addition of pyridine (644 μl, 7.96 mmol, 1.2 eq) and a solution of (S)-2-tert-butoxycarbonylamino-5-hydroxy-pentanoic-acid cyclopentyl ester (2.0 g, 6.64 mmol) in DCM (20 ml). The solution was stirred for 18 hours, concentrated in vacuo and the residual solvent azeotroped with toluene (3×30 ml). The residue was triturated with diethyl ether (30 ml) and ethyl acetate: heptane (1:9, 2×30 ml). The combined ether and ethyl acetate/heptane solutions was concentrated onto silica and purified by column chromatography using ethyl acetate/heptane (1:9 to 2:8) to provide the title compound as a clear oil (1.34 g, 55% yield).

$^1$H NMR (300 MHz, $CDCl_3$) δ: 5.25 (1H, m), 5.05 (1H, br d), 3.45 (2H, m), 2.00-1.55 (12H, m), 1.45 (9H, s).

Intermediate 2: Cyclopentyl (2S)-4-bromo-2-(tert-butoxycarbonylamino)butanoate The synthesis of cyclopentyl (2S)-4-Bromo-2-(tert-butoxycarbonylamino) butanoate is outlined below in Scheme 7.

Scheme 7

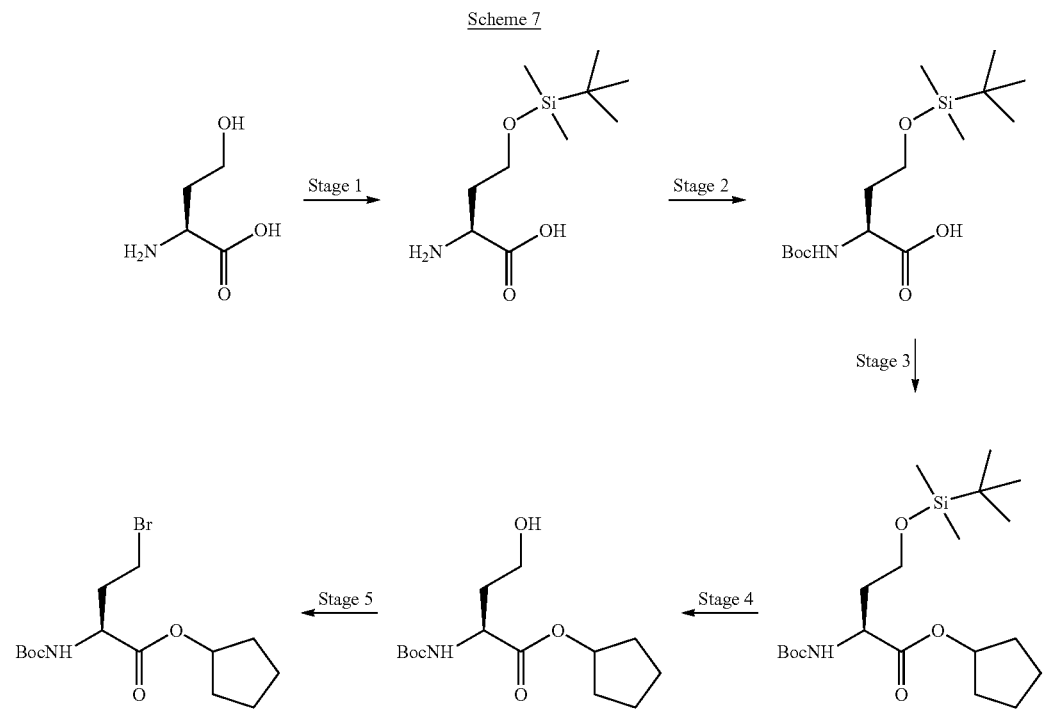

Stage 1: O-[tert-Butyl(dimethyl)silyl-L-homoserine

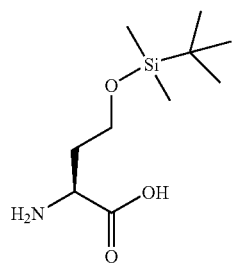

To a suspension of L-homoserine (1 g, 8.4 mmol) in acetonitrile (10 ml) at 0° C. was added 1,8-diazabicyclo[5.4.0]undec-7-ene (1.32 ml, 8.8 mmol, 1.05 eq). tert-butyldimethylsilyl chloride (1.33 g, 8.8 mmol, 1.05 eq) was then added portionwise over 5 minutes and the reaction mixture allowed to warm to room temperature and stirred for 16 hours. A white precipitate formed, which was filtered off and washed with acetonitrile before drying under reduced pressure. The title compound was isolated as a white solid (1.8 g, 92% yield). $^1$H NMR (500 MHz, DMSO-$d_6$), δ: 7.5 (1H, br s), 3.7 (1H, m), 3.35 (4H, br m), 1.95 (1H, m), 1.70 (1H, m), 0.9 (9H, s), 0.1 (6H, s).

Stage 2: N-(tert-Butoxycarbonyl)-O-[tert-butyl(dimethyl)silyl-L-homoserine

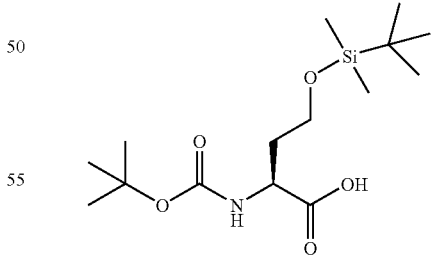

A suspension of stage 1 (Scheme 7) product (1.8 g, 7.7 mmol) in DCM (100 ml) at 0° C. was treated with triethylamine (2.15 ml, 15.4 mmol, 2 eq) and di-tert-butyl dicarbonate (1.77 g, 8.1 mmol, 1.05 eq). The reaction-mixture was stirred at room temperature for 16 hours. The DCM was removed under reduced pressure and the mixture was treated with ethyl acetate/brine. The ethyl acetate layer was dried over magnesium sulphate and evaporated under reduced pressure. The crude product was taken forward without further purification (2.53 g, 99% yield). ¹H NMR (500 MHz, CDCl₃), δ: 7.5 (1H, br s), 5.85 (1H, d, J=6.5 Hz), 4.3 (1H, m), 3.75 (2H, m), 1.95 (2H, m), 1.40 (9H, s), 0.85 (9H, s), 0.1 (6H, s).

Stage 3: Cyclopentyl N-(tert-butoxycarbonyl)-O-[tert-butyl(dimethyl)silyl-L-homo serinate

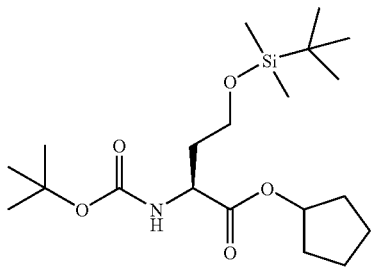

To a solution of Stage 2 (Scheme 7) product (2.53 g, 7.6 mmol) in DCM (50 ml) at 0° C. was added cyclopentanol (1.39 ml, 15.3 mmol, 2 eq), EDC (1.61 g, 8.4 mmol, 1.1 eq) and DMAP (93 mg, 0.76 mmol, 0.1 eq). The reaction mixture was stirred for 16 hours at room temperature before evaporation under reduced pressure. The crude residue was dissolved in ethyl acetate (100 ml) and washed with 1M HCl, 1M Na₂CO₃ and brine. The organic layer was then dried over magnesium sulphate and evaporated under reduced pressure. The product was purified by column chromatography using ethyl acetate/heptane (1:4) to give 2.24 g, 73% yield of title compound. m/z 402 [M+H]⁺. ¹H NMR (250 MHz, CDCl₃), δ: 5.2 (1H, d, J=6.3 Hz), 5.15 (1H, m), 4.2 (1H, m), 3.6 (2H, m), 2.0 (1H, m), 1.95-1.55 (9H, br m), 1.4 (9H, s), 0.85 (9H, s), 0.1 (6H, s).

Stage 4: Cyclopentyl N-(tert-butoxycarbonyl)-L-homoserinate

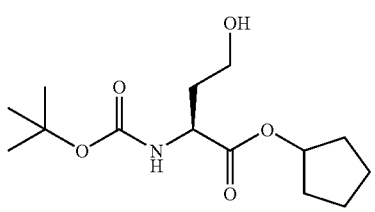

Stage 3 (Scheme 7) product (1.57 g, 3.9 mmol) was dissolved in acetic acid:THF:water (3:1:1, 100 ml). The reaction mixture was stirred at 30° C. for 16 hours. Ethyl acetate (200 ml) was added and washed with 1M Na₂CO₃, 1M HCl and brine. The ethyl acetate layer was dried over magnesium sulphate and concentrated under reduced pressure to give the product as a clear oil which crystallised on standing (1.00 g, 95% yield). m/z 310 [M+Na]⁺. ¹H NMR (250 MHz, CDCl₃), δ: 5.4 (1H, d, J=6.5 Hz), 5.2 (1H, m), 4.4 (1H, m), 3.65 (2H, m), 2.15 (1H, m), 1.9-1.55 (9H, br m), 1.45 (9H, s).

Stage 5: Cyclopentyl (2S)-4-bromo-2-(tert-butoxycarbonylamino)butanoate

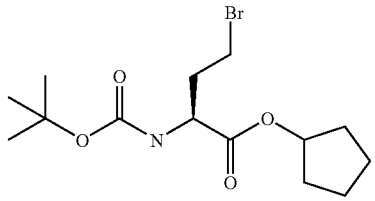

To a slurry of N-bromosuccinimide (1.86 g, 10.4 mmol) in DCM (16.2 ml) was added a solution of triphenylphosphine (2.56 g, 9.74 mmol) in DCM (7.2 ml). The solution was stirred for a further 5 minutes after addition. Pyridine (338 µl, 4.18 mmol) was added, followed by a solution of Stage 4 product (Scheme 7) (1.00 g, 3.48 mmol) in DCM (8.8 ml). The solution was stirred for 18 hours, concentrated under reduced pressure and the residual solvent azeotroped with toluene (3×16 ml). The residue was triturated with diethyl ether (10 ml) and ethyl acetate:heptane (1:9, 2×10 ml). The combined ether and heptane solutions was concentrated onto silica and purified by column chromatography using ethyl acetate/heptane (1:9 to 2:8) to provide 1.02 g (84% yield) of title compound. ¹H NMR (300 MHz, CDCl₃), δ: 5.30-5.05 (2H, m), 4.45-4.30 (1H, m), 3.45 (2H, t, J=7.3 Hz), 2.50-2.30 (1H, m), 2.25-2.10 (1H, m), 1.95-1.60 (8H, br m), 1.47 (9H, s).

Intermediate 3: Cyclopentyl (R)-5-bromo-2-tert-butoxycarbonylaminopentanoate

Synthesised via analogous methods to Intermediate 1 starting from 5-benzyl 1-cyclopentyl N-(tert-butoxycarbonyl)-D-glutamate. (Boc-D-Glu(OBzl)-OH).

Intermediate 4: Cyclopentyl (2S)-4-bromo-2-(tert-butoxycarbonylamino butanoate

Synthesised via analogous methods to Intermediate 2 starting from D-homoserine.

Intermediate 5: tert-butyl 5-bromo-N-{[2-(trimethylsilyl)ethoxy]carbonyl}-L-norvalinate The synthesis of tert-butyl 5-bromo-N-{[2-(trimethylsilyl)ethoxy]carbonyl}-L-norvalinate is outlined below in Scheme 8.

Scheme 8

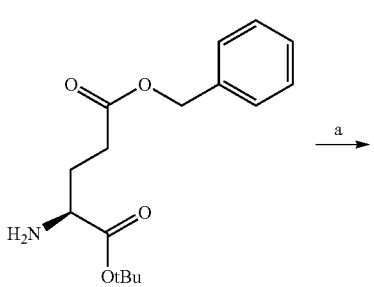

-continued

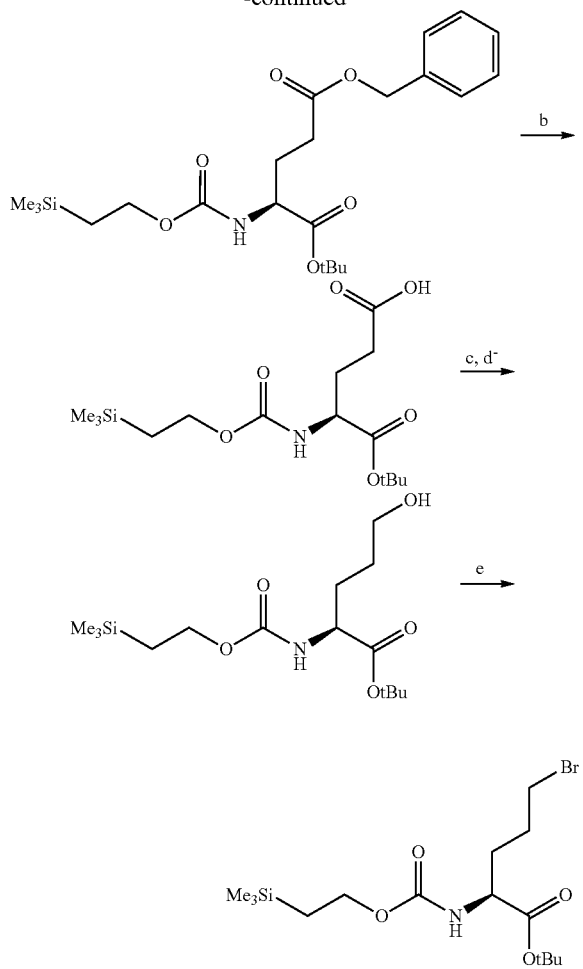

Stage 1: 5-benzyl 1-tert-butyl N-{[2-(trimethylsilyl)ethoxy]carbonyl}-L-glutamate

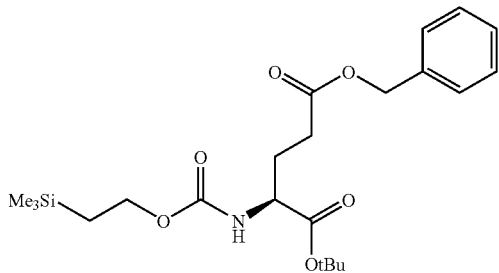

5-Benzyl 1-tert-butyl L-glutamate hydrochloride (1.156 g, 3.51 mmol) in water (4 ml) was added to a stirred solution of triethylamine (1.232 ml, 8.76 mmol) in dioxane (4 ml). The resulting solution was treated with 1-[2-(trimethylsilyl)ethoxycarbonyloxy]pyrrolidin-2,5-dione[TEOC.OSu] (1 g, 3.86 mmol) and stirred at room temp for 24 h. The mixture was diluted with water (50 ml), acidified with solid NaHSO₄ and extracted with ether (3×60 ml). The combined organic phases were washed with water (3×100 ml) and brine (100 ml), dried (MgSO₄) and evaporated to give 5-benzyl 1-tert-butyl N-{[2-(trimethylsilyl)ethoxy]carbonyl}-L-glutamate (1.67 g) as a clear colourless oil. m/z 438 (M+H)⁺

Stage 2: (4S)-5-tert-butoxy-5-oxo-4-({[2-(trimethylsilyl)ethoxy]carbonyl}amino) pentanoic acid

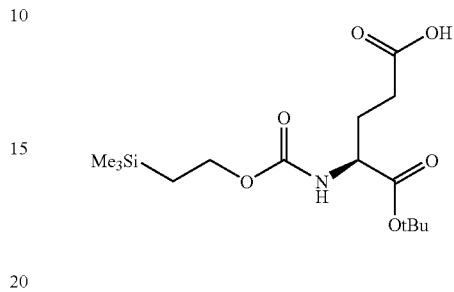

Benzyl 1-tert-butyl N-{[2-(trimethylsilyl)ethoxy]carbonyl}-L-glutamate (1.67 g, 3.82 mmol) and palladium-hydroxide 20% C (150 mg, 3-3.82 mmol) were purged with N₂, then EtOH (35 ml) was added. Hydrogen gas was bubbled through the resulting mixture, which was subsequently stirred under a balloon of H₂ for 1 h. The mixture was therefore purged with N₂, filtered through a pad of Celite and evaporated to afford (4S)-5-tert-butoxy-5-oxo-4-({[2-(trimethylsilyl)ethoxy]carbonyl}amino) pentanoic acid (1.33 g) as a clear colourless oil.

Stage 3: tert-Butyl 5-hydroxy-N-{[2-(trimethylsilyl)ethoxy]carbonyl}-L-norvalinate

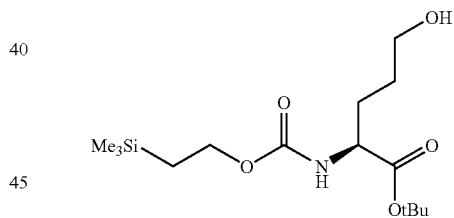

Ethyl chloroformate (0.441 ml, 4.59 mmol) was added slowly to a stirred solution of (4S)-5-tert-butoxy-5-oxo-4-({[2-(trimethylsilyl)ethoxy]carbonyl}amino) pentanoic acid (1.33 g, 3.83 mmol) and N-methylmorpholine (0.547 ml, 4.98 mmol) in THF (10 ml) at −20° C. A thick white solid precipitated from the solution and hindered stirring. THF (ca. 4 ml) was added to mobilise the suspension. The resulting mixture was stirred at −20° C. for 30 min, then allowed to warm slowly to 0° C. over the course of 2 h. The mixture was therefore stirred at 0° C. for a further 1 h. The slurry was filtered and the filtrate added portion wise over 30 min to a stirred solution of sodium borohydride (0.434 g, 11.48 mmol) in THF (4 ml) and water (1 ml) at 0° C. The mixture was quenched with NH₄Cl solution, diluted with Et₂O (50 ml) and the phases separated. The aqueous phase was extracted with Et₂O (25 ml) and the combined organic phases were washed with NaHCO₃ solution (25 ml) and brine (25 ml), dried (MgSO₄) and evaporated to give tert-Butyl 5-hydroxy-N-{[2-(trimethylsilyl)ethoxy]carbonyl}-L-norvalinate (1.24 g) as a clear colourless oil.

Stage 4: tert-Butyl 5-bromo-N-{[2-(trimethylsilyl)ethoxy]carbonyl}-L-norvalinate

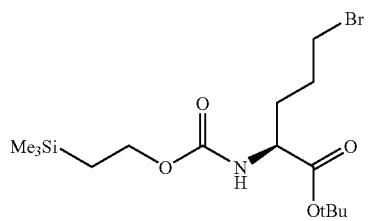

A solution of N-bromosuccinimide (2.129 g, 11.96 mmol) in DCM (10 ml) was treated with triphenylphosphine (2.93 g, 11.17 mmol) in DCM (10 ml), followed by pyridine (0.387 ml, 4.79 mmol) and tert-butyl 5-hydroxy-N-{[2-(trimethylsilyl)ethoxy]carbonyl}-L-norvalinate (1.33 g, 3.99 mmol) in DCM (5 ml). The resulting black mixture was stirred at room temp for 24 h. The mixture was pre-absorbed onto SiO₂ and purified by chromatography (silica gel, 0-5-10-20% Et₂O/isohexane) to afford tert-Butyl 5-bromo-N-{[2-(trimethylsilyl)ethoxy]carbonyl}-L-norvalinate Intermediate 5 (1.1 g) as a colourless oil.

Example 1

(S)-Cyclopentyl 2-amino-5-(6-amino-8-(6-iodobenzo[d][1,3]dioxol-5-ylthio)-9H-purin-9-yl)pentanoate

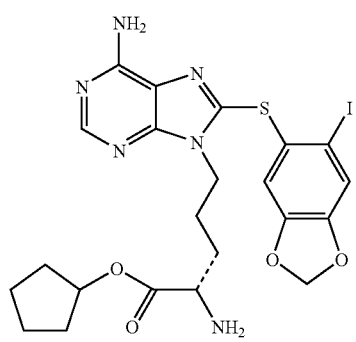

Cesium carbonate (0.36 g, 1.09 mmol) and Intermediate 1 ((S)-cyclopentyl 4-bromo-2-(tert-butoxycarbonylamino)pentanoate) (0.40 g, 1.09 mmol) were added to a suspension of 8-(6-iodobenzo[d][1,3]dioxol-5-ylthio)-9H-purin-6-amine [J. Med. Chem 2006, 49, 817-828] (0.30 g, 0.73 mmol) in dimethylformamide (3 ml). After stirring at 50° C. for 12 h the reaction mixture was concentrated in vacuo. Dichloromethane (1 ml) and trifluoroacetic acid (0.5 ml) were added to the residue. After stirring for 12 h at r.t. the solvents were removed in vacuo and the crude residue was purified by preparative HPLC to afford the title compound (22 mg) as an off white solid. m/z 597 [M+H]⁺, 595 [M−H]⁻. ¹H NMR (400 MHz, CDCl₃), δ: 8.3 (1H, s), 7.3 (1H, s); 6.9 (1H, s), 6.0 (2H, s), 5.6 (2H, bs), 5.2 (1H, m), 4.2 (2H, m), 3.5 (2H, d), 3.4 (1H, m), 2.0-1.5 (12H, m).

Example 2

(S)-cyclopentyl 2-amino-4-(6-amino-8-(6-iodobenzo[d][1,3]dioxol-5-ylthio)-9H-purin-9-yl)butanoate

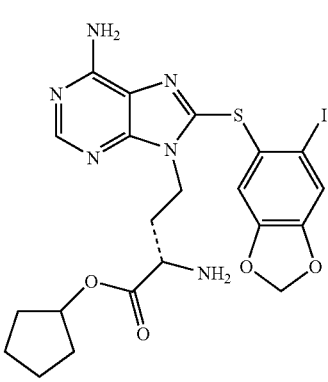

Cesium carbonate (0.36 g, 1.09 mmol) and Intermediate 2 ((S)-cyclopentyl 4-bromo-2-(tert-butoxycarbonylamino)butanoate) (0.38 g, 1.09 mmol) were added to a suspension of 8-(6-iodobenzo[d][1,3]dioxol-5-ylthio)-9H-purin-6-amine [J. Med. Chem 2006, 49, 817-828] (0.30 g, 0.73 mmol) in dimethylformamide (3 ml). After stirring at 50° C. for 12 h the reaction mixture was concentrated in vacuo. Dichloromethane (1 ml) and trifluoroacetic acid (0.5 ml) were added to the residue. After stirring for 12 h the solvents were removed in vacuo and the crude residue was purified by preparative HPLC to afford the title compound (20 mg) as an off white solid. m/z 583 [M+H]⁺, 581 [M−H]⁻. ¹H NMR (500 MHz, CDCl₃), δ: 8.3 (1H, s), 7.3 (1H, s), 6.9 (1H, s), 6.0 (2H, s), 5.7 (2H, bs), 5.1 (1H, m), 4.4 (2H, m), 3.4 (1H, m), 2.3 (1H, m), 2.0-1.6 (9H, m).

The following Examples were prepared in a similar manner to the compounds of Examples 1 and 2:

Example 3

(R)-Cyclopentyl 2-amino-5-(6-amino-8-(6-iodobenzo[d][1,3]dioxol-5-ylthio)-9H-purin-9-yl)pentanoate

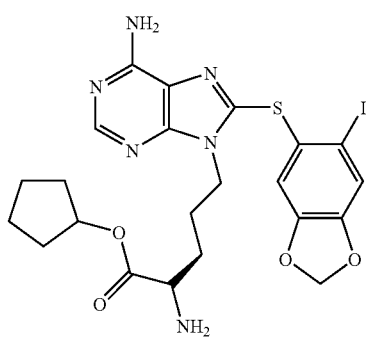

From 8-(6-iodobenzo[d][1,3]dioxol-5-ylthio)-9H-purin-6-amine [J. Med. Chem 2006, 49, 817-828] (0.19 g, 0.42 mmol), Intermediate 3 (0.18 g, 0.49 mmol) and caesium carbonate (0.27 g, 0.82 mmol) to give the title compound to give the intermediate N-Boc derivative followed by treatment with TFA (2 mL) in dichloromethane (4 mL) to give the title compound (0.02 g) as a colourless solid. m/z 597 [M+H]$^+$. $^1$H NMR (400 MHz, CHCl$_3$-d) δ: 8.31 (1H, s), 7.29 (1H, s), 6.89 (1H, s), 5.98 (2H, s), 5.55 (2H, br s), 5.18 (1H, m), 4.21 (2H, m), 3.41 (1H, m), 1.9-1.75 (7H, br m), 1.73-1.45 (7H, br m).

Example 4

(R)-cyclopentyl 2-amino-4-(6-amino-8-(6-iodobenzo[d][1,3]dioxol-5-ylthio)-9H-purin-9-yl)butanoate

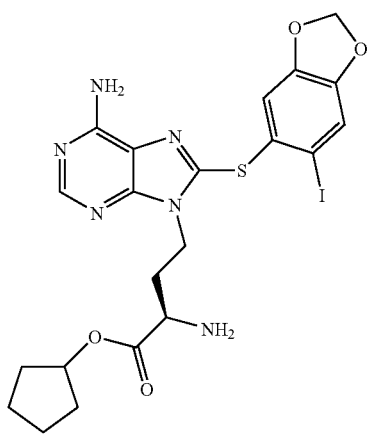

From 8-(6-iodobenzo[d][1,3]dioxol-5-ylthio)-9H-purin-6-amine [J. Med. Chem 2006, 49, 817-828] (0.22 g, 0.48 mmol), Intermediate 4 (0.2 g, 0.57 mmol) and caesium carbonate (0.31 g, 0.96 mmol) to give the title compound to give the intermediate N-Boc derivative followed by treatment with TFA (2 mL) in dichloromethane (4 mL) to give the title compound (0.02 g) as a colourless solid. m/z 583 [M+H]$^+$. $^1$H NMR (400 MHz, CHCl$_3$-d) δ: 8.31 (1H, s), 7.30 (1H, s), 6.91 (1H, s), 5.98 (2H, s), 5.54 (2H, br. s), 5.09-5.14 (1H, m), 4.40 (2H, t, J=6.6 Hz), 3.35 (1H, dd, J=9.5, 4.2 Hz), 2.25 (1H, dd, J=13.7, 4.4 Hz), 1.87-1.96 (1H, m), 1.82 (3H, m), 1.59-1.70 (11H, m).

Example 5

(S)-tert-Butyl 2-amino-5-(6-amino-8-(6-iodobenzo[d][1,3]dioxol-5-ylthio)-9H-purin-9-yl)pentanoate

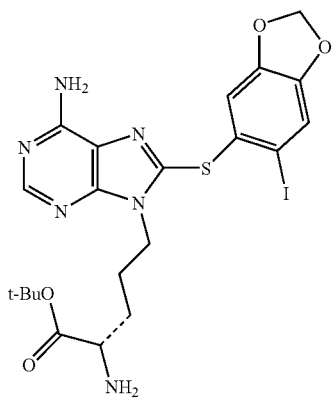

8-(6-iodobenzo[d][1,3]dioxol-5-ylthio)-9H-purin-6-amine (0.2 g, 0.48 mmol) [J. Med. Chem 2006, 49, 817-828] was dissolved in DMF (2 ml) and treated with cesium carbonate (0.3 g, 0.97 mmol), followed by Intermediate 5 (0.23 g, 0.58 mmol) in DMF (1 ml) and the resulting mixture heated at 50° C. for 4 h. The mixture was therefore partitioned between EtOAc (50 ml) and water (50 ml) and the phases separated. The organic phase was washed with water (25 ml) and brine (4×25 ml), dried (MgSO$_4$) and evaporated to give a dark brown oil. Purification (silica gel, 0-20% MeOH/DCM) afforded the TEOC-protected intermediate as a yellow solid (106 mg). The solid was dissolved in THF (2 ml) and cooled to 0° C. TBAF (1M in THF) (968 μl, 0.968 mmol) was added slowly and the resulting yellow-orange solution stirred at room temp for 2 h. LC-MS analysis showed complete conversion to the product. The mixture was therefore partitioned between EtOAc (50 ml) and water (50 ml) and the phases separated. The organic phase was washed with 50% saturated NH$_4$Cl solution (2×25 ml), NaHCO$_3$ solution (25 ml) and brine (25 ml), dried (MgSO$_4$) and evaporated to give the crude product (73 mg) as a pale yellow solid. The product was isolated by preparative HPLC to afford the title compound (15 mg) as a pale yellow solid. m/z 585 [M+H]$^+$. $^1$H NMR (400 MHz, CHCl$_3$-d) d: 8.31 (1H, s), 7.23 (1H, s), 6.88 (1H, s), 5.97 (2H, s), 5.54 (2H, br. s), 4.23 (2H, t, J=7.3 Hz), 3.32 (1H, dd, J=7.6, 5.1 Hz), 1.90 (2H, m), 1.70 (1H, m), 1.74 (4H, m), 1.42 (9H, s).

Example 6

Cyclopentyl 3-{6-amino-8-[(6-iodo-1,3-benzodioxol-5-yl)thio]-9H-purin-9-yl}-L-alaninate

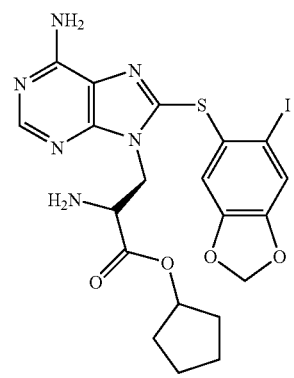

A solution of cyclopentyl 3-{6-amino-8-[(6-iodo-1,3-benzodioxol-5-yl)thio]-9H-purin-9-yl}-N-(tert-butoxycarbonyl)-L-alaninate (21 mg, 0.027 mmol) in TFA (250 μl, 3.24 mmol) and DCM (1 ml) was stirred at room temp for 2 h. LC-MS analysis showed complete formation of the product. The solvent was evaporated and the residue purified on SCX (0.5 g) to afford the title compound (12 mg) as a pale yellow solid. m/z 569 [M+H]$^+$. $^1$H NMR (400 MHz, CHCl$_3$-d) d: 8.31 (1H, s), 7.23 (1H, s), 6.93 (1H, s), 5.97 (2H, s), 5.61 (2H, br. s), 5.13 (1H, m), 4.50 (1H, dd, J=14.2, 5.9 Hz), 4.33 (1H, dd, J=113.9, 8.6 Hz), 3.98 (1H, dd, J=8.8, 5.9 Hz), 1.8-1.54 (10H, br m).

The cyclopentyl 3-{6-amino-8-[(6-iodo-1,3-benzodioxol-5-yl)thio]-9H-purin-9-yl}-N-(tert-butoxycarbonyl)-L-alaninate used as starting material in the above example was prepared as follows:

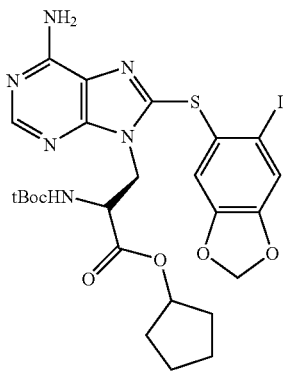

A mixture of cyclopentyl 3-{6-amino-8-[(1,3-benzodioxol-5-yl)thio]-9H-purin-9-yl}-N-(tert-butoxycarbonyl)-L-alaninate (39 mg, 0.072 mmol) and N-iodosuccinimide (97 mg, 0.431 mmol) was dissolved in acetonitrile (2 ml) and stirred at room temp for 18 h. The mixture was partitioned between EtOAc (25 ml) and 10% sodium thiosulfate solution (25 ml) and the phases separated. The organic phase was washed with 10% sodium thiosulfate solution (25 ml) and brine (25 ml), dried (MgSO$_4$) and evaporated. Purification (silica gel, 2% MeOH/DCM) afforded the desired material (24 mg) as a yellow solid. m/z 669 (M+H)$^+$ 667.

The cyclopentyl 3-{6-amino-8-[(1,3-benzodioxol-5-yl)thio]-9H-purin-9-yl}-N-(tert-butoxycarbonyl)-L-alaninate used as starting material in the above process was prepared as follows:

A mixture of cyclopentyl 3-(6-amino-8-bromo-9H-purin-9-yl)-N-(tert-butoxycarbonyl)-L-alaninate (0.27 g, 0.57 mmol), 3,4-methylenedioxythiophenol (0.35 mg, 2.28 mmol) and cesium carbonate (927 mg, 2.84 mmol) was dissolved in DMF (8 ml) and heated at 50° C. for 3 h. The mixture was diluted with EtOAc (100 ml) and washed with water (2×50 ml) and brine (4×50 ml), dried (MgSO$_4$) and evaporated to give the crude product as a sticky tan solid. Purification (silica gel, 2% MeOH/DCM) afforded the desired material (57 mg, 0.099 mmol, 17.36% yield) as a pale yellow solid.

The cyclopentyl 3-(6-amino-8-bromo-9H-purin-9-yl)-N-(tert-butoxycarbonyl)-L-alaninate used in the above process was prepared as follows:

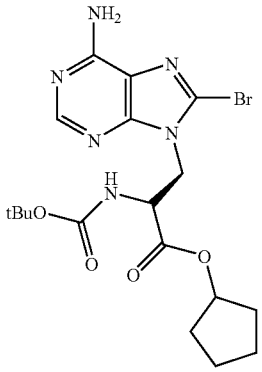

Cyclopentyl 3-(6-amino-9H-purin-9-yl)-N-(tert-butoxycarbonyl)-L-alaninate (267 mg, 0.68 mmol) and N-bromosuccinimide (243 mg, 1.37 mmol) were dissolved in MeCN (10 ml) and the resulting solution heated at 60° C. for 18 h. Additional N-bromosuccinimide (243 mg, 1.37 mmol) was added and heating continued for 24 h. The solvent was evaporated and the residue purified-(silica gel, 2-5% MeOH/DCM) to afford the desired material (160 mg) as a dark brown solid. m/z 469 (M+H)$^+$ The cyclopentyl 3-(6-amino-9H-purin-9-yl)-N-(tert-butoxycarbonyl)-L-alaninate used in the above process was prepared as follows:

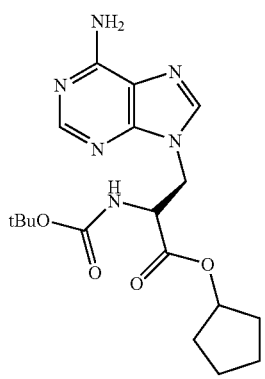

Cyclopentyl 3-(6-azido-9H-purin-9-yl)-N-(tert-butoxycarbonyl)-L-alaninate (25 mg, 0.060 mmol) was dissolved in a mixture of EtOH (2 ml) and acetic acid (200 μl). 10% palladium on carbon (5 mg) was added and the mixture was purged with N$_2$, then placed under a balloon of H$_2$ and stirred at room temp for 18 h. The hydrogen was purged with N$_2$ and the mixture filtered through a pad of Celite®. The filtrate was evaporated to afford the desired material as a pale yellow solid (5 mg).

The cyclopentyl 3-(6-azido-9H-purin-9-yl)-N-(tert-butoxycarbonyl)-L-alaninate used in the above process was prepared as follows:

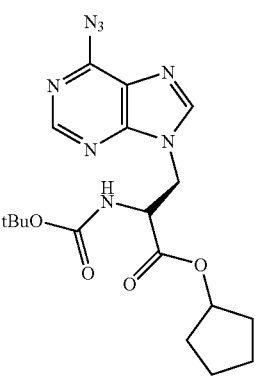

Cyclopentyl N-(tert-butoxycarbonyl)-3-(6-chloro-9H-purin-9-yl)-L-alaninate (25 mg, 0.06 mmol) and sodium azide (4.76 mg, 0.073 mmol) were dissolved in EtOH (0.5 mL) and heated at 75° C. for 48 h. The mixture was cooled, diluted with CH$_2$Cl$_2$ and filtered through Celite®. The filtrate was evaporated and the residue was used without purification.

The cyclopentyl N-(tert-butoxycarbonyl)-3-(6-chloro-9H-purin-9-yl)-L-alaninate used in the above process was prepared as follows:

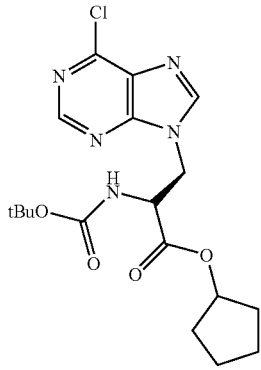

Cyclopentyl 3-[(5-amino-6-chloropyrimidin-4-yl)amino]-N-(tert-butoxycarbonyl)-L-alaninate (463 mg, 1.16 mmol) was treated with triethyl orthoformate (7 ml, 42.0 mmol) and p-toluenesulfonic acid monohydrate (22.02 mg, 0.12 mmol) was added to the resulting suspension, whereupon a colourless solution formed. The solution was stirred at room temp for 18 h. The mixture was partitioned between EtOAc (100 ml) and NaHCO$_3$ solution (100 ml) and the phases separated. The organic phase was washed with brine (100 ml), dried (MgSO$_4$) and evaporated to afford the desired material (534 mg) as a viscous, pale yellow oil. m/z 410 (M+H)$^+$.

The cyclopentyl 3-[(5-amino-6-chloropyrimidin-4-yl)amino]-N-(tert-butoxycarbonyl)-L-alaninate used in the above process was prepared as follows:

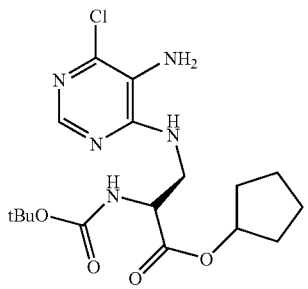

A mixture of 3-[(5-amino-6-chloropyrimidin-4-yl)amino]-N-(tert-butoxycarbonyl)-L-alanine (730 mg, 2.200 mmol), EDC (506 mg, 2.64 mmol) and DMAP (26.9 mg, 0.220 mmol) was dissolved in DCM (15 ml) and treated with cyclopentanol (408 µl, 4.40 mmol). The mixture was stirred at room temp for 36 h. The mixture was concentrated to ca. 5 ml and purified (silica gel, 10-20% MeCN/DCM), then triturated in Et$_2$O/isohexane to afford the desired material (558 mg) as a white solid. m/z 400 (M+H)$^+$ The 3-[(5-amino-6-chloropyrimidin-4-yl)amino]-N-(tert-butoxycarbonyl)-L-alanine used in the above process was prepared as follows:

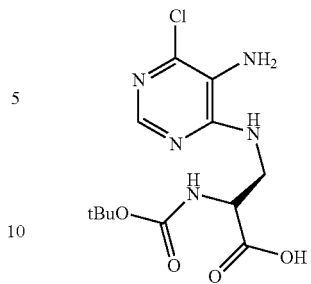

5-Amino-4,6-Dichloropyrimidine (500 mg, 3.05 mmol) and Boc-DAP-OH (934 mg, 4.57 mmol) were suspended in DMSO (10 ml) and treated with triethylamine (1500 µl, 10.67 mmol). The resulting mixture was heated at 90° C. for 3 days. (After ca. 20 min, a thick solid precipitated, hindering stirring. Additional DMSO (5 ml) was added and a solution eventually formed.) The reaction mixture was partitioned between EtOAc (200 ml) and water (200 ml) and the phases separated. The organic phase was extracted with water (2×100 ml) and the combined aqueous phases acidified (1M HCl) and extracted with EtOAc (3×200 ml). The combined extracts were washed with brine (4×300 ml), dried (MgSO$_4$) and evaporated to afford the desired product (755 mg, 2.276 mmol, 74.6% yield) as a pale yellow powder. m/z 332 (M+H)$^+$ Example 7

Cyclopentyl 4-{6-amino-8-[(1,3-benzodioxol-5-yl)thio]-9H-purin-9-yl}-L-phenylalaninate

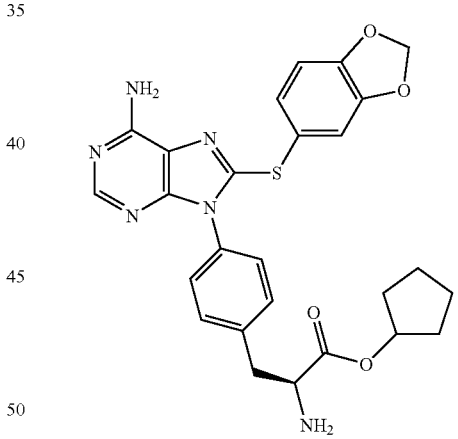

A solution of cyclopentyl 4-{6-amino-8-[(1,3-benzodioxol-5-yl)thio]-9H-purin-9-yl}-L-N-(tert-butoxycarbonyl)-phenylalaninate (50 mg, 0.081 mmol) in trifluoroacetic acid (250 µl, 3.24 mmol) and DCM (1 ml) was stirred at room temp for 2 h. The mixture was evaporated and purified on SCX (0.5 g) to afford the title compound (23 mg) as a white solid. m/z 519 (M+H)$^+$. $^1$H NMR (400 MHz, CHCl$_3$-d) d: 8.26 (1H, s), 7.30 (2H, d, J=7.8 Hz), 7.41 (2H, d, J=8.1 Hz), 6.91 (2H, d, J=2.0 Hz), 6.74 (1H, d, J=7.8 Hz), 5.98 (2H, s), 5.53 (2H, br. s), 5.22 (1H, m), 3.71 (1H, dd, J=7.8, 5.4 Hz), 3.13 (1H, dd, J=13.4, 5.6 Hz), 2.92 (1H, dd, J=13.7, 7.8 Hz), 1.87 (2H, m), 1.69-1.60 (10H, br m).

The cyclopentyl 4-{6-amino-8-[(1,3-benzodioxol-5-yl)thio]-9H-purin-9-yl}-L-N-(tert-butoxycarbonyl)-phenylalaninate used in the above process was prepared as follows:

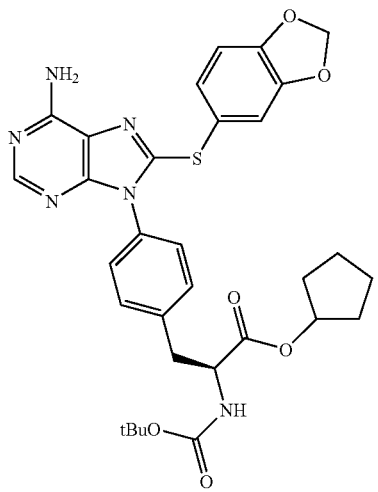

A mixture of cyclopentyl 3-(6-amino-8-bromo-9H-purin-9-yl)-N-(tertbutoxycarbonyl)-L-phenyl-alaninate (510 mg, 0.935-mmol), 3,4-methylenedioxythiophenol (577 mg, 3.74 mmol) and cesium carbonate (1523 mg, 4.68 mmol) was dissolved in DMF (15 ml) and heated at 50° C. for 3 h. The mixture was diluted with EtOAc (200 ml) and washed with water (2×100 ml) and brine (4×100 ml), dried (MgSO₄) and evaporated to give the crude product as a sticky tan solid. Purification (silica gel, 2.5% MeOH/DCM) afforded the desired material (456 mg) as a yellow solid. m/z 619 (M+H)⁺

The cyclopentyl 3-(6-amino-8-bromo-9H-purin-9-yl)-N-(tert-butoxycarbonyl)-L-phenylalaninate used in the above process was prepared as follows:

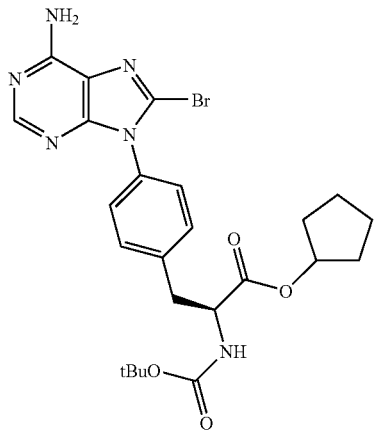

Cyclopentyl 3-(6-amino-9H-purin-9-yl)-N-(tert-butoxycarbonyl)-L-phenylalaninate (610 mg, 1.31 mmol) and N-bromosuccinimide (465 mg, 2.62 mmol) were dissolved in MeCN (25 ml) and the resulting solution heated at 60° C. for 18 h. The mixture was cooled, evaporated and purified by chromatography (silica gel, 2-5% MeOH/DCM) to afford the desired material (511 mg).

The cyclopentyl 3-(6-amino-9H-purin-9-yl)-N-(tert-butoxycarbonyl)-L-phenylalaninate used in the above process was prepared as follows

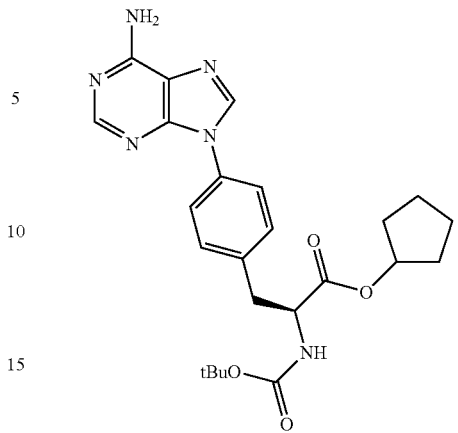

A mixture of adenine (1.5 g, 11.10 mmol), copper(II) acetate (2.02 g, 11.10 mmol), cyclopentyl N-(tert-butoxycarbonyl)-4-(4,4,5,5-tetramethyl-1,3,2-dioxaborolan-2-yl)-L-phenylalaninate (6.45 g, 11.1 mmol) and TMEDA (3.35 ml, 22.20 mmol) in MeOH (140 ml) and water (40 ml) was stirred vigorously under an atmosphere of air at room temp for 18 h. The mixture was evaporated and partitioned between EtOAc (200 ml) and water (100 ml) and the phases separated. The aqueous phase was extracted with EtOAc (2×200 ml) and the combined organic phases washed with water (400 ml) and brine (400 ml), dried (MgSO₄) and evaporated. Column chromatography (silica gel, 2.5% MeOH/DCM) afforded a thick cloudy oil (1.5 g). Trituration with 50% Et₂O/isohexane to remove pinacol residues afforded the desired material (614 mg, 1.263 mmol, 11.38% yield) as a white solid.

The cyclopentyl N-(tert-butoxycarbonyl)-4-(4,4,5,5-tetramethyl-1,3,2-dioxaborolan-2-yl)-L-phenylalaninate used in the above process was prepared as follows:

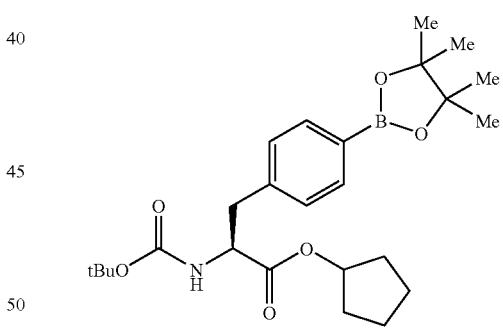

Cyclopentyl N-(tert-butoxycarbonyl)-4-iodo-L-phenylalaninate (5.1 g, 11.10 mmol), bis-pinacolatodiboron (4.23 g, 16.66 mmol), PdCl₂(dppf) (0.453 g, 0.555 mmol) and potassium acetate (1.635 g, 16.66 mmol) were combined in a vessel and purged with N₂. DMSO (20 ml) was added and the mixture heated at 50° C. for 48 h. The mixture was partitioned between Et₂O (200 ml) and water (400 ml) and the phases separated. The aqueous phase was extracted with Et₂O (2×200 ml) and the combined organic phases washed with brine (3×300 ml), dried (MgSO₄) and evaporated to give the crude product as a dark brown oil. Purification (silica gel, 10% EtOAc/isohexane) afforded the desired material (6.44 g, 11.07 mmol).

The cyclopentyl N-(tert-butoxycarbonyl)-4-iodo-L-phenylalaninate used in the above process

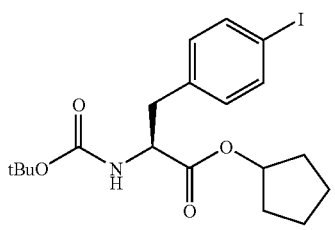

A mixture of cyclopentyl N-(tert-butoxycarbonyl)-4-iodo-L-phenylalanine (10 g, 25.6 mmol), EDC (5.88 g, 30.7 mmol) and DMAP (0.312 g, 2.56 mmol) was dissolved in DCM (150 ml) and treated with cyclopentanol (2.84 ml, 30.7 mmol). The mixture was stirred at room temp for 18 h. The mixture was pre-absorbed onto $SiO_2$ (20 g) and the residue purified by chromatography (silica gel, 7.5% EtOAc/isohexane) to afford desired material (10.32 g) as a clear colourless oil. m/z 460 $(M+H)^+$ Example 8

Cyclopentyl 4-{6-amino-8-[(6-bromo-1,3-benzodioxol-5-yl)thio]-9H-purin-9-yl}-L-phenylalaninate

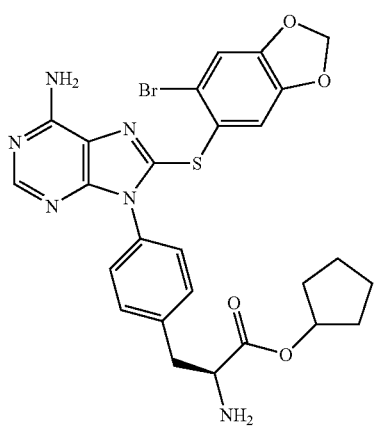

A solution of cyclopentyl 4-{6-amino-8-[(6-bromo-1,3-benzodioxol-5-yl)thio]-9H-purin-9-yl}-N-(tert-butoxycarbonyl)-L-phenylalaninate (44 mg, 0.063 mmol) in TFA (250 µl, 3.24 mmol) and DCM (1 ml) was stirred at room temp for 2 h. Chromatography (silica gel, 2-5% MeOH/DCM) afforded the title compound (20 mg) as a pale yellow solid. m/z 597 $(M+H)^+$. $^1H$ NMR (400 MHz, $CHCl_3$-d) d: 8.28 (1H, s), 7.32-7.40 (4H, m), 7.03 (1H, s), 6.93 (1H, s), 6.00 (1H, s), 5.53 (2H, s), 5.20 (1H, m), 3.71 (1H, dd, J=7.8, 5.4 Hz), 3.13 (1H, dd, J=13.7, 5.4 Hz), 2.90 (1H, dd, J=13.7, 7.8 Hz), 1.86 (2H, m), 1.75-1.55 (10H, br m).

The cyclopentyl 4-{6-amino-8-[(6-bromo-1,3-benzodioxol-5-yl)thio]-9H-purin-9-yl}-N-(tert-butoxycarbonyl)-L-phenylalaninate used in the above process was prepared as follows:

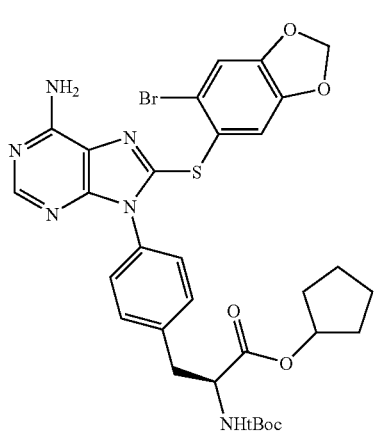

A mixture of cyclopentyl 4-{6-amino-8-[(1,3-benzodioxol-5-yl)thio]-9H-purin-9-yl}-L-N-(tert-butoxycarbonyl)-phenylalaninate [described in Example 7] (180 mg, 0.291 mmol) and N-bromosuccinimide (104 mg, 0.582 mmol) was dissolved in MeCN (10 ml) and stirred at room temp for 18 h. The mixture was evaporated and partially purified (silica gel, 2% MeOH/DCM) afforded the desired material (44 mg) as a yellow solid. m/z 699 $(M+H)^+$ Example 9

(S)-2-amino-5-(6-amino-8-(6-iodobenzo[d][1,3]dioxol-5-ylthio)-9H-purin-9-yl)pentanoic acid

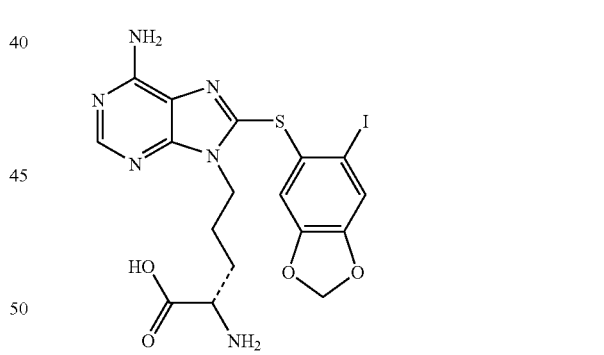

Lithium hydroxide (2.88 mg, 0.12 mmol) was added to a solution of (S)-cyclopentyl 2-amino-5-(6-amino-8-(6-iodobenzo[d][1,3]dioxol-5-ylthio)-9H-purin-9-yl)pentanoate (14.0 mg, 0.02 mmol) in tetrahydrofuran (1 ml) and water (3 drops). After stirring for 12 h, 5 drops of acetic acid and water (0.1 ml) were added to the reaction mixture. The solid was collected by filtration and dried in vacuo to afford the title compound (3.6 mg) as a white solid. m/z 529 $[M+H]^+$, 527 $[M-H]^-$. $^1H$ NMR (400 MHz, DMSO-d6), δ: 8.1 (1H, s), 7.4 (1H, s), 7.3 (2H, bs), 6.8 (1H, s), 6.0 (2H, s), 4.1 (2H, m), 3.1 (1H, m), 1.8-1.4 (5H, m).

Example 10

(S)-2-amino-4-(6-amino-8-(6-iodobenzo[d][1,3]di-oxol-5-ylthio)-9H-purin-9-yl)butanoic acid

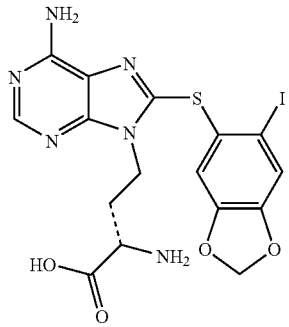

Lithium hydroxide (2.41 mg, 0.10 mmol) was added to a solution of (S)-cyclopentyl 2-amino-4-(6-amino-8-(6-iodo-benzo[d][1,3]dioxol-5-ylthio)-9H-purin-9-yl)butanoate (12.0 mg, 0.02 mmol) in tetrahydrofuran (1 ml) and water (3 drops). After stirring for 12 h, 5 drops of acetic acid and water (0.1 ml) were added to the reaction mixture. The solid was collected by filtration and dried in vacuo to afford the product as a white solid (1.5 mg, 12%). m/z 515 [M+H]$^+$, 513 [M−H]$^-$. $^1$H NMR (400 MHz, d-MeOH), δ: 8.1 (1H, s), 7.4 (1H, s), 7.2 (1H, s), 6.1 (2H, s), 4.4 (2H, m), 3.5 (1H, m), 2.5 (1H, m), 2.2 (1H, m).

The examples in Table 1 were prepared in a similar manner to the compound of Example 9.

TABLE 1

| Example | Starting Material | R1 | R2 | Name | m/z |
|---------|-------------------|----|----|------|-----|
| 11 | Example 4 | (R)-CH(NH₂)(CO₂H)CH₂CH₂— | I | (R)-2-amino-4-(6-amino-8-(6-iodo benzo[d][1,3] dioxol-5-ylthio)-9H-purin-9-yl) butanoic acid | 515 [M + H]$^+$ |
| 12 | Example 3 | (R)-CH(NH₂)(CO₂H)CH₂CH₂CH₂— | I | (R)-2-amino-5-(6-amino-8-[(6-iodo-1,3-benzodioxol-5-ylthio)]-9H-purin-9-yl)pentanoic acid | 529 [M + H]$^+$ |
| 13 | Example 7 | 4-methylbenzyl-CH(NH₂)(CO₂H)— | H | 4-{6-amino-8-[(1,3-benzodioxol-5-yl)thio]-9H-purin-9-yl}-L-phenylalanine | 451 [M + H]$^+$ |
| 14 | Example 8 | 4-methylbenzyl-CH(NH₂)(CO₂H)— | Br | 4-{6-amino-8-[(6-bromo-1,3-benzo dioxol-5-yl)thio]-9H-purin-9-yl}-L-phenyl alanine | 530 [M + H]$^+$ |

Example 15

Biological Data

Hsp90 Assay

An HTRF (homogeneous time resolved fluorescence assay) assay was used to measure the interaction of the compounds with HSP90.

The assay measures binding of biotinylated GM (bio-GM; Biomol, #EI-341, lot: A9199a) to human recombinant his-tagged HSP90α (HSP90; Prospec Technogene, #HSP90, lot: 260HSP9001). A signal is generated by fluorescence resonance energy transfer from an Europium-cryptate labeled anti-his antibody (anti-6HIS-Cryptate; Cisbio International, #61HISKLA, lot: 33V) via the HSP90-GM-biotin complex to a fluorescence acceptor (allophycocyanin) linked to streptavidin (SA-XL; Cisbio International, #610SAXLB, lot: 089).

Unlabeled GM or compounds compete with the bio-GM for binding to HSP90 resulting in reduced fluorescence energy transfer/assay signal.

For the assay a preformed (1 h incubation) complex of HSP90 with the anti-his-K is added to the compound solution in a 384 well microplate (Corning, #3710) and incubated for 15 min. A preformed (1 h incubation) complex of bio-GM with the SA-XL was added to the wells and incubated for 20 h. All incubations were performed at room temperature. The final assay volume was 50 µl/well. The final concentrations in the assay were: 50 mM Hepes pH 7.3, 50 mM NaCl, 100 mM KF, 1 mM EDTA, 1 mM DTT, 0.1% Triton-X-100, 1 nM anti-his-K, 40 nM HSP90, 40 nM SA-XL, 40 nM bio-GM. Test compounds were dissolved in DMSO, prediluted in assay buffer and tested at a final concentration between 5000 nM and 0.3 nM. The resulting DMSO concentration was 0.5% and included in all controls. High controls were without test compounds, low controls without test compounds, without HSP90 and without bio-GM. As a reference inhibitor unlabeled GM was used in the same concentrations as the test compounds.

Inhibition was calculated compared to the assay controls using an Excel spreadsheet (Microsoft). $IC_{50}$ values were calculated by non-linear least squares fitting to the standard dose-response model using GraphPad Prism (GraphPad Software Inc).

Cell Inhibition Assay

Cells were seeded in 96W tissue culture plates (1 well=30 mm$^2$) at a density of 500 cells per well in 50 µl of the appropriate culture medium (see below). 24 hrs later 50 µl of the compound prepared in the same medium was added as 4 fold dilutions to give final concentrations in the range 0.15 nM-2500 nM (n=6 for each concentration). The plates were then incubated at 37° C., 5% $CO_2$ for 120 hrs. Cell proliferation was assessed using WST-1 (a metabolic indicator dye, Roche Cat no. 1 644 807) according to the manufacturers instructions. The results were calculated as percentage of vehicle response and IC50 values represent the concentration of compound that inhibited the vehicle response by 50%. HCT-116 Culture Medium—Dulbeccos MEM (Sigma D6546) plus 10% heat inactivated fetal calf serum (Hyclone SH30071 Thermo Fischer Scientific) containing 2 mM Glutamine (Sigma cat no G-7513) and 50 U/ml Penicillin and Streptomycin Sulphate (Sigma Cat no P-0781).

Data were expressed as a percentage inhibition of the control, measured in the absence of inhibitor, as follows:

$$\% \text{ inhibition} = 100 - ((S^i/S^o) \times 100)$$

where $S^i$ is the signal in the presence of inhibitor and S0 is the signal in the presence of DMSO.

IC50 values were determined by non-linear regression analysis, after fitting the results of eight data points to the equation for sigmoidal dose response with variable slope (% activity against log concentration of compound), using Graphpad Prism® software.

IC50 results were allocated to one of 3 ranges as follows:
Range A: IC50<1000 nM,
Range B: IC50 from 1000 nM to 10000 nM;
and Range C: IC50>10000 nM.
NT=Not tested

| Example Number | Inhibitor Activity vs Hsp90 | Inhibitor Activity vs HCT 116 cell line |
|---|---|---|
| 1 | A | A |
| 2 | A | A |
| 3 | A | A |
| 4 | A | A |
| 5 | A | B |
| 6 | A | NT |
| 7 | B | NT |
| 8 | B | NT |
| 9 | A | NT |
| 10 | A | NT |
| 13 | B | NT |
| 14 | A | NT |

The invention claimed is:

1. A compound which is (a) an amino acid derivative having formula (I) or a tautomer thereof, or (b) a pharmaceutically acceptable salt, N-oxide or solvate thereof:

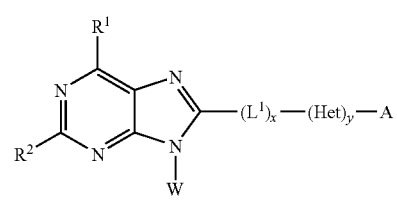

(I)

wherein:
R$^1$ represents a hydrogen or halogen atom, or a cyano, nitro, —N$_3$, C$_{1-6}$ alkyl, C$_{2-6}$ alkenyl, C$_{2-6}$ alkynyl, C$_{1-6}$ alkoxy, C$_{2-6}$ alkenyloxy, hydroxyl, mercapto, C$_{1-6}$ alkylthio, C$_{2-6}$ alkenylthio, guanidine, amidine, —NR'R", —NR'''OR' or —NR'''R'R" group wherein each R', R" and R''' group is the same or different and represents hydrogen or C$_{1-4}$ alkyl, or represents a group of formula —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —OCONH$_2$, —OCONHR$^A$, —OCONR$^A$R$^B$, —NHCOR$^A$, NHCOOR$^A$, —NR$^B$COOR$^A$, —NHSO$_2$R$^A$, —NR$^B$SO$_2$R$^A$, —NHSO$_2$OR$^A$, —NR$^B$SO$_2$OH, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$ or —NR$^A$CONR$^A$R$^B$ wherein R$^A$ and R$^B$ are the same or different and represent C$_{1-6}$ alkyl, C$_{3-6}$ cycloalkyl, non-fused phenyl or a non-fused 5- to 6-membered heteroaryl, or R$^A$ and R$^B$ when attached to the same nitrogen atom form a non-fused 5- or 6-membered heterocyclyl group;

R$^2$ represents a hydrogen or halogen atom, or a cyano, nitro, —N$_3$, C$_{1-6}$ alkyl, C$_{1-6}$ alkenyl, C$_{2-6}$ alkynyl group, or a group of formula —NR'R", —CO$_2$R', —SO$_2$R', —NR'OR" or —CONR'R" wherein R' and R" are the same or different and represent hydrogen or unsubstituted C$_{1-4}$ alkyl, or a C$_{6-10}$ aryl, 5- to 10-membered heteroaryl, C$_{3-7}$ carbocyclyl or 5- to 10-membered heterocyclyl group;

x and y are the same or different and represent zero or 1;
L$^1$ represents C$_{1-4}$ alkylene;

Het represents —S—, —S(O)—, —S(O)$_2$—, —NR'— or —O— wherein R' represents hydrogen or unsubstituted C$_{1-4}$ alkyl;

A represents a C$_{6-10}$ aryl, 5- to 10-membered heteroaryl, C$_{3-7}$ carbocyclyl or 5- to 10-membered heterocyclyl group which is optionally fused to a further C$_{6-10}$ aryl, 5- to 10-membered heteroaryl, C$_{3-7}$ carbocyclyl or 5- to 10-membered heterocyclyl group;

W is a group of formula —[CH$_2$]$_z$—Y$^1$-L$^2$-R, wherein:
z is 0 or 1;
Y$^1$ represents a bond or a group of formula —S—, —O—, —(C=O)—, —(S=O)—, —S(O$_2$)—, —NR$^3$—, —(C=O)NR$^3$—, —NR$^3$(C=O)—, —S(O$_2$)NR$^3$—, —NR$^3$S(O$_2$)—, —NR$^3$(C=O)NR$^4$— or —NR$^3$(C=S)NR$^4$—, wherein R$^3$ and R$^4$ are the same or different and represent hydrogen or C$_{1-6}$ alkyl;
L$^2$ is a divalent radical of formula -(Alk$^1$)$_m$(Q)$_n$(Alk$^2$)$_p$— wherein:
m, n and p are independently 0 or 1;
Q either (i) represents a phenyl, 5- to 10-membered heteroaryl, C$_{3-7}$ carbocyclyl or 5- to 10-membered heterocyclyl group optionally fused to a further phenyl, 5- to 10-membered heteroaryl, C$_{3-7}$ carbocyclyl or 5- to 10-membered heterocyclyl group; or (ii) in the case wherein p is 0, represents a group of formula -Q$^1$-X$^1$- wherein X$^1$ represents —O—, —S— or —NR$^S$— wherein R$^5$ is hydrogen or C$_{1-4}$ alkyl, and Q$^1$ represents a phenyl, 5- to 10-membered heteroaryl, C$_{3-7}$ carbocyclyl or 5- to 10-membered heterocyclyl group optionally fused to a further phenyl, 5- to 10-membered heteroaryl, C$_{3-7}$ carbocyclyl or 5- to 10-membered heterocyclyl group;
Alk$^1$ and Alk$^2$ are the same or different and represent C$_{3-7}$ carbocyclyl groups, or represent C$_{1-6}$ alkylene, C$_{2-6}$ alkenylene, or C$_{2-6}$ alkynylene groups which may optionally contain or terminate in an ether (—O—), thioether (—S—) or amino (—NR$^6$—) link wherein R$^6$ represents hydrogen or C$_{1-4}$ alkyl;
R is a radical of formula (X) or (Y):

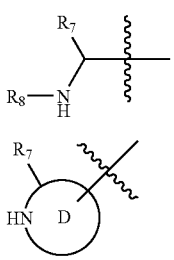

(X)

(Y)

wherein:
R$^7$ is a group —COOH or an ester thereof which is hydrolysable by one or more intracellular carboxylesterase enzymes to a —COOH group;
R$^8$ represents hydrogen or a C$_{1-6}$ alkyl, —(C=O)R$^9$, —(C=O)OR$^{10}$ or —(C=O)NR$^{10}$ group wherein R$^9$ represents hydrogen, a C$_{1-6}$ alkyl group, a phenyl, 5- to 10-membered heteroaryl, C$_{3-7}$ carbocyclyl or 5- to 10-membered heterocyclyl group optionally fused to a further phenyl, 5- to 10-membered heteroaryl, C$_{3-7}$ carbocyclyl or 5- to 10-membered heterocyclyl group, or R$^9$ represents a group of formula -Alk$^4$-Cyc wherein Alk$^4$ represents a C$_{1-6}$ alkylene group and Cyc represents a phenyl, 5- to 10-membered heteroaryl or 5- to 10-membered heterocyclyl group optionally fused to a further phenyl, 5- to 10-membered heteroaryl, C$_{3-7}$ carbocyclyl or 5- to 10-membered heterocyclyl group, and R$^{10}$ represents hydrogen or C$_{1-6}$ alkyl, or wherein R$^8$ represents a phenyl, 5- to 10-membered heteroaryl, C$_{3-7}$ carbocyclyl or 5- to 10-membered heterocyclyl group optionally fused to a further phenyl, 5- to 10-membered heteroaryl, C$_{3-7}$ carbocyclyl or 5- to 10-membered heterocyclyl group; and D represents a 5- or 6-membered heteroaryl or 5- or 6-membered heterocyclyl group wherein R$^7$ is linked to a ring carbon adjacent the ring nitrogen shown, and wherein ring D is optionally fused to a phenyl, 5- to 10-membered heteroaryl, C$_{3-7}$ carbocyclyl or 5- to 10-membered heterocyclyl group in which case the bond shown intersected by a wavy line may be from a ring atom in said second ring;

wherein
the alkyl, alkylene, alkenyl and alkynyl moieties in R$^1$, R$^2$, R$^3$, R$^4$, R$^5$, R$^6$, R$^8$, R$^9$, R$^{10}$, Alk$^1$, Alk$^2$ and Alk$^3$ are unsubstituted or substituted by 1, 2 or 3 substituents which are the same or different and are selected from halogen atoms and C$_{1-4}$ alkyl, C$_{2-4}$ alkenyl, C$_{1-4}$ alkoxy, C$_{2-4}$ alkenyloxy, C$_{1-4}$ haloalkyl, C$_{2-4}$ haloalkenyl, C$_{1-4}$ haloalkoxy, C$_{2-4}$ haloalkenyloxy, hydroxyl, mercapto, cyano, nitro, C$_{1-4}$ hydroxyalkyl, C$_{2-4}$ hydroxyalkenyl, C$_{1-4}$ alkylthio, C$_{2-4}$ alkenylthio, phenyl, —NR'R" groups wherein each R' and R" is the same or different and represents hydrogen or C$_{1-4}$ alkyl, and groups of formula —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —OCONH$_2$, —OCONHR$^A$, —OCONR$^A$R$^B$, —NHCOR$^A$, NHCOOR$^A$, —NR$^B$COOR$^A$, —NHSO$_2$OR$^A$, —NR$^B$SO$_2$OH, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$ or —NR$^A$CONR$^A$R$^B$ wherein R$^A$ and R$^B$ are the same or different and represent C$_{1-6}$ alkyl, C$_{3-6}$ cycloalkyl, phenyl or a non-fused 5- to 6-membered heteroaryl, or R$^A$ and R$^B$ when attached to the same nitrogen atom form a non-fused 5- or 6-membered heterocyclyl group; and
the phenyl, heteroaryl, heterocyclyl and carbocyclyl moieties in R$^1$, R$^2$, R$^8$, R$^9$, A, Q, Q$^1$ and D are unsubstituted or substituted by 1, 2, 3 or 4 substituents which are the same or different and are selected from halogen atoms and C$_{1-4}$ alkyl, C$_{1-4}$ alkylene, C$_{2-4}$ alkenyl, C$_{1-4}$ alkoxy, C$_{2-4}$ alkenyloxy, C$_{1-4}$ haloalkyl, C$_{2-4}$ haloalkenyl, C$_{1-4}$ haloalkoxy, C$_{2-4}$ haloalkenyloxy, hydroxyl, mercapto, cyano, nitro, C$_{1-4}$ hydroxyalkyl, C$_{2-4}$ hydroxyalkenyl, C$_{1-4}$ alkylthio, C$_{2-4}$ alkenylthio, —NR'R" groups wherein each R' and R" is the same or different and represents hydrogen or C$_{1-4}$ alkyl, and groups of formula —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —OCONH$_2$, —OCONHR$^A$, —OCONR$^A$R$^B$, —NHCOR$^A$, NHCOOR$^A$, —NR$^B$COOR$^A$, —NHSO$_2$OR$^A$, —NR$^B$SO$_2$OH, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$ or —NR$^A$CONR$^A$R$^B$ wherein R$^A$ and R$^B$ are the same or different and represent C$_{1-6}$ alkyl, C$_{3-6}$ cycloalkyl, phenyl or a non-fused 5- to 6-membered heteroaryl, or R$^A$ and R$^B$ when attached to the same nitrogen atom form a non-fused 5- or 6-membered heterocyclyl group.

2. A compound as claimed in claim 1, wherein:
(i) R$^1$ represents hydrogen or halogen atom, or an unsubstituted C$_{1-4}$ alkyl, hydroxyl, C$_{1-4}$ alkoxy, mercapto, C$_{1-4}$ alkylthio, —NR'R" or —CONR$^A$R$^B$ group wherein R', R", R$^A$ and R$^B$ are the same or different and represent hydrogen or unsubstituted C$_{1-4}$ alkyl group, and wherein the alkyl groups or moieties in R$^1$ are unsubstituted or substituted by 1, 2 or 3 substituents which are themselves unsubstituted and are selected from halogen, $C_{1-4}$ alkyl, $C_{2-4}$ alkenyl, $C_{1-4}$ alkoxy, hydroxyl, $C_{1-4}$ haloalkyl, $C_{2-4}$ haloalkenyl, $C_{1-4}$ haloalkyloxy, $C_{2-4}$ haloalkenyloxy and —NR'R" wherein R' and R" are the same or different and represent hydrogen or $C_{1-2}$ alkyl;

(ii) $R^2$ represents a hydrogen or halogen atom, an unsubstituted $C_{1-4}$ alkyl group or a group of formula —NR'R" wherein R' and R" are the same or different and represent hydrogen or unsubstituted $C_{1-2}$ alkyl;

(iii) x is zero and y is one;

(iv) Het represents —S—, —S(O)— or —S(O)$_2$—;

(v) A represents an unsubstituted or substituted group selected from non-fused phenyl, non-fused 5- to 6-membered heteroaryl, non-fused $C_{3-7}$ carbocyclyl, non-fused 5- to 6-membered heterocyclyl group, a phenyl group which is fused to a further 5- to 6-membered heterocyclyl group, or a 5- to 6-membered heteroaryl group which is fused to a further phenyl group, and wherein the phenyl, heteroaryl, carbocyclyl and heterocyclyl groups and moieties are unsubstituted or substituted by 1, 2, 3 or 4 substituents which are the same or different and are selected from halogen atoms and $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, mercapto, cyano, nitro, $C_{1-4}$ hydroxyalkyl, $C_{2-4}$ hydroxyalkenyl, $C_{1-4}$ alkylthio, $C_{2-4}$ alkenylthio and —NR'R" groups wherein each R' and R" is the same or different and represents hydrogen or $C_{1-4}$ alkyl, and groups of formula $COR^A$, —$SO_2R^A$, —$CONH_2$, —$SO_2NH_2$, —$CONHR^A$, —$SO_2NHR^A$, —$CONR^AR^B$ and —$SO_2NR^AR^B$ wherein $R^A$ and $R^B$ are the same or different and represent $C_{1-4}$ alkyl;

(vi) z is zero;

(vii) $Y^1$ is a bond or represents a group of formula —O—, —S—, —O—(C=O)—, —(C=O)—O—, —(C=O)—, —(S=O)—, —S(O$_2$)—, —$NR^3$—, —(C=O)$NR^3$—, —$NR^3$(C=O)—, —S(O$_2$)$NR^3$— and —$NR^3$S(O$_2$)—, wherein $R^3$ represents hydrogen or $C_{1-6}$ alkyl;

(viii) m, n and p are the same or different and represent zero or 1;

Alk$^1$ represents a $C_{1-4}$ alkylene group which is unsubstituted or substituted by 1 or 2 substituents which are the same or different and are selected from halogen, $C_{1-2}$ alkoxy, hydroxyl and —NR'R" wherein R' and R" are the same or different and represent hydrogen or $C_{1-2}$ alkyl;

Q represents phenyl optionally fused to a further phenyl, a 5- to 10-membered heteroaryl optionally fused to a further phenyl, a non-fused $C_{3-7}$ carbocyclyl or a non-fused 5- to 10-membered heterocyclyl group, and wherein the phenyl, heteroaryl, carbocyclyl and heterocyclyl groups of Q are unsubstituted or substituted by 1 or 2 substituents which are the same or different and are selected from halogen atoms and $C_{1-4}$ alkyl, $C_{1-4}$ alkoxy and hydroxyl groups; and Alk$^2$ represents a $C_{1-4}$ alkylene group which is unsubstituted or substituted by 1 or 2 substituents which are the same or different and are selected from halogen, $C_{1-2}$ alkoxy, hydroxyl and —NR'R" wherein R' and R" are the same or different and represent hydrogen or $C_{1-2}$ alkyl; or (ix) R represents a group of formula (X);

$R^7$ represents —COOH or is an ester group —COOR$^{11}$ wherein the ester group is hydrolysable by one or more intracellular carboxylesterase enzymes to a carboxylic acid group; and $R^8$ represents hydrogen or a $C_{1-6}$ alkyl, —(C=O)$R^9$ or —(C=O)OR$^{10}$ wherein $R^9$ and $R^{10}$ are as defined in claim 1.

3. A compound as claimed in claim 1 which is (a) an amino acid derivative having formula (IA) or a tautomer thereof, or (b) a pharmaceutically acceptable salt, N-oxide or solvate thereof:

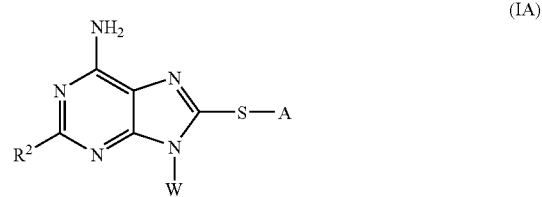

(IA)

wherein:

$R^2$ represents a hydrogen or halogen atom, an unsubstituted $C_{1-4}$ alkyl group or a group of formula —NR'R" wherein R' and R" are the same or different and represent hydrogen or unsubstituted $C_{1-2}$ alkyl;

A represents an unsubstituted or substituted group selected from non-fused phenyl, non-fused 5- to 6-membered heteroaryl, non-fused $C_{3-7}$ carbocyclyl, non-fused 5- to 6-membered heterocyclyl group, a phenyl group which is fused to a further 5- to 6-membered heterocyclyl group, or a 5- to 6-membered heteroaryl group which is fused to a further phenyl group, and wherein the phenyl, heteroaryl, carbocyclyl and heterocyclyl groups and moieties are unsubstituted or substituted by 1, 2, 3 or 4 substituents which are the same or different and are selected from halogen atoms and $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, mercapto, cyano, nitro, $C_{1-4}$ hydroxyalkyl, $C_{2-4}$ hydroxyalkenyl, $C_{1-4}$ alkylthio, $C_{2-4}$ alkenylthio and —NR'R" groups wherein each R' and R" is the same or different and represents hydrogen or $C_{1-4}$ alkyl, and groups of formula $COR^A$, —$SO_2R^A$, —$CONH_2$, —$SO_2NH_2$, —$CONHR^A$, —$SO_2NHR^A$, —$CONR^AR^B$ and —$SO_2NR^AR^B$ wherein $R^A$ and $R^a$ are the same or different and represent $C_{1-4}$ alkyl; and W is a group of formula —$Y^1$-$L^2$-R, and R is a group of formula (X);

$Y^1$ is a bond or represents a group of formula —O—, —S—, —O—(C=O)—, —(C=O)—O—, —(C=O)—, —(S=O)—, —S(O$_2$)—, —$NR^3$—, —(C=O)$NR^3$—, —$NR^3$(C=O)—, —S(O$_2$)$NR^3$— and —$NR^3$S(O$_2$)—, wherein $R^3$ represents hydrogen or $C_{1-6}$ alkyl;

either (i) m is 1, n and p are zero, and $L^2$ represents a group -Alk$^1$- wherein Alk$^1$ represents a $C_{1-4}$ alkylene group which is unsubstituted or substituted by 1 or 2 substituents which are the same or different and are selected from halogen, $C_{1-2}$ alkoxy, hydroxyl and —NR'R" wherein R' and R" are the same or different and represent hydrogen or $C_{1-2}$ alkyl; or (ii) m is zero, n and p are 1, $L^2$ represents non-fused phenyl or a non-fused 5- to 10-membered heteroaryl group and Alk$^2$ represents a $C_{1-4}$ alkylene group;

$R^7$ represents —COOH or is an ester group —COOR$^{11}$ wherein the ester group is hydrolysable by one or more intracellular carboxylesterase enzymes to a carboxylic acid group; and $R^8$ represents hydrogen or a $C_{1-6}$ alkyl, —(C=O)$R^9$ or —(C=O)OR$^{10}$ wherein $R^9$ is $C_{1-6}$ alkyl, non-fused phenyl, non-fused 5- to 6-membered heteroaryl, non-fused $C_{3-7}$ carbocyclyl or a group -Alk$^4$-Cyc, and $R^{10}$ is hydrogen or $C_{1-4}$ alkyl.

4. A compound as claimed in claim 3, wherein:
(i) $R^2$ represents a hydrogen or halogen atom or an —$NH_2$ group;
(ii) A represents a group selected from phenyl, pyrrolyl, furanyl, thienyl, pyridinyl, pyridazinyl, pyrimidinyl, pyrazinyl, triazinyl, benzimidazolyl, benzoxazolyl, benzothiazolyl, tetrahydrofuranyl, pyrrolidinyl, tetrahydrothienyl, piperidinyl, tetrahydropyranyl, tetrahydrothiopyranyl, morpholinyl, thiomorpholinyl, pyrrolyl-2,5-dione and benzoquinone, or A represents a phenyl ring fused to a 5- to 6-membered heterocyclyl group selected from oxazolidinyl, imidazolidinyl, thiazolidinyl, thioxolanyl, dioxolanyl and dithiolanyl, and wherein A is unsubstituted or substituted by 1, 2, 3 or 4 substituents which are the same or different and represent halogen atoms or $C_{1-4}$ alkyl, $C_{1-2}$ alkoxy, $C_{1-2}$ alkylthio or hydroxy groups; or
(iii) $Y^1$ is a bond or represents a group of formula —O—, —S—, —$NR^3$—, —C(=O)—O—, —O—(C=O)—, —(C=O)$NR^3$— or —$NR^3$(C=O)— wherein $R^3$ is hydrogen or $C_{1-6}$ alkyl.

5. A compound as claimed in claim 4 wherein $R^2$ represents a hydrogen atom.

6. A compound as claimed in claim 4 wherein A represents a non-fused phenyl ring or a phenyl ring fused to a dioxolanyl ring, and wherein A is unsubstituted or substituted by 1, 2, 3 or 4 substituents which are the same or different and represent halogen atoms or $C_{1-4}$ alkyl, $C_{1-2}$ alkoxy, $C_{1-2}$ alkylthio or hydroxy groups.

7. A compound as claimed in claim 3, wherein $R^7$ represents a group —COOH or —$COOR^{11}$, wherein $R^{11}$ represents —$CR^{12}R^{13}R^{14}$ and:
(i) $R^{13}$ represents hydrogen or a group of formula —$[C_{1-4}$ alkylene$]_b$-$(Z^1)_a$-$[C_{1-4}$ alkyl] or —$[C_{1-4}$ alkylene$]_b$-$(Z^1)_a$-$[C_{2-4}$ alkenyl] wherein a and b are the same or different and represent 0 or 1, and $Z^1$ represents —O—, —S—, or —$NR^{17}$— wherein $R^{17}$ is hydrogen or $C_{1-4}$ alkyl, $R^{14}$ represents hydrogen or $C_{1-4}$ alkyl, and $R^{12}$ represents hydrogen or $C_{1-4}$ alkyl;
(ii) $R^{13}$ represents a phenyl or a 5- to 10-membered heteroaryl group optionally fused to a further phenyl, 5- to 10-membered heteroaryl, $C_{3-7}$ carbocyclyl or 5- to 10-membered heterocyclyl group, $R^{14}$ represents hydrogen or $C_{1-4}$ alkyl, and $R^{12}$ represents hydrogen;
(iii) $R^{13}$ represents a group of formula -$(Alk^3)$—$NR^{15}R^{16}$ wherein $Alk^3$ represents a $C_{1-4}$ alkylene group and either (a) $R^{15}$ and $R^{16}$ are the same or different and represent hydrogen or $C_{1-4}$ alkyl, or (b) $R^{15}$ and $R^{16}$, together with the nitrogen atom to which they are bonded, form a 5- to 10-membered heteroaryl or 5- to 10-membered heterocyclyl group optionally fused to a further phenyl, 5- to 10-membered heteroaryl, $C_{3-7}$ carbocyclyl or 5- to 10-membered heterocyclyl group; $R^{14}$ represents hydrogen or $C_{1-4}$ alkyl, and $R^{12}$ represents hydrogen; or
(iv) $R^{13}$ and $R^{14}$, together with the carbon atom to which they are bonded, form a phenyl, 5- to 10-membered heteroaryl, $C_{3-7}$ carbocyclyl or 5- to 10-membered heterocyclyl group which is optionally fused to a further phenyl, 5- to 10-membered heteroaryl, $C_{3-7}$ carbocyclyl or 5- to 10-membered heterocyclyl group, and $R^{12}$ represents hydrogen.

8. A compound as claimed in claim 7 wherein $R^{11}$ represents —$CR^{12}R^{13}R^{14}$, and either:
(i) $R^{12}$ represents hydrogen or $C_{1-2}$ alkyl; $R^{13}$ represents hydrogen, $C_{1-4}$ alkyl, $C_{2-4}$ alkenyl or a group —($C_{1-4}$ alkyl)-O—($C_{1-4}$ alkyl); and $R^{14}$ represents hydrogen or $C_{1-2}$ alkyl; or
(ii) $R^{12}$ represents hydrogen or $C_{1-2}$ alkyl, and $R^{13}$ and $R^{14}$ form a cyclic group together with the carbon atom to which they are bonded, form a non-fused $C_{3-7}$ carbocyclyl groups which is unsubstituted or substituted by one or two substituents which are the same or different and are selected from halogen atoms and $C_{1-4}$ alkyl, $C_{1-4}$ alkylene, $C_{1-4}$ alkoxy, $C_{1-4}$ haloalkyl, hydroxyl, cyano, nitro and —NR'R'' groups wherein each R' and R'' is the same or different and represents hydrogen or $C_{1-4}$ alkyl.

9. A compound as claimed in claim 1 which is (a) an amino acid derivative having formula (IB) or a tautomer thereof, or (b) a pharmaceutically acceptable salt, N-oxide or solvate thereof:

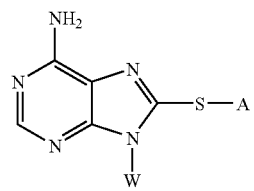

(IB)

wherein:
A represents a non-fused phenyl ring or a phenyl ring fused to a dioxolanyl ring, and wherein A is unsubstituted or substituted by 1, 2, 3 or 4 substituents which are the same or different and represent halogen atoms or $C_{1-4}$ alkyl, $C_{1-2}$ alkoxy, $C_{1-2}$ alkylthio or hydroxy groups; and
W represent a group of formula —$Y^1$-$L^2$-R wherein:
$Y^1$ is a bond or represents a group —O—, —S—, —$NR^3$—, —C(=O)—O—, —O—(C=O)—, —(C=O)$NR^3$— or —$NR^3$(C=O)— wherein $R^3$ is hydrogen or $C_{1-6}$ alkyl;
$L^2$ represents a group -$Alk^1$- or a group -Q-$Alk^2$- and -$Alk^1$- represents an unsubstituted $C_{1-4}$ alkylene group, Q represents a non-fused phenyl ring or a non-fused pyridinyl or thienyl ring and $Alk^2$ represents an unsubstituted $C_{1-4}$ alkylene group; and
R represents a group of formula (X);
$R^7$ represents —COOH or —$COOR^{11}$ wherein $R^{11}$ represents —$CR^{12}R^{13}R^{14}$, and either:
(i) $R^{12}$ represents hydrogen or $C_{1-2}$ alkyl; $R^{13}$ represents hydrogen, $C_{1-4}$ alkyl, $C_{2-4}$ alkenyl or a group —($C_{1-4}$ alkyl)-O—($C_{1-4}$ alkyl); and $R^{14}$ represents hydrogen or $C_{1-2}$ alkyl; or
(ii) $R^{12}$ represents hydrogen or $C_{1-2}$ alkyl, and $R^{13}$ and $R^{14}$ form a cyclic group together with the carbon atom to which they are bonded, form a non-fused $C_{3-7}$ carbocyclyl groups which is unsubstituted or substituted by one or two substituents which are the same or different and are selected from halogen atoms and $C_{1-4}$ alkyl, $C_{1-4}$ alkylene, $C_{1-4}$ alkoxy, $C_{1-4}$ haloalkyl, hydroxyl, cyano, nitro and —NR'R'' groups wherein each R' and R'' is the same or different and represents hydrogen or $C_{1-4}$ alkyl; and
$R^8$ represents hydrogen or a $C_{1-6}$ alkyl, —(C=O)$R^9$ or —(C=O)$OR^{10}$ wherein $R^9$ is $C_{1-6}$ alkyl, non-fused phenyl, non-fused 5- to 6-membered heteroaryl, non-fused $C_{3-7}$ carbocyclyl or a group -$Alk^4$-Cyc, and $R^{10}$ is hydrogen or $C_{1-4}$ alkyl.

10. A compound as claimed in claim 9, further characterized by one or more of the following:
(i) A represents a phenyl ring fused to a dioxolanyl ring, and wherein A is unsubstituted or substituted by 1 or 2 substituents which are the same or different and represent halogen atoms or $C_{1-4}$ alkyl, $C_{1-2}$ alkoxy, $C_{1-2}$ alkylthio or hydroxy groups;
(ii) $Y^1$ is a bond;
(iii) $R^7$ represents —COOH or —$COOR^{11}$ and $R^{11}$ represents a $C_{1-4}$ alkyl or a $C_{3-7}$ carbocyclyl group; or
(iv) $R^8$ represents hydrogen.

11. A compound according to claim 1 which is (a) an amino acid derivative having formula (IC) or (ID) or a tautomer thereof, or (b) a pharmaceutically acceptable salt, N-oxide or solvate thereof:

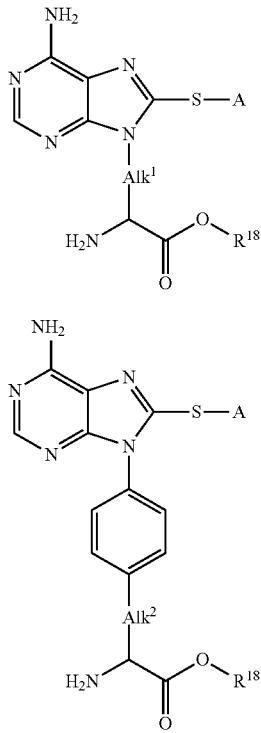

wherein:
A represents a non-fused phenyl ring or a phenyl ring fused to a dioxolanyl ring, and wherein A is unsubstituted or substituted by 1 or 2 substituents which are the same or different and represent halogen atoms or $C_{1-4}$ alkyl, $C_{1-2}$ alkoxy, $C_{1-2}$ alkylthio or hydroxy groups;
$Alk^1$ and $Alk^2$ a $C_{1-4}$ alkylene group; and
$R^{18}$ represents hydrogen, $C_{1-4}$ alkyl or a $C_{3-7}$ carbocyclyl.

12. A compound as claimed in claim 11 wherein $R^{18}$ represents hydrogen, t-butyl or cyclopentyl.

13. A compound as claimed in claim 1 which is selected from the group consisting of:
(S)-Cyclopentyl 2-amino-5-(6-amino-8-(6-iodobenzo[d][1,3]dioxol-5-ylthio)-9H-purin-9-yl)pentanoate;
(S)-Cyclopentyl 2-amino-4-(6-amino-8-(6-iodobenzo[d][1,3]dioxol-5-ylthio)-9H-purin-9-yl)butanoate;
(S)-2-Amino-5-(6-amino-8-(6-iodobenzo[d][1,3]dioxol-5-ylthio)-9H-purin-9-yl)pentanoic acid;
(S)-2-Amino-4-(6-amino-8-(6-iodobenzo[d][1,3]dioxol-5-ylthio)-9H-purin-9-yl)butanoic acid;
(R)-Cyclopentyl 2-amino-5-(6-amino-8-(6-iodobenzo[d][1,3]dioxol-5-ylthio)-9H-purin-9-yl)pentanoate;
(R)-Cyclopentyl 2-amino-4-(6-amino-8-(6-iodobenzo[d][1,3]dioxol-5-ylthio)-9H-purin-9-yl)butanoate;
(S)-tert-Butyl 2-amino-5-(6-amino-8-(6-iodobenzo[d][1,3]dioxol-5-ylthio)-9H-purin-9-yl)pentanoate;
Cyclopentyl 3-{6-amino-8-[(6-iodo-1,3-benzodioxol-5-yl)thio]-9H-purin-9-yl}-L-alaninate;
Cyclopentyl 4-{6-amino-8-[(1,3-benzodioxol-5-yl)thio]-9H-purin-9-yl}-L-phenylalaninate;
Cyclopentyl 4-{6-amino-8-[(6-bromo-1,3-benzodioxol-5-yl)thio]-9H-purin-9-yl}-L-phenylalaninate;
(R)-2-Amino-4-(6-amino-8-(6-iodo benzo[d][1,3]dioxol-5-ylthio)-9H-purin-9-yl) butanoic acid;
(R)-2-Amino-5-(6-amino-8-[(6-iodo-1,3-benzodioxol-5-ylthio)]-9H-purin-9-yl)pentanoic acid;
4-{6-Amino-8-[(1,3-benzodioxol-5-yl) thio]-9H-purin-9-yl}-L-phenylalanine; and
4-{6-Amino-8-[(6-bromo-1,3-benzo dioxol-5-yl)thio]-9H-purin-9-yl}-L-phenyl alanine.

14. A pharmaceutical composition which comprises a compound of claim 1 and a pharmaceutically acceptable carrier or diluent.

* * * * *